United States Patent [19]
Gold et al.

[11] Patent Number: 5,843,653
[45] Date of Patent: Dec. 1, 1998

[54] METHOD FOR DETECTING A TARGET MOLECULE IN A SAMPLE USING A NUCLEIC ACID LIGAND

[75] Inventors: Larry Gold, Boulder, Colo.; Craig Tuerk, Morehead, Ky.

[73] Assignee: NeXstar Pharmaceuticals, Inc., Boulder, Colo.

[21] Appl. No.: 469,609

[22] Filed: Jun. 6, 1995

Related U.S. Application Data

[63] Continuation of Ser. No. 714,131, Jun. 10, 1991, Pat. No. 5,475,096, which is a continuation-in-part of Ser. No. 536,428, Jun. 11, 1990, abandoned.

[51] Int. Cl.$^6$ ............... C12Q 1/68; C12P 19/34; C07H 21/04; C07H 21/02
[52] U.S. Cl. ............... 435/6; 435/91.2; 536/25.4; 530/412; 935/77; 935/78
[58] Field of Search ............... 435/6, 91.2; 536/25.4; 530/412; 935/77, 78

[56] References Cited

U.S. PATENT DOCUMENTS

| | | | |
|---|---|---|---|
| 4,683,195 | 7/1987 | Mullis | 435/6 |
| 4,935,363 | 6/1990 | Brown et al. | 435/6 |
| 5,070,010 | 12/1991 | Hsu | 435/6 |
| 5,270,163 | 12/1993 | Gold et al. | 435/6 |

FOREIGN PATENT DOCUMENTS

| | | | |
|---|---|---|---|
| 2 183 661 | 6/1987 | United Kingdom . | |
| WO 89/06694 | 7/1989 | WIPO . | |
| WO91/14436 | 10/1991 | WIPO . | |
| WO/92/05285 | 4/1992 | WIPO . | |
| 9214843 | 9/1992 | WIPO | 435/6 |
| WO92/14842 | 9/1992 | WIPO . | |

OTHER PUBLICATIONS

Kadonaba et al., PNAS, USA 83:5889–5893 (Aug. 1986).
Levisohn and Spiegelman (1969) Proc. Natl. Acad. Sci. USA 63:805.
Levisohn and Spiegelman (1968) Proc. Natl. Acad. Sci. USA 60:866.
Orgel (1979) Proc. R. Soc. Lon. B205:435.
Kramer et al. (1974) J. Mole. Biol. 89:719.
Joyce (1989) Gene 82:83.
Joyce and Inoue (1989) Nucleic Acids Research 17:711.
Ellington and Szostak (1990) Abstract, May 16–20 meeting on *RNA Processing*, Cold Spring Harbor Laboratory, Cold Spring Harbor, NY, p. 226.
Kinzler and Vogelstein (1989) Nucleic Acids Research 17:3645.
Oliphant et al. (1989) Molecular and Cellulary Biology 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Andrake (1988) Proc. Natl. Acad. Sci. USA 85:7942.
Carey et al. (1983) Biochem. 22(11):2601.
Cohen et al. (1969) Proc. Natl. Acad. Sci. USA 63:458.
Joyce (1989) RNA: Catalysis, Splicing . . . , Belfort et al., eds. Elsevier, p. 83.

(List continued on next page.)

*Primary Examiner*—Stephanie W. Zitomer
*Attorney, Agent, or Firm*—Swanson & Bratschun, LLC

[57] ABSTRACT

This invention discloses a method of detecting the presence or absence of a target molecule in a sample and a method of measuring the amount of a target molecule in a sample using nucleic acid ligands. In a preferred embodiment the nucleic acid ligands are identified by the method of the invention referred to as the Systematic Evolution of Ligands by EXponential Enrichment (SELEX), wherein a candidate mixture of nucleic acids are iteratively enriched in high affinity nucleic acids and amplified for further partitioning.

57 Claims, 34 Drawing Sheets

OTHER PUBLICATIONS

Kacian et al. (1972)Proc. Natl. Acad. Sci. USA 69:3038.
Kinzler et al. (1990) Mol. Cell. Biol. 10(2):634.
Lestienne et al. (1983) Biochime. 65:49.
Levisohn and Spiegelman (1969) Proc. Natl. Acad. Sci. USA 63:805.
Ma and Ptashne (1987) Cell 51:113.
Maniatis (1982) *Molecular Cloning: a laboratory manual.* Cold Spring Harbor, NY p. 118.
Maniatis et al. (1987) Science 236:1237.
Miele et al. (1983) J. Mol. Biol. 171:281.
Mills et al. (1967) Proc. Natl. Acad. Sci. USA 58:217.
Mills et al (1973) Science 180:916.
Min et al (1988) Nucleic Acids Res. 16:5075.
Muesing et al. (1985) Nature 313:450.
Oliphant et al. (1990) Molecular and Cellular Biology 9:2944.
Ou et al. (1988) Science 239:295.
Romaniuk et al. (1987) Biochem. 26(6):1563.
Saffhill et al. (1970) J. Mol. Biol. 51:531.
Sambrook et al. (1989) *Molecular Cloning: A Laboratory Manual.* Cold Spring Harbor, NY, Section 8.9–8.10.
Uhlenbeck et al. (1983) J. Biomolecular Structure and Dynamics 1:539.
Watson et al (1987) *Molecular Biology of the Gene.* Benjamin/Cummings Publishing Co., Inc. California, pp. 267, 295,323,361,394,396,397 and 405.

FIG. 1

```
              A  A
           U     A  C
        -30•A    A  C
                 U-G
                 C-G
                 C-G
                 G-C•-20
              A-U
   ...uaaauauauCAAG   AUAAACUAAGGAAUaucuaug...
     -40•                •-10      0•
                  SEQ. I.D. NO. 345
```

VARIABLE TEMPLATE SYNTHESIS USING TERMINAL TRANSFERASE
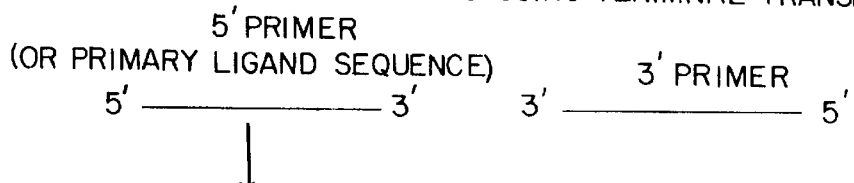
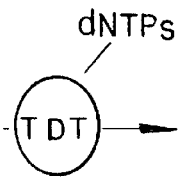
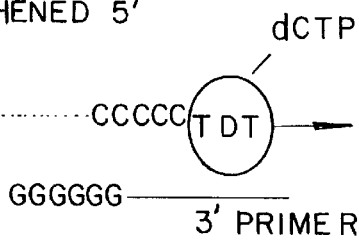
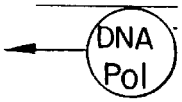
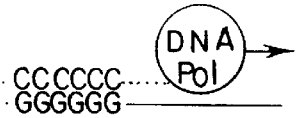
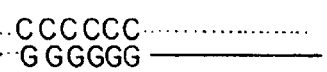
FIG. 8

ANCHORING OF BRIDGING OLIGONUCLEOTIDE & SECONDARY LIGAND EVOLUTION.
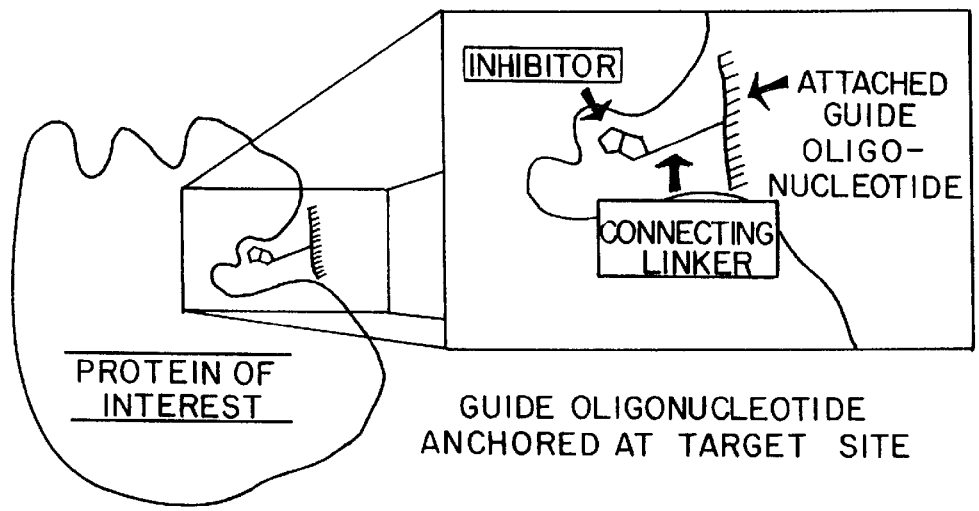
GUIDE OLIGONUCLEOTIDE ANCHORED AT TARGET SITE
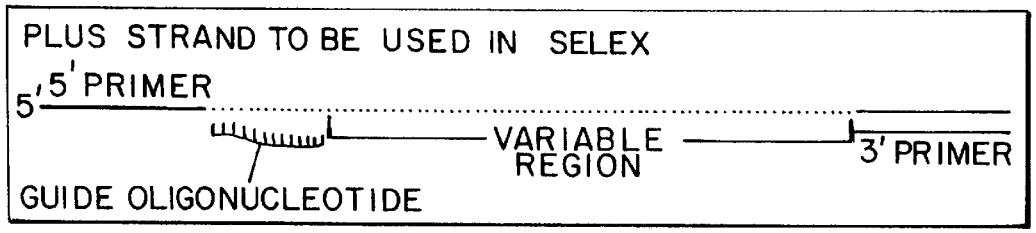
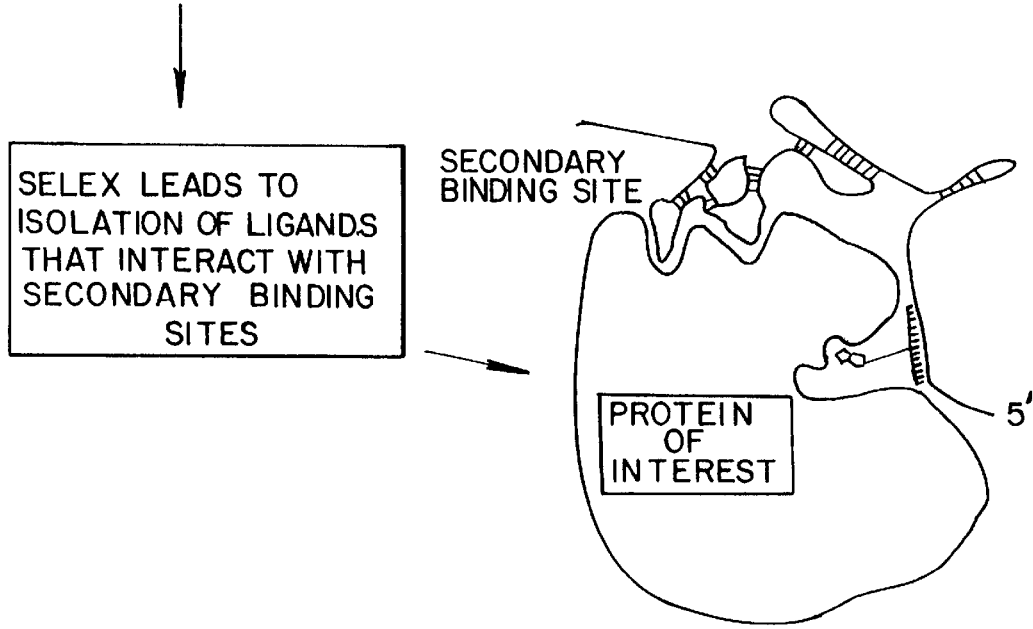
FIG. 10

FIG. 12A

T7 promoter

5'-taatacgactcactataggagcatcagactttaatctgacaatcaag-3'  SEQ. I.D. NO. 350
3'-attatgctgagtgatatccctcgtagtctgaaattagact-5'  SEQ. I.D. NO. 351 ligation  3'-gttagttc...-5' in vitro transcript

5'-gggagcaucagacuuuaaucugacaaucaag[32n]aucuaugaaagaauu

FIG. 12B

△ 1.1  ucaagAAUUCCGUUUUCAGUCGGGAAAAACUGAACA aucu  (13)

O 1.3  ucaagAAUAUCUUCCGAAGCCGAACGGGAAAACCGG Caucu  (1)

● 1.3  --------------- G -------------- A-----  (1)

□ 1.4  ucaagGGCAUCUGGGAGGGUAAGGGUAAGGUUGUCGGaucu  (4)

△ 1.1 = SEQ. I.D. NO. 355    ● 1.3 = SEQ. I.D. NO. 357

O 1.3 = SEQ. I.D. NO. 356    □ 1.4 = SEQ. I.D. NO. 358

ISOLATE

○ 2.1a  ucaag--AAUAUA-UCCGAACUCGACGGGAUAACGAGAA-Gaucu (3)

□ 2.2b  ucaaguACCUAGGUGAUAAAAGGGAGAACACGUGUGa-cu (13)

● 2.5b  ucaagACAGUAUCCGUUCUUGAUCAUCGGGACAAAUGaucu (3)

△ 1.1   ucaagAAUUCCGUUUUCAGUCGGGAAAAACUGAACAAUcu (13)

○ 2.1a = SEQ. I.D. NO. 359       ● 2.5b = SEQ. I.D. NO. 361

□ 2.2b = SEQ. I.D. NO. 360       △ 1.1 = SEQ. I.D. NO. 362

SEQ. I.D. NO. 363

SEQ. I.D. NO. 364

SEQ. I.D. NO. 365    SEQ. I.D. NO. 366

| | A | C | G | U |
|---|---|---|---|---|
| -4 | 36 | 0 | 0 | 0 |
| -5 | 0 | 36 | 0 | 0 |
| -6 | 4 | 3 | 1 | 28 |
| -7 | 36 | 0 | 0 | 0 |
| -10 | 36 | 0 | 0 | 0 |

| | AU | CG | UA | GC | UG | GU | Bulge | END |
|---|---|---|---|---|---|---|---|---|
| -8/-3 | 0 | 24 | 0 | 12 | 0 | 0 | 0 | 0 |
| -9/-2 | 0 | 25 | 0 | 10 | 1 | 0 | 36 | 0 |
| -11/-1 | 0 | 24 | 2 | 10 | 0 | 0 | 0 | 1 |
| -12/+1 | 8 | 1 | 8 | 10 | 7 | 1 | 3 | 3 |
| -13/+2 | 6 | 5 | 8 | 9 | 3 | 1 | 3 | 4 |
| -14/+3 | 9 | 0 | 4 | 10 | 2 | 3 | 6 | 8 |
| -15/+4 | 4 | 0 | 9 | 6 | 0 | 1 | 0 | 2 |
| -16/+5 | 10 | 1 | 2 | 1 | 1 | 3 | 1 | 1 |
| -17/+6 | 0 | 4 | 6 | 1 | 4 | 2 | | |

FIG.19A    SEQ. I.D. NO. 367

FIG.21A
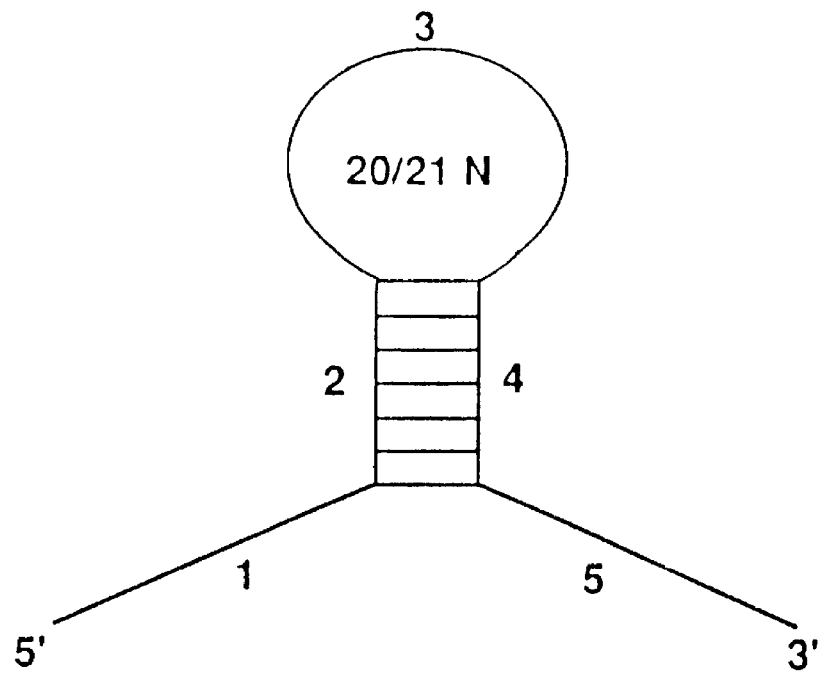
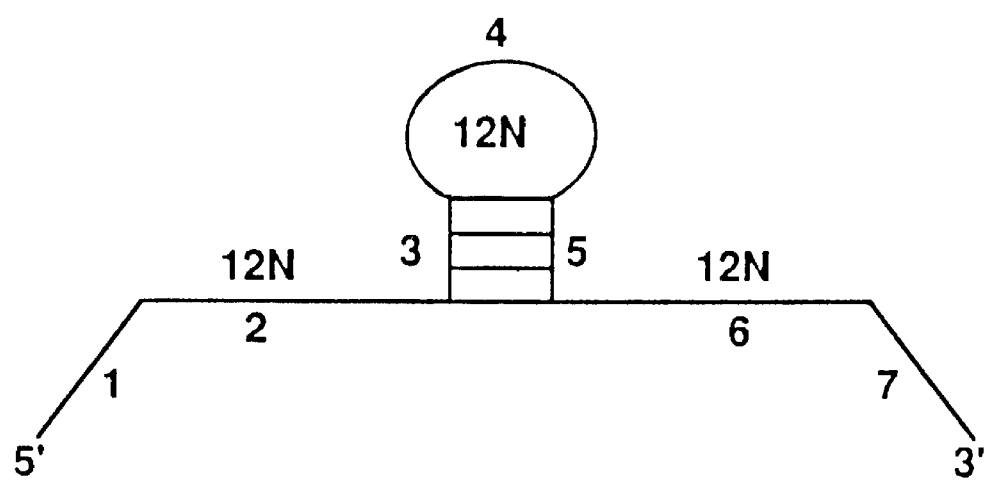
FIG.21B

Motif I (6a)

```
                UUGAGAAA      G
                         CAC U
5'...gGGUGCA    |||  ||| GUG U     (NUCLEOTIDES 2-38 OF SEQ. I.D. NO. 301)
3'...ucuaUGU    |||  |||
                --CUCA-G      U
```

Motif II (1c)

```
                AAGAUA      UCU
                      CAGC
5'...AGAUG            GUCG      A
3'...ucuAC
              -ACA-G      UAG
```

SEQ. I.D. NO. 368

Motif III (9a)

```
CC   UUGaucua-        ugaa-3'
A GG ||||      GCUU-5'
A CC ||||
UU   --CUAGUAA
```

SEQ. I.D. NO. 369

WT (Motif II-like Domain)

```
      ACGGUA
U
A  GACGCUG  ||  CA......3'
   CUGCGAC  ||  GU......5'
A
      -GCG-G
```

SEQ. I.D. NO. 370

FIG. 23

Motif II

SEQUENCE LISTING ( 1 ) GENERAL INFORMATION:

( i i i ) NUMBER OF SEQUENCES: 374

( 2 ) INFORMATION FOR SEQ ID NO:1:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:1:

N N N C G N A A N U  C G N N N           1 5

( 2 ) INFORMATION FOR SEQ ID NO:2:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:2:

A A G U N N G U N N  C N N N N           1 5

( 2 ) INFORMATION FOR SEQ ID NO:3:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:3:

A A G U C C G U A A  C A C A C           1 5

( 2 ) INFORMATION FOR SEQ ID NO:4:

( i ) SEQUENCE CHARACTERISTICS:
        ( A ) LENGTH: 45 nucleotides (B) TYPE: nucleic acid
(C) STRANDEDNESS: single
(D) TOPOLOGY: linear (xi) SEQUENCE DESCRIPTION: SEQ ID NO:4:

TAATACGACT CACTATAGGG AGCCAACACC ACAATTCCAA TCAAG      45

(2) INFORMATION FOR SEQ ID NO:5:

(i) SEQUENCE CHARACTERISTICS:
(A) LENGTH: 30 nucleotides
(B) TYPE: nucleic acid
(C) STRANDEDNESS: single
(D) TOPOLOGY: linear (xi) SEQUENCE DESCRIPTION: SEQ ID NO:5:

GGGCTATAAA CTAAGGAATA TCTATGAAAG      30

(2) INFORMATION FOR SEQ ID NO:6:

(i) SEQUENCE CHARACTERISTICS:
(A) LENGTH: 37 nucleotides
(B) TYPE: nucleic acid
(C) STRANDEDNESS: single
(D) TOPOLOGY: linear (xi) SEQUENCE DESCRIPTION: SEQ ID NO:6:

GAATTGTGGT GTTGGCTCCC TATAGTGAGT CGTATTA      37

(2) INFORMATION FOR SEQ ID NO:7:

(i) SEQUENCE CHARACTERISTICS:
(A) LENGTH: 42 nucleotides
(B) TYPE: nucleic acid
(C) STRANDEDNESS: single
(D) TOPOLOGY: linear (xi) SEQUENCE DESCRIPTION: SEQ ID NO:7:

ATATTCCTTA GTTTATAGCC CNNNNNNNA GGCTCTTGAT TG      42

(2) INFORMATION FOR SEQ ID NO:8:

(i) SEQUENCE CHARACTERISTICS:
(A) LENGTH: 31 nucleotides
(B) TYPE: nucleic acid
(C) STRANDEDNESS: single
(D) TOPOLOGY: linear (xi) SEQUENCE DESCRIPTION: SEQ ID NO:8:

GTTTCAATAG AGATATAAAA TTCTTTCATA G      31

(2) INFORMATION FOR SEQ ID NO:9:

(i) SEQUENCE CHARACTERISTICS:
(A) LENGTH: 20 nucleotides
(B) TYPE: nucleic acid
(C) STRANDEDNESS: single
(D) TOPOLOGY: linear (xi) SEQUENCE DESCRIPTION: SEQ ID NO:9:

UUCCGNNNNN NNNCGGGAAA      20

(2) INFORMATION FOR SEQ ID NO:10:

(i) SEQUENCE CHARACTERISTICS:
(A) LENGTH: 31 nucleotides
(B) TYPE: nucleic acid
(C) STRANDEDNESS: single (D) TOPOLOGY: linear (xi) SEQUENCE DESCRIPTION: SEQ ID NO:10:

GTTTCAATAG AGATATAAAA TTCTTTCATA G    31

(2) INFORMATION FOR SEQ ID NO:11:

(i) SEQUENCE CHARACTERISTICS:
        (A) LENGTH: 91 nucleotides
        (B) TYPE: nucleic acid
        (C) STRANDEDNESS: single
        (D) TOPOLOGY: linear (xi) SEQUENCE DESCRIPTION: SEQ ID NO:11:

GGGAGCCAAC ACCACAAUUC CAAUCAAGNN NNNNNNNNN NNNNNNNNN    50

NNNNNNNNNN AUCUAUGAAA GAAUUUUAUC UCUAUUGAAA C    91

(2) INFORMATION FOR SEQ ID NO:12:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:12:

ACGAAACAAA UAAGGAGGAG GAGGGAUUGU    30

(2) INFORMATION FOR SEQ ID NO:13:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:13:

AGGAGGAGGA GGGAGAGCGC AAAUGAGAUU    30

(2) INFORMATION FOR SEQ ID NO:14:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:14:

AGGAGGAGGA GGUAGAGCAU GUAUUAAGAG    30

(2) INFORMATION FOR SEQ ID NO:15:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:15:

UAAGCAAGAA UCUACGAUAA AUACGUGAAC    30

(2) INFORMATION FOR SEQ ID NO:16:

(i) SEQUENCE CHARACTERISTICS:
        (A) LENGTH: 30 nucleotides
        (B) TYPE: nucleic acid
        (C) STRANDEDNESS: single (D) TOPOLOGY: linear (xi) SEQUENCE DESCRIPTION: SEQ ID NO:16:

AGUGAAAGAC GACAACGAAA AACGACCACA 30

(2) INFORMATION FOR SEQ ID NO:17:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (xi) SEQUENCE DESCRIPTION: SEQ ID NO:17:

CCGAGCAUGA GCCUAGUAAG UGGUGGAUA 29

(2) INFORMATION FOR SEQ ID NO:18:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:18:

UAAUAAGAGA UACGACAGAA UACGACAUAA 30

(2) INFORMATION FOR SEQ ID NO:19:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:19:

ACAUCGAUGA CCGGAAUGCC GCACACAGAG 30

(2) INFORMATION FOR SEQ ID NO:20:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:20:

CCUCAGAGCG CAAGAGUCGA ACGAAUACAG 30

(2) INFORMATION FOR SEQ ID NO:21:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:21:

CUCAUGGAGC GCAAGACGAA UAGCUACAUA 30

(2) INFORMATION FOR SEQ ID NO:22:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear ( x i ) SEQUENCE DESCRIPTION: SEQ ID NO:22:

ACAUCGAUGA CCGGAAUGCC GCACACAGAG 30

( 2 ) INFORMATION FOR SEQ ID NO:23:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:23:

CCUCAGAGCG CAAGAGUCGA ACGAAUACAG 30

( 2 ) INFORMATION FOR SEQ ID NO:24:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:24:

CGGGUGAUUA GUACUGCAGA GCGGAAUGAC 30

( 2 ) INFORMATION FOR SEQ ID NO:25:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:25:

UGCGAUAAGA CUUGCUGGGC GAGACAAACA 30

( 2 ) INFORMATION FOR SEQ ID NO:26:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:26:

AGUCCACAGG GCACUCCCAA AGGGCAAACA 30

( 2 ) INFORMATION FOR SEQ ID NO:27:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:27:

ACUCAUGGAG CGCUCGACGA UCACCAUCGA 30

( 2 ) INFORMATION FOR SEQ ID NO:28:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:28:

CAAGGGAGAA UGUCUGUAGC GUCCAGGUA 29

(2) INFORMATION FOR SEQ ID NO:29:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:29:

CGACGCAGAG AUACGAAUAC GACAAAACGC 30

(2) INFORMATION FOR SEQ ID NO:30:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:30:

GAGGGUGAGG UGGGAGGCAG UGGCAGUUUA 30

(2) INFORMATION FOR SEQ ID NO:31:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:31:

UGAACUAGGG GGAGGGAGGG UGGAAGACAG 30

(2) INFORMATION FOR SEQ ID NO:32:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (xi) SEQUENCE DESCRIPTION: SEQ ID NO:32:

GUGGAGGGGA CGUGGAGGGG AGAGCAAGA 29

(2) INFORMATION FOR SEQ ID NO:33:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:33:

CUCAUGGAGC GCAAGACGAA UAGCUACAUA 30

(2) INFORMATION FOR SEQ ID NO:34:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (xi) SEQUENCE DESCRIPTION: SEQ ID NO:34:

CCAUAGAGGC CACAAGCAAA GACUACGCA 29

( 2 ) INFORMATION FOR SEQ ID NO:35:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:35:

CCUACAAGAA AAGAGGGAAG GAGAAAAAAA     30

( 2 ) INFORMATION FOR SEQ ID NO:36:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:36:

GCCGGATCCG GGCCTCATGT GAA     23

( 2 ) INFORMATION FOR SEQ ID NO:37:

( i ) SEQUENCE CHARACTERISTICS:
        ( A ) LENGTH: 48 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:37:

CCGAAGCTTA ATACGACTCA CTATAGGGAG CTCAGAATAA ACGCTCAA     48

( 2 ) INFORMATION FOR SEQ ID NO:38:

( i ) SEQUENCE CHARACTERISTICS:
        ( A ) LENGTH: 77 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:38:

GGGAGCUCAG AAUAAACGCU CAANNNNNNN NNNNNNNNN NNNNNNNNN     50

NNNUUCGACA UGAGGCCCGG AUCCGGC     77

( 2 ) INFORMATION FOR SEQ ID NO:39:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:39:

CGCUCAAUAA GGAGGCCACG GACAACAUGG UACAGCUUCG ACA     43

( 2 ) INFORMATION FOR SEQ ID NO:40:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:40:

CGCUCAAUAA GGAGGCCACA ACAAANGGAG ACAAAUUCGA CA     42

( 2 ) INFORMATION FOR SEQ ID NO:41:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:41:

CGCUCAAUAA GGAGGCCACA CACAUAGGUA GACAUGUUCG ACA　　　　　　　　　　　　43

( 2 ) INFORMATION FOR SEQ ID NO:42:

( i ) SEQUENCE CHARACTERISTICS:
        ( A ) LENGTH: 45 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:42:

CGCUCAAUAA GGAGGCCACA UACAAAGGA UGAGUAAAUU CGACA　　　　　　　　　　　45

( 2 ) INFORMATION FOR SEQ ID NO:43:

( i ) SEQUENCE CHARACTERISTICS:
        ( A ) LENGTH: 45 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:43:

CGCUCAAUAA GGAGGCCACA AAUGCUGGUC CACCGAGAUU CGACA　　　　　　　　　　　45

( 2 ) INFORMATION FOR SEQ ID NO:44:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:44:

CGCUCAAUAG GGAGGGCACG GGAAGGGUGA GUGGAUAUUC GACA　　　　　　　　　　　　44

( 2 ) INFORMATION FOR SEQ ID NO:45:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:45:

CGCUCAAUAA GGAGGCCACA AGUUCGACA　　　　　　　　　　　　　　　　　　　　　　29

( 2 ) INFORMATION FOR SEQ ID NO:46:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:46:

CGCUCAAUAA GGAGGGCCAC AGAUGUAAUG GAAACUUCGA CA　　　　　　　　　　　　　42

( 2 ) INFORMATION FOR SEQ ID NO:47:

( i ) SEQUENCE CHARACTERISTICS:
    ( A ) LENGTH: 46 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:47:

CGCUCAAUAA GGAGGCCACA UACAAAAGGA UGAGUAAAAU UCGACA    46

( 2 ) INFORMATION FOR SEQ ID NO:48:

( i ) SEQUENCE CHARACTERISTICS:
    ( A ) LENGTH: 10 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:48:

UUGAGAUACA    10

( 2 ) INFORMATION FOR SEQ ID NO:49:

( i ) SEQUENCE CHARACTERISTICS:
    ( A ) LENGTH: 45 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:49:

TAATACGACT CACTATAGGG AGCCAACACC ACAATTCCAA TCAAG    45

( 2 ) INFORMATION FOR SEQ ID NO:50:

( i ) SEQUENCE CHARACTERISTICS:
    ( A ) LENGTH: 49 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:50:

TAATACGACT CACTATAGGG AGCATCAGAC TTTTAATCTG ACAATCAAG    49

( 2 ) INFORMATION FOR SEQ ID NO:51:

( i ) SEQUENCE CHARACTERISTICS:
    ( A ) LENGTH: 24 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:51:

ATCTATGAAA GAATTTTATA TCTC    24

( 2 ) INFORMATION FOR SEQ ID NO:52:

( i ) SEQUENCE CHARACTERISTICS:
    ( A ) LENGTH: 37 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:52:

GAATTGTGGT GTTGGCTCCC TATAGTGAGT CGTATTA    37

( 2 ) INFORMATION FOR SEQ ID NO:53:

( i ) SEQUENCE CHARACTERISTICS:

(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:53:

TCAGATTAAA AGTCTGATGC TCCCTATAGT GAGTCGTATT A 41

(2) INFORMATION FOR SEQ ID NO:54:

(i) SEQUENCE CHARACTERISTICS:
(A) LENGTH: 50 nucleotides
(B) TYPE: nucleic acid
(C) STRANDEDNESS: single
(D) TOPOLOGY: linear (xi) SEQUENCE DESCRIPTION: SEQ ID NO:54:

TTTCATAGAT NNNNNNNNN NNNNNNNNN NNNNNNNNN NNCTTGATTG 50

(2) INFORMATION FOR SEQ ID NO:55:

(i) SEQUENCE CHARACTERISTICS:
(A) LENGTH: 31 nucleotides
(B) TYPE: nucleic acid
(C) STRANDEDNESS: single
(D) TOPOLOGY: linear (xi) SEQUENCE DESCRIPTION: SEQ ID NO:55:

CCGGATCCGT TTCAATAGAG ATATAAAATT C 31

(2) INFORMATION FOR SEQ ID NO:56:

(i) SEQUENCE CHARACTERISTICS:
(A) LENGTH: 31 nucleotides
(B) TYPE: nucleic acid
(C) STRANDEDNESS: single
(D) TOPOLOGY: linear (xi) SEQUENCE DESCRIPTION: SEQ ID NO:56:

GTTTCAATAG AGATATAAAA TTCTTTCATA G 31

(2) INFORMATION FOR SEQ ID NO:57:

(i) SEQUENCE CHARACTERISTICS:
(A) LENGTH: 32 nucleotides
(B) TYPE: nucleic acid
(C) STRANDEDNESS: single
(D) TOPOLOGY: linear (xi) SEQUENCE DESCRIPTION: SEQ ID NO:57:

CCGAAGCTTC TAATACGACT CACTATAGGG AG 32

(2) INFORMATION FOR SEQ ID NO:58:

(i) SEQUENCE CHARACTERISTICS:
(A) LENGTH: 72 nucleotides
(B) TYPE: nucleic acid
(C) STRANDEDNESS: single
(D) TOPOLOGY: linear (xi) SEQUENCE DESCRIPTION: SEQ ID NO:58:

AGAGATATAA AATTCTTTCA TAGNNNNTTT TCCCGNNNNN NNNCGGAANN 50

CTTGATTGTC AGATTAAAAG TC 72

(2) INFORMATION FOR SEQ ID NO:59:

(i) SEQUENCE CHARACTERISTICS:

( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:59:

GACGTTGTAA AACGACGGCC 20

( 2 ) INFORMATION FOR SEQ ID NO:60:

( i ) SEQUENCE CHARACTERISTICS:
        ( A ) LENGTH: 97 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:60:

GGGAGCAUCA GACUUUUAAU CUGACAAUCA AGNNNNNNNN NNNNNNNNN 50

NNNNNNNNN NNNNAUCUAU GAAAGAAUUU UAUAUCUCUA UUGAAAC 97

( 2 ) INFORMATION FOR SEQ ID NO:61:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:61:

UCAAGAAUUC CGUUUUCAGU CGGGAAAAAC UGAACAAUCU 40

( 2 ) INFORMATION FOR SEQ ID NO:62:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:62:

UCAAGCGUAG GUUAUGAAUG GAGGAGGUAG GGUCGUAAUC U 41

( 2 ) INFORMATION FOR SEQ ID NO:63:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:63:

UCAAGAAUAU CUUCCGAAGC CGAACGGGAA AACCGGCAUC U 41

( 2 ) INFORMATION FOR SEQ ID NO:64:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:64:

UCAAGAAUAU CUUCCGAGGC CGAACGGGAA AACCGACAUC U 41

( 2 ) INFORMATION FOR SEQ ID NO:65:

( i ) SEQUENCE CHARACTERISTICS:

(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:65:

UCAAGAAUAC CUUCCGAGGC CGAACGGGAA AACCGGCAUC U  41

(2) INFORMATION FOR SEQ ID NO:66:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:66:

UCAAGAAUAU CUUCCGAGGC CGAACGGGAA AACCGGCACC U  41

(2) INFORMATION FOR SEQ ID NO:67:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:67:

UCAAGAAUAU CUUCCGAGGC CGAACGGGAA AACCGGCAAC U  41

(2) INFORMATION FOR SEQ ID NO:68:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:68:

UCAAGGGCAU CUGGGAGGGU AAGGGUAAGG UUGUCGGAUC U  41

(2) INFORMATION FOR SEQ ID NO:69:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:69:

UCAAGCCCAC GGAUGUCGAA GGUGGAGGUU GGGCGGCAUC U  41

(2) INFORMATION FOR SEQ ID NO:70:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:70:

UCAAGAAGAA GAUUACCCAA GCGCAGGGGA GAAGCGCAUC U  41

(2) INFORMATION FOR SEQ ID NO:71:

(i) SEQUENCE CHARACTERISTICS:
(A) LENGTH: 41 nucleotides
(B) TYPE: nucleic acid (C) STRANDEDNESS: single
(D) TOPOLOGY: linear (x i) SEQUENCE DESCRIPTION: SEQ ID NO:71:

UCAAGGAAUC GACCCAAGCC AAAGGGGAUA AUGCGGCAUC U   41

(2) INFORMATION FOR SEQ ID NO:72:

(i) SEQUENCE CHARACTERISTICS:
(A) LENGTH: 41 nucleotides
(B) TYPE: nucleic acid
(C) STRANDEDNESS: single
(D) TOPOLOGY: linear (x i) SEQUENCE DESCRIPTION: SEQ ID NO:72:

UCAAGGAUUA ACCGACGCCA ACGGGAGAAU GGCAGGGAUC U   41

(2) INFORMATION FOR SEQ ID NO:73:

(i) SEQUENCE CHARACTERISTICS:
(A) LENGTH: 40 nucleotides
(B) TYPE: nucleic acid
(C) STRANDEDNESS: single
(D) TOPOLOGY: linear (x i) SEQUENCE DESCRIPTION: SEQ ID NO:73:

UCAAGAGAGU AUCAUCGUGC CGGCGGGAUA UCGGCGAUCU   40

(2) INFORMATION FOR SEQ ID NO:74:

(i) SEQUENCE CHARACTERISTICS:
(A) LENGTH: 41 nucleotides
(B) TYPE: nucleic acid
(C) STRANDEDNESS: single
(D) TOPOLOGY: linear (x i) SEQUENCE DESCRIPTION: SEQ ID NO:74:

UCAAGAGAGU AUCAUCCGUG CCGGCGGGAU AUCGGCGAUC U   41

(2) INFORMATION FOR SEQ ID NO:75:

(i) SEQUENCE CHARACTERISTICS:
(A) LENGTH: 41 nucleotides
(B) TYPE: nucleic acid
(C) STRANDEDNESS: single
(D) TOPOLOGY: linear (x i) SEQUENCE DESCRIPTION: SEQ ID NO:75:

UCAAGUUUGA ACAAGCGGAA CAUGCACAGC UACACUCAUC U   41

(2) INFORMATION FOR SEQ ID NO:76:

(i) SEQUENCE CHARACTERISTICS:
(A) LENGTH: 41 nucleotides
(B) TYPE: nucleic acid
(C) STRANDEDNESS: single
(D) TOPOLOGY: linear (x i) SEQUENCE DESCRIPTION: SEQ ID NO:76:

UCAAGUUCGA ACAAGCGGAA CAUGCACAGC CACACUCAUC U   41

(2) INFORMATION FOR SEQ ID NO:77:

(i) SEQUENCE CHARACTERISTICS:
(A) LENGTH: 40 nucleotides
(B) TYPE: nucleic acid
(C) STRANDEDNESS: single
(D) TOPOLOGY: linear ( x i ) SEQUENCE DESCRIPTION: SEQ ID NO:77:

UCAAGCUCAC GGAUGUCGAA GGUGGAGGUU GGGCGGCAUC  40

( 2 ) INFORMATION FOR SEQ ID NO:78:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:78:

UCAAGCAUAG ACCGCGUAGG GGGAGGUAGG AGCGGCCAUC U  41

( 2 ) INFORMATION FOR SEQ ID NO:79:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:79:

UCAAGCUCUU UCAUAGACCG CGGAGGAGGU UGGGAGAUCU  40

( 2 ) INFORMATION FOR SEQ ID NO:80:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:80:

UCAAGUUCCU AGUAGACUGA GGGUGGGAGU GGUGGAUGUC U  41

( 2 ) INFORMATION FOR SEQ ID NO:81:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:81:

UCAAGCCAAU UACUUAUUUC GCCGACUAAC CCCAAGAAUC U  41

( 2 ) INFORMATION FOR SEQ ID NO:82:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:82:

UCAAGGAGGC CAAUUCCAUG UAACAAGGUG CAACUAAUAU CU  42

( 2 ) INFORMATION FOR SEQ ID NO:83:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:83:

UCAAGUGCGU AUGAAGAGUA UUUAGUGCAG GCCACGGAUC U                   41

(2) INFORMATION FOR SEQ ID NO:84:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:84:

UCAAGUAAUG ACCAGAGGCC CAACUGGUAA ACGGGCGGUC U                   41

(2) INFORMATION FOR SEQ ID NO:85:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:85:

UCAAGAGACU CCACCUGACG UGUUCAACUA UCUGGCGAUC U                   41

(2) INFORMATION FOR SEQ ID NO:86:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:86:

UCAAGAAUUC CGUUUCAGU CGGGAAAAAC UGAACAAUCU                      40

(2) INFORMATION FOR SEQ ID NO:87:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:87:

UCAAGAAUAU CUUCCGAAGC CGAACGGGAA AACCGGCAUC U                   41

(2) INFORMATION FOR SEQ ID NO:88:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO:88:

UCAAGGUUUC CGAAAGAAAU CGGGAAAACU GUCU                           34

(2) INFORMATION FOR SEQ ID NO:89:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:89:

UCAAGUAGAU AUCCGAAGCU CAACGGGAUA AUGAGCAUCU                     40

( 2 ) INFORMATION FOR SEQ ID NO:90:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:90:

UCAAGAUAUG AUCCGUAAGA GGACGGGAUA AACCUCAACU     40

( 2 ) INFORMATION FOR SEQ ID NO:91:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:91:

UCAAGGAAUC GACCCAAGCC AAAGGGGAUA AUGCGGCAUC U     41

( 2 ) INFORMATION FOR SEQ ID NO:92:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:92:

UCAAGUCAUA UUACCGUUAC UCCUCGGGAU AAAGGAGAUC U     41

( 2 ) INFORMATION FOR SEQ ID NO:93:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:93:

UCAAGUAAUG ACCAGAGGCC CAACUGGUAA ACGGGCGGUC U     41

( 2 ) INFORMATION FOR SEQ ID NO:94:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:94:

UCAAGGAUUA ACCGACGCCA ACGGGAGAAU GGCAGGGAUC U     41

( 2 ) INFORMATION FOR SEQ ID NO:95:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:95:

UCAAGAAUAU AUCCGAACUC GACGGGAUAA CGAGAAGAGC U     41

( 2 ) INFORMATION FOR SEQ ID NO:96:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:96:

UCAAGAAGAA GAUUACCCAA GCGCAGGGGA GAAGCGCAUC U     41

( 2 ) INFORMATION FOR SEQ ID NO:97:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:97:

UCAAGUAAAU GAGUCCGUAG GAGGCGGGAU AUCUCCAACU     40

( 2 ) INFORMATION FOR SEQ ID NO:98:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:98:

UCAAGAGAGU AUCAUCCGUG CCGGCGGGAU AUCGGCGAUC U     41

( 2 ) INFORMATION FOR SEQ ID NO:99:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:99:

UCAAGAAUAA UCCGACUCGC GGGAUAACGA GAAGAGCU     38

( 2 ) INFORMATION FOR SEQ ID NO:100:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:100:

UCAAGUUCGA ACAAGCGGAA CAUGCACAGC CACACUCAUC U     41

( 2 ) INFORMATION FOR SEQ ID NO:101:

( i ) SEQUENCE CHARACTERISTICS:
        ( A ) LENGTH: 48 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:101:

CAAGUUAAAC AUAAUCCGUG AUCUUUCACA CGGGAGAUCU AUGAAAGA     48

( 2 ) INFORMATION FOR SEQ ID NO:102:

( i ) SEQUENCE CHARACTERISTICS:
  ( A ) LENGTH: 41 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:102:

AAUCAAGUAC CUAGGUGAUA AAAGGGAGAA CACGUGUGAC U    41

( 2 ) INFORMATION FOR SEQ ID NO:103:

( i ) SEQUENCE CHARACTERISTICS:
  ( A ) LENGTH: 40 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:103:

AAUCAAGUAC CUAGGUGAUA AAAGGGAGAA CACGUGUACU    40

( 2 ) INFORMATION FOR SEQ ID NO:104:

( i ) SEQUENCE CHARACTERISTICS:
  ( A ) LENGTH: 41 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:104:

UCAAGAUAGU AUCCGUUCUU GAUCAUCGGG ACAAAUGAUC U    41

( 2 ) INFORMATION FOR SEQ ID NO:105:

( i ) SEQUENCE CHARACTERISTICS:
  ( A ) LENGTH: 46 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:105:

UCAAGUGAAA CUUAACCGUU AUCAUAGAUC GGGACAAAUC UAUGAA    46

( 2 ) INFORMATION FOR SEQ ID NO:106:

( i ) SEQUENCE CHARACTERISTICS:
  ( A ) LENGTH: 44 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:106:

UCAAGCGUAG GUUAUGAAUG GAGGAGGUAG GGUCGUAAUC UAUG    44

( 2 ) INFORMATION FOR SEQ ID NO:107:

( i ) SEQUENCE CHARACTERISTICS:
  ( A ) LENGTH: 50 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:107:

AUCUGACAAU CAAGGGCAUC UGGGAGGGUA AGGUAAGGU UGUCGGAUCU    50

( 2 ) INFORMATION FOR SEQ ID NO:108:

( i ) SEQUENCE CHARACTERISTICS:
  ( A ) LENGTH: 41 nucleotides (B) TYPE: nucleic acid
(C) STRANDEDNESS: single
(D) TOPOLOGY: linear (xi) SEQUENCE DESCRIPTION: SEQ ID NO:108:

UCAAGCCCAC GGAUGUCGAA GGUGGAGGUU GGGCGGCAUC U                41

(2) INFORMATION FOR SEQ ID NO:109:

(i) SEQUENCE CHARACTERISTICS:
(A) LENGTH: 40 nucleotides
(B) TYPE: nucleic acid
(C) STRANDEDNESS: single
(D) TOPOLOGY: linear (xi) SEQUENCE DESCRIPTION: SEQ ID NO:109:

UCAAGCUCAC GGAUGUCGAA GGUGGAGGUU GGGCGGCAUC                  40

(2) INFORMATION FOR SEQ ID NO:110:

(i) SEQUENCE CHARACTERISTICS:
(A) LENGTH: 44 nucleotides
(B) TYPE: nucleic acid
(C) STRANDEDNESS: single
(D) TOPOLOGY: linear (xi) SEQUENCE DESCRIPTION: SEQ ID NO:110:

UCAAGCAUAG ACCGCGUAGG GGGAGGUAGG AGCGGCCAUC UAUG             44

(2) INFORMATION FOR SEQ ID NO:111:

(i) SEQUENCE CHARACTERISTICS:
(A) LENGTH: 48 nucleotides
(B) TYPE: nucleic acid
(C) STRANDEDNESS: single
(D) TOPOLOGY: linear (xi) SEQUENCE DESCRIPTION: SEQ ID NO:111:

UCAAGCUCUU UCAUAGACCG CGGAGGAGGU UGGGAGAUCU AUGAAAGA         48

(2) INFORMATION FOR SEQ ID NO:112:

(i) SEQUENCE CHARACTERISTICS:
(A) LENGTH: 43 nucleotides
(B) TYPE: nucleic acid
(C) STRANDEDNESS: single
(D) TOPOLOGY: linear (xi) SEQUENCE DESCRIPTION: SEQ ID NO:112:

UCAAGUUCCU AGUAGACUGA GGGUGGGAGU GGUGGAUGUC UAU              43

(2) INFORMATION FOR SEQ ID NO:113:

(i) SEQUENCE CHARACTERISTICS:
(A) LENGTH: 34 nucleotides
(B) TYPE: nucleic acid
(C) STRANDEDNESS: single
(D) TOPOLOGY: linear (xi) SEQUENCE DESCRIPTION: SEQ ID NO:113:

UCCGUGAUCU UUCACACGGG AGAUCUAUGA AAGA                        34

(2) INFORMATION FOR SEQ ID NO:114:

(i) SEQUENCE CHARACTERISTICS:
(A) LENGTH: 27 nucleotides
(B) TYPE: nucleic acid
(C) STRANDEDNESS: single (D) TOPOLOGY: linear (xi) SEQUENCE DESCRIPTION: SEQ ID NO:114:

UUCCGAAAGA AAUCGGGAAA ACUGUCU 27

(2) INFORMATION FOR SEQ ID NO:115:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO:115:

UCCGUUAAGA GGACGGGAUA AACCUC 26

(2) INFORMATION FOR SEQ ID NO:116:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (xi) SEQUENCE DESCRIPTION: SEQ ID NO:116:

UUCCGUUUUC AGUCGGGAAA AACUGAA 27

(2) INFORMATION FOR SEQ ID NO:117:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO:117:

UUCCGAGGCC GAACGGGAAA ACCGGC 26

(2) INFORMATION FOR SEQ ID NO:118:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO:118:

ACCAGAGGCC CAACUGGUAA ACGGGC 26

(2) INFORMATION FOR SEQ ID NO:119:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO:119:

UCCGAAGCUC AACGGGAUAA UGAGC 25

(2) INFORMATION FOR SEQ ID NO:120:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear ( x i ) SEQUENCE DESCRIPTION: SEQ ID NO:120:

UCCGAACUCG ACGGGAUAAC GAG						23

( 2 ) INFORMATION FOR SEQ ID NO:121:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:121:

UCCGUAGGAG GCGGGAUAUC UCC						23

( 2 ) INFORMATION FOR SEQ ID NO:122:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:122:

UCCGUGCCGG CGGGAUAUCG GCG						23

( 2 ) INFORMATION FOR SEQ ID NO:123:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:123:

UCCGACUCGC GGGAUAACGA G							21

( 2 ) INFORMATION FOR SEQ ID NO:124:

( i ) SEQUENCE CHARACTERISTICS:
        ( A ) LENGTH: 19 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:124:

UUCGAACAAG CGGAACAUG							19

( 2 ) INFORMATION FOR SEQ ID NO:125:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:125:

UCCGUUCUUG AUCAUCGGGA CAAAUGAUC					29

( 2 ) INFORMATION FOR SEQ ID NO:126:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:126:

```
CCGUUACUCC UCGGGAUAAA GGAG                                              24
```

(2) INFORMATION FOR SEQ ID NO:127:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO:127:

```
CCGACGCCAA CGGGAGAAUG GC                                                22
```

(2) INFORMATION FOR SEQ ID NO:128:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO:128:

```
CCGUUAUCAU AGAUCGGGAC AAAUCUAUGA                                        30
```

(2) INFORMATION FOR SEQ ID NO:129:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO:129:

```
CCCAAGCCAA AGGGGAUAAU GCGGC                                             25
```

(2) INFORMATION FOR SEQ ID NO:130:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO:130:

```
CCCAAGCGCA GGGGAGAAGC GC                                                22
```

(2) INFORMATION FOR SEQ ID NO:131:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO:131:

```
CCUAGGUGAU AAAAGGGAGA ACAC                                              24
```

(2) INFORMATION FOR SEQ ID NO:132:

(i) SEQUENCE CHARACTERISTICS:
        (A) LENGTH: 93 nucleotides
        (B) TYPE: nucleic acid
        (C) STRANDEDNESS: single
        (D) TOPOLOGY: linear (xi) SEQUENCE DESCRIPTION: SEQ ID NO:132:

```
GGGAGCCAAC ACCACAAUUC CAAUCAAGNN NNNNNNNNN NNNNNNNNN                     50
```

NNNNNNNNN AUCUAUGAAA GAAUUUUAUA UCUCUAUUGA AAC 93

(2) INFORMATION FOR SEQ ID NO:133:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:133:

UCAAGAAUAU AUCCGAACUC GACGGGAUAA CGAGAAGAUC U 41

(2) INFORMATION FOR SEQ ID NO:134:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:134:

UCAAGAAUAU AUCCGAACUC GACGGGAUAA CGAGAAGAGC U 41

(2) INFORMATION FOR SEQ ID NO:135:

(i) SEQUENCE CHARACTERISTICS:
        (A) LENGTH: 43 nucleotides
        (B) TYPE: nucleic acid
        (C) STRANDEDNESS: single
        (D) TOPOLOGY: linear (xi) SEQUENCE DESCRIPTION: SEQ ID NO:135:

UCAAGCAAAU AUAUCCGAAC UCGACGGGAU AACGAGAAGA GCU 43

(2) INFORMATION FOR SEQ ID NO:136:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:136:

UCAAGAACAU AUCCGAACUC GACGGGAUAA CGAGAAGAGC U 41

(2) INFORMATION FOR SEQ ID NO:137:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:137:

UCAAGAAUAU AUCCGAACUC GACGGGGUAA CGAGAAGAGC U 41

(2) INFORMATION FOR SEQ ID NO:138:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:138:

UCAAGAAUAU AUCCGAACUC GACGGGAUAA CGAGAAGAGC U 41

( 2 ) INFORMATION FOR SEQ ID NO:139:

( i ) SEQUENCE CHARACTERISTICS:
    ( A ) LENGTH: 41 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:139:

UCAAGAAUAU AUCCGAACUC GACGGGAUAA CGAGAACACC U    41

( 2 ) INFORMATION FOR SEQ ID NO:140:

( i ) SEQUENCE CHARACTERISTICS:
    ( A ) LENGTH: 41 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:140:

UCAAGAAUAA AUCCGAACUC GACGGGAUAA CGAGAAGAGC U    41

( 2 ) INFORMATION FOR SEQ ID NO:141:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:141:

UCAAGGUAUA UAUCCGAACU CGACGGGAUA ACGAGAAGAG CU    42

( 2 ) INFORMATION FOR SEQ ID NO:142:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:142:

UCAAGAAUAU AUCCGAACUC GACGGGAUAA CGAGAAAGAG CU    42

( 2 ) INFORMATION FOR SEQ ID NO:143:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:143:

UCAAGAAUAU ACUCCGAACU CGACGGGAUA ACGAGAAGAG CU    42

( 2 ) INFORMATION FOR SEQ ID NO:144:

( i ) SEQUENCE CHARACTERISTICS:
    ( A ) LENGTH: 38 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:144:

UCAAGUACCU AGGUGAUAAA AGGGAGAACA CGUGAACU    38

( 2 ) INFORMATION FOR SEQ ID NO:145:

( i ) SEQUENCE CHARACTERISTICS:
  ( A ) LENGTH: 39 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:145:

UCAAGUACCU AGGUGAUAAA AGGGAGAACA CGUGUGACU 39

( 2 ) INFORMATION FOR SEQ ID NO:146:

( i ) SEQUENCE CHARACTERISTICS:
    ( A ) LENGTH: 39 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:146:

UCAAGUACCU AGGUGAUAAA AGGGAGAACA CAUGAGACU 39

( 2 ) INFORMATION FOR SEQ ID NO:147:

( i ) SEQUENCE CHARACTERISTICS:
    ( A ) LENGTH: 39 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:147:

UCAAGUACCU AGGUGAUAAA AGGGAGAACA CGUGAGACU 39

( 2 ) INFORMATION FOR SEQ ID NO:148:

( i ) SEQUENCE CHARACTERISTICS:
    ( A ) LENGTH: 41 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:148:

UCAAGUUAAA CAUAAUCCGU GAUCUUUCAC ACGGGAGAUC U 41

( 2 ) INFORMATION FOR SEQ ID NO:149:

( i ) SEQUENCE CHARACTERISTICS:
    ( A ) LENGTH: 41 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:149:

UCAAGUUAAA CAUAAUCCGU GAUCUUUCAC ACGGGAGACC U 41

( 2 ) INFORMATION FOR SEQ ID NO:150:

( i ) SEQUENCE CHARACTERISTICS:
    ( A ) LENGTH: 41 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:150:

UCAAGUUAAA CAUAAUCCGU GAUCUUUCAC ACGGAAGAAC U 41

( 2 ) INFORMATION FOR SEQ ID NO:151:

( i ) SEQUENCE CHARACTERISTICS:

(A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:151:

UCAAGUAGAU AUCCGAAGCU CAACGGGAUA AUGAGCAUCU                40

(2) INFORMATION FOR SEQ ID NO:152:

(i) SEQUENCE CHARACTERISTICS:
        (A) LENGTH: 42 nucleotides
        (B) TYPE: nucleic acid
        (C) STRANDEDNESS: single
        (D) TOPOLOGY: linear (xi) SEQUENCE DESCRIPTION: SEQ ID NO:152:

UCAAGCAAAU AUAUCCGAAG CUCAACGGGA UAAUGAGCAU CU             42

(2) INFORMATION FOR SEQ ID NO:153:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:153:

UCAAGUAGAU AUCCGAAGCU CAACGGGAUA AUGAGCGUCU                40

(2) INFORMATION FOR SEQ ID NO:154:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:154:

UCAAGAAGAU AUCCGAAGCU CAACGGGAUA AUGAGCAUCU                40

(2) INFORMATION FOR SEQ ID NO:155:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:155:

UCAAGUAAUA UAUCCGAAGC UCAUCGGGAU AAUGAGCAUC U              41

(2) INFORMATION FOR SEQ ID NO:156:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:156:

UCAAGAUAGU AUCCGUUCUU GAUCAUCGGG ACAAAUGAUC U              41

(2) INFORMATION FOR SEQ ID NO:157:

(i) SEQUENCE CHARACTERISTICS:
        (A) LENGTH: 41 nucleotides
        (B) TYPE: nucleic acid (C) STRANDEDNESS: single
(D) TOPOLOGY: linear (xi) SEQUENCE DESCRIPTION: SEQ ID NO:157:

UCAAGACAGU AUCCGUUCUU GAUCAUCGGG ACAAAUGAUC U 41

(2) INFORMATION FOR SEQ ID NO:158:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:158:

UCAAGUUAGU AUCCGUUCUU GAUCAUCGGG ACAAAUGAUC U 41

(2) INFORMATION FOR SEQ ID NO:159:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:159:

UCAAGAUAGU AUCCAUUCUU GAUCAUCGGG ACAAAUGAUC U 41

(2) INFORMATION FOR SEQ ID NO:160:

(i) SEQUENCE CHARACTERISTICS:
(A) LENGTH: 39 nucleotides
(B) TYPE: nucleic acid
(C) STRANDEDNESS: single
(D) TOPOLOGY: linear (xi) SEQUENCE DESCRIPTION: SEQ ID NO:160:

UCAAGUGAAC UUAACCGUUA UCAUAGAUCG GGACAAACU 39

(2) INFORMATION FOR SEQ ID NO:161:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:161:

UCAAGUGAAA CUUAACCGUU AUCAUAGAUC GGGACAAAUC U 41

(2) INFORMATION FOR SEQ ID NO:162:

(i) SEQUENCE CHARACTERISTICS:
(A) LENGTH: 40 nucleotides
(B) TYPE: nucleic acid
(C) STRANDEDNESS: single
(D) TOPOLOGY: linear (xi) SEQUENCE DESCRIPTION: SEQ ID NO:162:

UCAAGUGAAC UUAACCGUUA UCAUAGAUCG GACAAAUCU 40

(2) INFORMATION FOR SEQ ID NO:163:

(i) SEQUENCE CHARACTERISTICS:
(A) LENGTH: 41 nucleotides
(B) TYPE: nucleic acid
(C) STRANDEDNESS: single
(D) TOPOLOGY: linear ( x i ) SEQUENCE DESCRIPTION: SEQ ID NO:163:

UCAAGUGAAA CUUAACCGUU AUCAUAGAUC GUGACAAAUC U 41

( 2 ) INFORMATION FOR SEQ ID NO:164:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:164:

UCAAGAUAUG AUCCGUAAGA GGACGGGAUA AACCUCAACU 40

( 2 ) INFORMATION FOR SEQ ID NO:165:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:165:

UCAAGAUAUG UAUCCGUAAG AGGACGGGAU AAACCUCGAC U 41

( 2 ) INFORMATION FOR SEQ ID NO:166:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:166:

UCAAGGGGUA UUGAGAUAUU CCGAUGUCCU AUGCUGUACC U 41

( 2 ) INFORMATION FOR SEQ ID NO:167:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:167:

UCAAGGUUUC CGAAAGAAAU CGGGAAAACU GUCU 34

( 2 ) INFORMATION FOR SEQ ID NO:168:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:168:

UCAAGUAAAU GAGUCCGUAG GAGGCGGGAU AUCUCCAACU 40

( 2 ) INFORMATION FOR SEQ ID NO:169:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:169:

UCAAGUCAUA UUACCGUUAC UCCUCGGGAU AAAGGAGAUC U					41

( 2 ) INFORMATION FOR SEQ ID NO:170:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:170:

UCAAGAAUAA UCCGACUCGC GGGAUAACGA GAAGAGCU					38

( 2 ) INFORMATION FOR SEQ ID NO:171:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:171:

UCAAGGAUAA GUGCAGGAAU AUCAAUGAGG CAUCCAAACC U					41

( 2 ) INFORMATION FOR SEQ ID NO:172:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:172:

UCAAGAUGAG AUAAAGUACC AAUCGAACCU AUCUAAUACG ACU					43

( 2 ) INFORMATION FOR SEQ ID NO:173:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:173:

UCAAGACCCA UUUAUUGCUA CAAUAAUCCU UGACCUCAUC U					41

( 2 ) INFORMATION FOR SEQ ID NO:174:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:174:

UCAAGUAAUA CGAUAUACUA AUGAAGCCUA AUCUCGAUCU					40

( 2 ) INFORMATION FOR SEQ ID NO:175:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:175:

UCAAGAACGA UCAUCGAUAU CUCUUCCGAU CCGUUUGUCU					40

( 2 ) INFORMATION FOR SEQ ID NO:176:

( i ) SEQUENCE CHARACTERISTICS:
        ( A ) LENGTH: 39 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:176:

UCAAGACGAU AGAACAAUCA UCUCCUACGA CGAUGCACU　　　　　　　　　　　39

( 2 ) INFORMATION FOR SEQ ID NO:177:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:177:

UCAAGAUAAU CAUGCAGGAU CAUUGAUCUC UUGUGCUAUC U　　　　　　　　41

( 2 ) INFORMATION FOR SEQ ID NO:178:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:178:

UCAAGAGUGA AGAUGUAAGU GCUUAUCUCU UGGGACACAU CU　　　　　　　42

( 2 ) INFORMATION FOR SEQ ID NO:179:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:179:

UCAAGCAACA UUCUAUCAAG UAAAGUCACA UGAUAUCU　　　　　　　　　38

( 2 ) INFORMATION FOR SEQ ID NO:180:

( i ) SEQUENCE CHARACTERISTICS:
        ( A ) LENGTH: 39 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:180:

UCAAGGAUGU AUUACGAUUA CUCUAUACUG CCUGCAUCU　　　　　　　　　39

( 2 ) INFORMATION FOR SEQ ID NO:181:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:181:

UCAAGGGAUG AAAAUAGUUC CUAGUCUCAU UACGACCACU　　　　　　　　40

( 2 ) INFORMATION FOR SEQ ID NO:182:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:182:

UCAAGUAGUG UGAUAAUGAA UGGGUUUAUC GUAUGUGGCC U 41

( 2 ) INFORMATION FOR SEQ ID NO:183:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:183:

UCAAGAAUUC CGUUUUCAGU CGGGAAAAAC UGAACAAUCU 40

( 2 ) INFORMATION FOR SEQ ID NO:184:

( i ) SEQUENCE CHARACTERISTICS:
        ( A ) LENGTH: 90 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:184:

GGGAGCAUCA GACUUUUAAU CUGACAAUCA AGNNTTCCGN NNNNNNCGG 50

GAAAANNNC UAUGAAAGAA UUUUAUAUCU CUAUUGAAAC 90

( 2 ) INFORMATION FOR SEQ ID NO:185:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:185:

TCAAGTATTC CGAAGCTCAA CGGGAAAATG AGCTA 35

( 2 ) INFORMATION FOR SEQ ID NO:186:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:186:

TCAAGTATTC CGAAGCTTGA CGGGAAAATA AGCTA 35

( 2 ) INFORMATION FOR SEQ ID NO:187:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:187:

TCAAGGATTC CGAAGTTCAA CGGGAAAATG AACTA 35

( 2 ) INFORMATION FOR SEQ ID NO:188:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:188:

TCAAGAGTTC CGAAGGTTAA CGGGAAAATG ACCTA 35

( 2 ) INFORMATION FOR SEQ ID NO:189:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:189:

TCAAGGATTC CGAAGTGTAA CGGGAAAATG CACTA 35

( 2 ) INFORMATION FOR SEQ ID NO:190:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:190:

TCAAGTATTC CGAGGTGCCA CGGGAAAAGG CACTA 35

( 2 ) INFORMATION FOR SEQ ID NO:191:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:191:

TCAAGTATTC CGAAGGGTAA CGGGAAAATG CCCTA 35

( 2 ) INFORMATION FOR SEQ ID NO:192:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:192:

TCAAGTATTC CGAAGTACAA CGGGAAAACG TACTA 35

( 2 ) INFORMATION FOR SEQ ID NO:193:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:193:

TCAAGGATTC CGAAGTGTAA CGGGAAAACG CACTA 35

( 2 ) INFORMATION FOR SEQ ID NO:194:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:194:

TCAAGGATTC CGAAGCATAA CGGGAAAACA TGCTA 35

( 2 ) INFORMATION FOR SEQ ID NO:195:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:195:

TCAGGGATTC CGAAGTGTAA CGGGAAAAAG CACTA 35

( 2 ) INFORMATION FOR SEQ ID NO:196:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:196:

TCAAGTATTC CGAGGTGTGA CGGGAAAAGA CACTA 35

( 2 ) INFORMATION FOR SEQ ID NO:197:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:197:

TCAAGTATTC CGAAGGGTAA CGGGAAAATG ACCTA 35

( 2 ) INFORMATION FOR SEQ ID NO:198:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:198:

TCAAGTGTTC CGAGAGGCAA CGGGAAAAGA GCCTA 35

( 2 ) INFORMATION FOR SEQ ID NO:199:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:199:

TCAAGTATTC CGAAGGTGAA CGGGAAAATA CACTA 35

( 2 ) INFORMATION FOR SEQ ID NO:200:

( i ) SEQUENCE CHARACTERISTICS:
    ( A ) LENGTH: 35 nucleotides ( B ) TYPE: nucleic acid
( C ) STRANDEDNESS: single
( D ) TOPOLOGY: linear ( x i ) SEQUENCE DESCRIPTION: SEQ ID NO:200:

TCAAGAGTTC CGAAAGTCGA CGGGAAAATA GACTA    35

( 2 ) INFORMATION FOR SEQ ID NO:201:

( i ) SEQUENCE CHARACTERISTICS:
( A ) LENGTH: 35 nucleotides
( B ) TYPE: nucleic acid
( C ) STRANDEDNESS: single
( D ) TOPOLOGY: linear ( x i ) SEQUENCE DESCRIPTION: SEQ ID NO:201:

TCAAGATTTC CGAGAGACAA CGGGAAAAGA GTCTA    35

( 2 ) INFORMATION FOR SEQ ID NO:202:

( i ) SEQUENCE CHARACTERISTICS:
( A ) LENGTH: 35 nucleotides
( B ) TYPE: nucleic acid
( C ) STRANDEDNESS: single
( D ) TOPOLOGY: linear ( x i ) SEQUENCE DESCRIPTION: SEQ ID NO:202:

TCAAGATTTC CGATGTGCAA CGGGAAAATG CACTA    35

( 2 ) INFORMATION FOR SEQ ID NO:203:

( i ) SEQUENCE CHARACTERISTICS:
( A ) LENGTH: 35 nucleotides
( B ) TYPE: nucleic acid
( C ) STRANDEDNESS: single
( D ) TOPOLOGY: linear ( x i ) SEQUENCE DESCRIPTION: SEQ ID NO:203:

TCAAGTATTC CGACGTAACA CGGGAAAAGT TACTA    35

( 2 ) INFORMATION FOR SEQ ID NO:204:

( i ) SEQUENCE CHARACTERISTICS:
( A ) LENGTH: 35 nucleotides
( B ) TYPE: nucleic acid
( C ) STRANDEDNESS: single
( D ) TOPOLOGY: linear ( x i ) SEQUENCE DESCRIPTION: SEQ ID NO:204:

TCAAGATTTC CGACGCACAA CGGGAAAATG TGCTA    35

( 2 ) INFORMATION FOR SEQ ID NO:205:

( i ) SEQUENCE CHARACTERISTICS:
( A ) LENGTH: 35 nucleotides
( B ) TYPE: nucleic acid
( C ) STRANDEDNESS: single
( D ) TOPOLOGY: linear ( x i ) SEQUENCE DESCRIPTION: SEQ ID NO:205:

TCAAGTATTC CGATGTCTAA CGGGAAAATA GGCTA    35

( 2 ) INFORMATION FOR SEQ ID NO:206:

( i ) SEQUENCE CHARACTERISTICS:
( A ) LENGTH: 35 nucleotides
( B ) TYPE: nucleic acid
( C ) STRANDEDNESS: single (D) TOPOLOGY: linear (xi) SEQUENCE DESCRIPTION: SEQ ID NO:206:

TCAAGGGTTC CGATGCCCAA CGGGAAAAGG GGCTA 35

(2) INFORMATION FOR SEQ ID NO:207:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:207:

TCAAGAATTC CGACGACGAA CGGGAAAAAC GTCTA 35

(2) INFORMATION FOR SEQ ID NO:208:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:208:

TCAAGTATTC CGATGTACAA CGGGAAAAAG TACTA 35

(2) INFORMATION FOR SEQ ID NO:209:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:209:

TCCAGCGTTC CGTAAGTGGA CGGGAAAAAC CACTA 35

(2) INFORMATION FOR SEQ ID NO:210:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:210:

TCAAGAGTTC CGTAAGGCCA CGGGAAAAAG GTCTA 35

(2) INFORMATION FOR SEQ ID NO:211:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:211:

TCAAGGATTC CGAAAGGTAA CGGGAAAAAT GCCTA 35

(2) INFORMATION FOR SEQ ID NO:212:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:212:

TCAAGAATTC CGCTAGCCCA CGGGAAAAGG GCCTA    35

(2) INFORMATION FOR SEQ ID NO:213:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO:213:

TCAAGAATTC GTTAGTGTAC GGGAAAAAAC ACTA    34

(2) INFORMATION FOR SEQ ID NO:214:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:214:

TCAAGCGTTC CGATGGCTAA CGGGAAAAAT AGCTA    35

(2) INFORMATION FOR SEQ ID NO:215:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:215:

TCAAGGATTC CGTTTGTGCA CGGGAAAAGG CACTA    35

(2) INFORMATION FOR SEQ ID NO:216:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO:216:

TCAAGAATCC GTTTGCACAC GGGAAAACGT GCTA    34

(2) INFORMATION FOR SEQ ID NO:217:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:217:

TCAGGAATCC GAGAAGCTAC GGGAAAAAGC GACTA    35

(2) INFORMATION FOR SEQ ID NO:218:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO:218:

TCAAGATTTC CGAGGTCCGA CGGGAAAATG GTCTA 35

( 2 ) INFORMATION FOR SEQ ID NO:219:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:219:

TCAAGTATTC CGAAGGAAAA CGGGAAAACC ACCTA 35

( 2 ) INFORMATION FOR SEQ ID NO:220:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:220:

TCAAGTGTTC CGAAGGAAAA CGGGAAAACC ACCTA 35

( 2 ) INFORMATION FOR SEQ ID NO:221:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:221:

TCAAGAATTC CGTAAGGGGT CGGGAAAAAC CCTAU 35

( 2 ) INFORMATION FOR SEQ ID NO:222:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:222:

TCAAGGATTC CGTATGTCCT CGGGAAAAAG GACTA 35

( 2 ) INFORMATION FOR SEQ ID NO:223:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:223:

TCAAGAGTTC CGAAAGGTAA CGGGAAAATT ACCTA 35

( 2 ) INFORMATION FOR SEQ ID NO:224:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:224:

TCAAGTATTC CGATAGTCAA CGGGAAAAGC GACTA 35

( 2 ) INFORMATION FOR SEQ ID NO:225:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:225:

TCAAGTATTC CGAGGTGTTA CGGGAAAACA CGCTA　　　　　　　　　　　　35

( 2 ) INFORMATION FOR SEQ ID NO:226:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:226:

TCAAGAATTC CGTATGTGAT CGGGAAAAAC CACTA　　　　　　　　　　　　35

( 2 ) INFORMATION FOR SEQ ID NO:227:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:227:

TCAAGGATTC CGATGTACAA CGGGAAAACT GTCTA　　　　　　　　　　　　35

( 2 ) INFORMATION FOR SEQ ID NO:228:

( i ) SEQUENCE CHARACTERISTICS:
        ( A ) LENGTH: 36 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:228:

TCAAGATTTC CGAAGGATAA CGGGAAAAAC CGACTA　　　　　　　　　　　　36

( 2 ) INFORMATION FOR SEQ ID NO:229:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:229:

TCAAGAATTC CGAAGCGTAA CGGGAAAACA TACTA　　　　　　　　　　　　35

( 2 ) INFORMATION FOR SEQ ID NO:230:

( i ) SEQUENCE CHARACTERISTICS:
        ( A ) LENGTH: 93 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:230:

GGGAGCCAAC ACCACAAUUC CAAUCAAGNN NNNNNNNNN NNNNNNNNN　　　　　　50

NNNNNNNNN AUCUAUGAAA GAAUUUAUA UCUCUAUUGA AAC　　　　　　　　　　93

( 2 ) INFORMATION FOR SEQ ID NO:231:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:231:

CAGAGAUAUC ACUUCUGUUC ACCAUCAGGG GACUAUGAAA GA         42

( 2 ) INFORMATION FOR SEQ ID NO:232:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:232:

AUAUAAGUAA UGGAUGCGCA CCAUCAGGGC GUAUCUAUGA AAGA         44

( 2 ) INFORMATION FOR SEQ ID NO:233:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:233:

GGAAUAAGUG CUUUCGUCGA UCACCAUCAG GGAUCUAUGA AAGA         44

( 2 ) INFORMATION FOR SEQ ID NO:234:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:234:

UGGAGUAUAA ACCUUUAUGG UCACCAUCAG GGAUCUAUGA AAGA         44

( 2 ) INFORMATION FOR SEQ ID NO:235:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:235:

UCAGAGAUAG CUCAUAGGAC ACCAUCAGGG UCUAUGAAAG A         41

( 2 ) INFORMATION FOR SEQ ID NO:236:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:236:

CUGAGAUAUA UGACAGAGUC CACCAUCAGG GAUCUAUGAA AGA         43

( 2 ) INFORMATION FOR SEQ ID NO:237:

( i ) SEQUENCE CHARACTERISTICS:
    ( A ) LENGTH: 44 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:237:

GGAUUAAUAU GUCUGCAUGA UCACCAUCAG GGAUCUAUGA AAGA      4 4

( 2 ) INFORMATION FOR SEQ ID NO:238:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:238:

GGGAGAUUCU UAGUACUCAC CAUCAGGGGG CACUAUGAAA GA      4 2

( 2 ) INFORMATION FOR SEQ ID NO:239:

( i ) SEQUENCE CHARACTERISTICS:
    ( A ) LENGTH: 43 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:239:

AAAUUAUCUU CGGAAUGCAC CAUCAGGGCA UGGCUAUGAA AGA      4 3

( 2 ) INFORMATION FOR SEQ ID NO:240:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:240:

GGGAGAUUCU UACUACUCAC CAUCAGGGGG CACUAUGAAA GA      4 2

( 2 ) INFORMATION FOR SEQ ID NO:241:

( i ) SEQUENCE CHARACTERISTICS:
    ( A ) LENGTH: 43 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:241:

GGAAUACUUU CUUUCGAUGC ACCAUCAGGG CGUCUAUGAA AGA      4 3

( 2 ) INFORMATION FOR SEQ ID NO:242:

( i ) SEQUENCE CHARACTERISTICS:
    ( A ) LENGTH: 44 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:242:

UCCAAUAGAG UUAGUAGUUG CACCAUCAGG GCAUCUAUGA AAGA      4 4

( 2 ) INFORMATION FOR SEQ ID NO:243:

( i ) SEQUENCE CHARACTERISTICS:

( A ) LENGTH: 43 nucleotides
( B ) TYPE: nucleic acid
( C ) STRANDEDNESS: single
( D ) TOPOLOGY: linear ( x i ) SEQUENCE DESCRIPTION: SEQ ID NO:243:

GUAUAGAUAG UUCUACUGAU CACGAUCACG GGUCUAUGAA AGA 43

( 2 ) INFORMATION FOR SEQ ID NO:244:

( i ) SEQUENCE CHARACTERISTICS:
( A ) LENGTH: 44 nucleotides
( B ) TYPE: nucleic acid
( C ) STRANDEDNESS: single
( D ) TOPOLOGY: linear ( x i ) SEQUENCE DESCRIPTION: SEQ ID NO:244:

GGAUAUGAUC UUAUGGUAUG CACGAUCACG GCAUCUAUGA AAGA 44

( 2 ) INFORMATION FOR SEQ ID NO:245:

( i ) SEQUENCE CHARACTERISTICS:
( A ) LENGTH: 44 nucleotides
( B ) TYPE: nucleic acid
( C ) STRANDEDNESS: single
( D ) TOPOLOGY: linear ( x i ) SEQUENCE DESCRIPTION: SEQ ID NO:245:

UUGUCUUUCA UGUAGUAAGC ACGAUCACGG CGACUAUGAA AAGA 44

( 2 ) INFORMATION FOR SEQ ID NO:246:

( i ) SEQUENCE CHARACTERISTICS:
( A ) LENGTH: 43 nucleotides
( B ) TYPE: nucleic acid
( C ) STRANDEDNESS: single
( D ) TOPOLOGY: linear ( x i ) SEQUENCE DESCRIPTION: SEQ ID NO:246:

AGAGCUAGUU CUUGUUUAAG ACACGAUCAC GGUCUAUGAA AGA 43

( 2 ) INFORMATION FOR SEQ ID NO:247:

( i ) SEQUENCE CHARACTERISTICS:
( A ) LENGTH: 44 nucleotides
( B ) TYPE: nucleic acid
( C ) STRANDEDNESS: single
( D ) TOPOLOGY: linear ( x i ) SEQUENCE DESCRIPTION: SEQ ID NO:247:

ACGAGAUUUA UUUAGAUGUC ACGAUCACGG GCACCUAUGA AAGA 44

( 2 ) INFORMATION FOR SEQ ID NO:248:

( i ) SEQUENCE CHARACTERISTICS:
( A ) LENGTH: 44 nucleotides
( B ) TYPE: nucleic acid
( C ) STRANDEDNESS: single
( D ) TOPOLOGY: linear ( x i ) SEQUENCE DESCRIPTION: SEQ ID NO:248:

UAAUUGAUAC UUGCAGAGGA UCACCUGCU CGAUCUAUGA AAGA 44

( 2 ) INFORMATION FOR SEQ ID NO:249:

( i ) SEQUENCE CHARACTERISTICS:
( A ) LENGTH: 43 nucleotides
( B ) TYPE: nucleic acid (C) STRANDEDNESS: single
(D) TOPOLOGY: linear (xi) SEQUENCE DESCRIPTION: SEQ ID NO:249:

AGAGGACUCA UUAGAGGAUC ACCCUAGUGC GGUCUAUGAA AGA    43

(2) INFORMATION FOR SEQ ID NO:250:

(i) SEQUENCE CHARACTERISTICS:
  (A) LENGTH: 44 nucleotides
  (B) TYPE: nucleic acid
  (C) STRANDEDNESS: single
  (D) TOPOLOGY: linear (xi) SEQUENCE DESCRIPTION: SEQ ID NO:250:

GAGAUAUCAU AAUUCAUUGU UGAGCAUCAG CCAUCUAUGA AAGA    44

(2) INFORMATION FOR SEQ ID NO:251:

(i) SEQUENCE CHARACTERISTICS:
  (A) LENGTH: 43 nucleotides
  (B) TYPE: nucleic acid
  (C) STRANDEDNESS: single
  (D) TOPOLOGY: linear (xi) SEQUENCE DESCRIPTION: SEQ ID NO:251:

UGUAUAGAGC AUCAGCCUAU ACAUUGCGUG GCACUAUGAA AGA    43

(2) INFORMATION FOR SEQ ID NO:252:

(i) SEQUENCE CHARACTERISTICS:
  (A) LENGTH: 40 nucleotides
  (B) TYPE: nucleic acid
  (C) STRANDEDNESS: single
  (D) TOPOLOGY: linear (xi) SEQUENCE DESCRIPTION: SEQ ID NO:252:

GAGAUCAAUA GUAAGGACCA UCAGGCCUGG CUAUGAAAGA    40

(2) INFORMATION FOR SEQ ID NO:253:

(i) SEQUENCE CHARACTERISTICS:
  (A) LENGTH: 44 nucleotides
  (B) TYPE: nucleic acid
  (C) STRANDEDNESS: single
  (D) TOPOLOGY: linear (xi) SEQUENCE DESCRIPTION: SEQ ID NO:253:

UGAGAUAUCU CUAUAGUGUG GAGCAUCAGC CAUCUAUGA AAGA    44

(2) INFORMATION FOR SEQ ID NO:254:

(i) SEQUENCE CHARACTERISTICS:
  (A) LENGTH: 40 nucleotides
  (B) TYPE: nucleic acid
  (C) STRANDEDNESS: single
  (D) TOPOLOGY: linear (xi) SEQUENCE DESCRIPTION: SEQ ID NO:254:

AUGAGAUAGA UCAUGCUCAG GAUCACCGGG CUAUGAAAGA    40

(2) INFORMATION FOR SEQ ID NO:255:

(i) SEQUENCE CHARACTERISTICS:
  (A) LENGTH: 42 nucleotides
  (B) TYPE: nucleic acid
  (C) STRANDEDNESS: single
  (D) TOPOLOGY: linear ( x i ) SEQUENCE DESCRIPTION: SEQ ID NO:255:

AGAGUAUUCU ACAUGAUUUG CAUCAUCUGG GCGUAUGAAA GA 42

( 2 ) INFORMATION FOR SEQ ID NO:256:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:256:

GGAUUAAUUC GUCUUUUGAG UGACGAUCAC GCACUAUGAA AGA 43

( 2 ) INFORMATION FOR SEQ ID NO:257:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:257:

AUUGCGUAAU GUUACCAUCA GGAACACCGC GUAUCUAUGA AAGA 44

( 2 ) INFORMATION FOR SEQ ID NO:258:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:258:

GAGUAAGAUA GCAUCAGCAU CUUGUUCCCG CCAUCUAUGA AAGA 44

( 2 ) INFORMATION FOR SEQ ID NO:259:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:259:

GCGUUAAUUU GGAUUAUAGA UCACCAACAG GGACCUAUGA AAGA 44

( 2 ) INFORMATION FOR SEQ ID NO:260:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:260:

GAGAUGUUUA GUACUUCAGC CACCAACAGG GGUCUAUGAA AGA 43

( 2 ) INFORMATION FOR SEQ ID NO:261:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:261:

```
GUCAUACUCU CUUUGUNNUG CACCAACAGG GCAUCUAUGA AAGA                      44
```

(2) INFORMATION FOR SEQ ID NO:262:

(i) SEQUENCE CHARACTERISTICS:
        (A) LENGTH: 43 nucleotides
        (B) TYPE: nucleic acid
        (C) STRANDEDNESS: single
        (D) TOPOLOGY: linear (xi) SEQUENCE DESCRIPTION: SEQ ID NO:262:

```
AUAGUAGAGG AACACCCUAC UAAGUCCCG CCACUAUGAA AGA                         43
```

(2) INFORMATION FOR SEQ ID NO:263:

(i) SEQUENCE CHARACTERISTICS:
        (A) LENGTH: 43 nucleotides
        (B) TYPE: nucleic acid
        (C) STRANDEDNESS: single
        (D) TOPOLOGY: linear (xi) SEQUENCE DESCRIPTION: SEQ ID NO:263:

```
CAACAGAGAU GAUAUCAGGA UGAGGACCAC CCAUCUAUGA GGA                        43
```

(2) INFORMATION FOR SEQ ID NO:264:

(i) SEQUENCE CHARACTERISTICS:
        (A) LENGTH: 44 nucleotides
        (B) TYPE: nucleic acid
        (C) STRANDEDNESS: single
        (D) TOPOLOGY: linear (xi) SEQUENCE DESCRIPTION: SEQ ID NO:264:

```
AGAUAUAAUU CUCCUCUUGA UGAGCACCAG CCAUCUAUGA AAGA                       44
```

(2) INFORMATION FOR SEQ ID NO:265:

(i) SEQUENCE CHARACTERISTICS:
        (A) LENGTH: 44 nucleotides
        (B) TYPE: nucleic acid
        (C) STRANDEDNESS: single
        (D) TOPOLOGY: linear (xi) SEQUENCE DESCRIPTION: SEQ ID NO:265:

```
UAGAGAUAUG AGAUAGUUGC ACCACCAGGG UGAUCUAUGA AAGA                       44
```

(2) INFORMATION FOR SEQ ID NO:266:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:266:

```
AUAUAGGAGA UAUUGUAGUC ACGAGCACGG GCUAUGAAAG A                          41
```

(2) INFORMATION FOR SEQ ID NO:267:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (xi) SEQUENCE DESCRIPTION: SEQ ID NO:267:

```
UGCGUCACUU AUUGGAACUC UGGGUGGCAC UAUGAAAGA                             39
```

( 2 ) INFORMATION FOR SEQ ID NO:268:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:268:

CUGGAGGAGA UUGUGUAAUC GCUUGAACUC CACUAUGAAA GA        4 2

( 2 ) INFORMATION FOR SEQ ID NO:269:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:269:

TCAAGATGAA GATACAGCTC CAGATGCTGG ACACATCT        3 8

( 2 ) INFORMATION FOR SEQ ID NO:270:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:270:

TCAAGGGATG AAGATACAGC TCTAGATGCT GGACACATCT        4 0

( 2 ) INFORMATION FOR SEQ ID NO:271:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:271:

TCAAGGAGAT GAAGATACAG CTCTAGATGC TGGACACATC T        4 1

( 2 ) INFORMATION FOR SEQ ID NO:272:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:272:

TCAAGCGAGA TGAAGATACA GCTCCAGATG CTGGACACAT CT        4 2

( 2 ) INFORMATION FOR SEQ ID NO:273:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:273:

TCAAGGAGAT GAAGATACAG CTCTGGATGC TGGACACATC T        4 1

(2) INFORMATION FOR SEQ ID NO:274:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:274:

TCAAGCTTGA GATACAGATT TCTGATTCTG GCTCGCTATC T      41

(2) INFORMATION FOR SEQ ID NO:275:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:275:

TCAAGATGGA CTCGGTATCA AACGACCTTG AGACACATCT      40

(2) INFORMATION FOR SEQ ID NO:276:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:276:

TCAAGATGGA CTCGGTATCA AACGGCCTTG AGACACATCT      40

(2) INFORMATION FOR SEQ ID NO:277:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:277:

TCAAGATGGC TGGAGATACA AACTATTTGG CTCGCCATCT      40

(2) INFORMATION FOR SEQ ID NO:278:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:278:

TCAAGATGGC TGGAGATACA AAACTATTTG GCTCGCCATC T      41

(2) INFORMATION FOR SEQ ID NO:279:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO:279:

TCAAGATGGC TGGAGATACA AACTGTTTGG CTCGCCATCT      40

(2) INFORMATION FOR SEQ ID NO:280:

( i ) SEQUENCE CHARACTERISTICS:
    ( A ) LENGTH: 41 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:280:

TCAAGAAGCC TTGAGATACA CTATATAGTG GACCGGCATC T          41

( 2 ) INFORMATION FOR SEQ ID NO:281:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:281:

TCAAGGGTGC ATTGAGAAAC ACGTTTGTGG ACTCTGTATC T          41

( 2 ) INFORMATION FOR SEQ ID NO:282:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:282:

TCAAGAGTGC ATTGAGAAAC ACGTTTGTGG ACTCGGTGAT CT          42

( 2 ) INFORMATION FOR SEQ ID NO:283:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:283:

TCAAGAGCGA AGATACAGAA GACAATACTG GACACGCATC T          41

( 2 ) INFORMATION FOR SEQ ID NO:284:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:284:

TCAAGAGCGA AGATACAGAA GACAATACTG GACACACTAT CT          42

( 2 ) INFORMATION FOR SEQ ID NO:285:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:285:

TCAAGGGGAC TCTTTTCAAT GATCCTTTAA CCAGTCGATC T          41

( 2 ) INFORMATION FOR SEQ ID NO:286:

( i ) SEQUENCE CHARACTERISTICS:
        ( A ) LENGTH: 41 nucleotides (B) TYPE: nucleic acid
(C) STRANDEDNESS: single
(D) TOPOLOGY: linear (xi) SEQUENCE DESCRIPTION: SEQ ID NO:286:

TCAAGAAGAG ACATTCGAAT GATCCCTTAA CCGGTTGATC T　　　　41

(2) INFORMATION FOR SEQ ID NO:287:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:287:

TCAAGAAGAG ACACTCGAAT GATCCCTTAA CCGGTTGATC T　　　　41

(2) INFORMATION FOR SEQ ID NO:288:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:288:

TCAAGCACGC ATGACACAGA TAAACTGGAC TACGTGCATC T　　　　41

(2) INFORMATION FOR SEQ ID NO:289:

(i) SEQUENCE CHARACTERISTICS:
(A) LENGTH: 40 nucleotides
(B) TYPE: nucleic acid
(C) STRANDEDNESS: single
(D) TOPOLOGY: linear (xi) SEQUENCE DESCRIPTION: SEQ ID NO:289:

TCAAGACACC TTGAGGTACT CTTAACAGGC TCGGTGATCT　　　　40

(2) INFORMATION FOR SEQ ID NO:290:

(i) SEQUENCE CHARACTERISTICS:
(A) LENGTH: 41 nucleotides
(B) TYPE: nucleic acid
(C) STRANDEDNESS: single
(D) TOPOLOGY: linear (xi) SEQUENCE DESCRIPTION: SEQ ID NO:290:

TCAAGTTGAG ATACCTGAAC TTGGGACTCC TTGGTTGATC T　　　　41

(2) INFORMATION FOR SEQ ID NO:291:

(i) SEQUENCE CHARACTERISTICS:
(A) LENGTH: 42 nucleotides
(B) TYPE: nucleic acid
(C) STRANDEDNESS: single
(D) TOPOLOGY: linear (xi) SEQUENCE DESCRIPTION: SEQ ID NO:291:

TCAAGGGATC TTGAGATACA CACGAATGAG TGGACTCGAT CT　　　　42

(2) INFORMATION FOR SEQ ID NO:292:

(i) SEQUENCE CHARACTERISTICS:
(A) LENGTH: 41 nucleotides
(B) TYPE: nucleic acid
(C) STRANDEDNESS: single (D) TOPOLOGY: linear (xi) SEQUENCE DESCRIPTION: SEQ ID NO:292:

TCAAGATCGA ATTGAGAAAC ACTAACTGGC CTCTTTGATC T 41

(2) INFORMATION FOR SEQ ID NO:293:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:293:

TCAAGGCAGC AGATACAGGA TATACTGGAC ACTGCCGATC T 41

(2) INFORMATION FOR SEQ ID NO:294:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:294:

TCAAGGGATA TAACGAGTGA TCCAGGTAAC TCTGTTGATC T 41

(2) INFORMATION FOR SEQ ID NO:295:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:295:

TCAAGGTGGA TTTGAGATAC ACGGAAGTGG ACTCTCCATC T 41

(2) INFORMATION FOR SEQ ID NO:296:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:296:

TCAAGAGATA ATACAATGAT CCTGCTCACT ACAGTTGATC T 41

(2) INFORMATION FOR SEQ ID NO:297:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO:297:

TCAAGGGAGG TATACAGAAT GATCCGGTTG CTCGTTGATC T 41

(2) INFORMATION FOR SEQ ID NO:298:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear ( x i ) SEQUENCE DESCRIPTION: SEQ ID NO:298:

TCAAGAGAAG AATAGTTGAA ACAGATCAAA CCTGGACATC T 41

( 2 ) INFORMATION FOR SEQ ID NO: 299:

( i ) SEQUENCE CHARACTERISTICS:
        ( A ) LENGTH: 46 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:299:

AAGGGAUCUU GAGAUACACA CGAAUGAGUG GACUCGAUCU AUGAAA 46

( 2 ) INFORMATION FOR SEQ ID NO:300:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:300:

AGGUGGAUUU GAGAUACACG GAAGUGGACU CUCCAUCUAU GA 42

( 2 ) INFORMATION FOR SEQ ID NO:301:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:301:

AGGGUGCAUU GAGAAACACG UUUGUGGACU CUGUAUCUAU GA 42

( 2 ) INFORMATION FOR SEQ ID NO:302:

( i ) SEQUENCE CHARACTERISTICS:
        ( A ) LENGTH: 37 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:302:

CGACCUUGAG ACACAUCUAG AUGGACUCGG UAUCAAA 37

( 2 ) INFORMATION FOR SEQ ID NO:303:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:303:

AGAUCGAAUU GAGAAACACU AACUGGCCUC UUUGAUCUAU G 41

( 2 ) INFORMATION FOR SEQ ID NO:304:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:304:

CAAUCAAGUU GAGAUACCUG AACUUGGGAC UCCUUGGUUG AUC 43

( 2 ) INFORMATION FOR SEQ ID NO:305:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:305:

AAGAUGGCUG GAGAUACAAA ACUAUUUGGC UCGCCAUCUA UGA 43

( 2 ) INFORMATION FOR SEQ ID NO:306:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:306:

AAGAAGCCUU GAGAUACACU AUAUAGUGGA CCGGCAUCUA UGA 43

( 2 ) INFORMATION FOR SEQ ID NO:307:

( i ) SEQUENCE CHARACTERISTICS:
        ( A ) LENGTH: 47 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:307:

AAUCAAGCUU GAGAUACAGA UUUCUGAUUC UGGCUCGCUA UCUAUGA 47

( 2 ) INFORMATION FOR SEQ ID NO:308:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:308:

AAGACACCUU GAGGUACUCU UAACAGGCUC GGUGAUCUAU G 41

( 2 ) INFORMATION FOR SEQ ID NO:309:

( i ) SEQUENCE CHARACTERISTICS:
        ( A ) LENGTH: 45 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:309:

UCAAGGAGAU GAAGAUACAG CUCUAGAUGC UGGACACAUC UAUGA 45

( 2 ) INFORMATION FOR SEQ ID NO:310:

( i ) SEQUENCE CHARACTERISTICS:
        ( A ) LENGTH: 45 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:310:

AAUCAAGAGC GAAGAUACAG AAGACAAUAC UGGACACGCA UCUAU 45

( 2 ) INFORMATION FOR SEQ ID NO:311:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:311:

AAUCAAGGCA GCAGAUACAG GAUAUACUGG ACACUGCCGA UC        42

( 2 ) INFORMATION FOR SEQ ID NO:312:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:312:

GAGAAGAAUA GUUGAAACAG AUCAAACCUG GACAUCUAUG AAA        43

( 2 ) INFORMATION FOR SEQ ID NO:313:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:313:

AUCAAGCACG CAUGACACAG AUAAACUGGA CUACGUGCAU C        41

( 2 ) INFORMATION FOR SEQ ID NO:314:

( i ) SEQUENCE CHARACTERISTICS:
        ( A ) LENGTH: 67 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:314:

CAAUCAAGAG AUAAUACAAU GAUCCUGCUC ACUACAGUUG AUCUAUGAAA        50

GAAUUUUAUA UCUCUAU        67

( 2 ) INFORMATION FOR SEQ ID NO:315:

( i ) SEQUENCE CHARACTERISTICS:
        ( A ) LENGTH: 64 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:315:

UCAAGAAGAG ACAUUCGAAU GAUCCCUUAA CCGGUUGAUC UAUGAAAGAA        50

UUUUAUAUCU CUAU        64

( 2 ) INFORMATION FOR SEQ ID NO:316:

( i ) SEQUENCE CHARACTERISTICS:
        ( A ) LENGTH: 64 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:316:

```
UCAAGGGGAC UCUUUUCAAU GAUCCUUUAA CCAGUCGAUC UAUGAAAGAA        50

UUUUAUAUCU CUAU                                                64
```

( 2 ) INFORMATION FOR SEQ ID NO:317:

( i ) SEQUENCE CHARACTERISTICS:
        ( A ) LENGTH: 64 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:317:

```
UCAAGGGAGG UAUACAGAAU GAUCCGGUUG CUCGUUGAUC UAUGAAAGAA        50

UUUUAUAUCU CUAU                                                64
```

( 2 ) INFORMATION FOR SEQ ID NO:318:

( i ) SEQUENCE CHARACTERISTICS:
        ( A ) LENGTH: 66 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:318:

```
AAUCAAGGGA UAUAACGAGU GAUCCAGGUA ACUCUGUUGA UCUAUGAAAG        50

AAUUUUAUAU CUCUAU                                              66
```

( 2 ) INFORMATION FOR SEQ ID NO:319:

( i ) SEQUENCE CHARACTERISTICS:
        ( A ) LENGTH: 37 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:319:

```
GGAUCUUGAG AUACACACGA AUGAGUGGAC UCGAUCU                      37
```

( 2 ) INFORMATION FOR SEQ ID NO:320:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:320:

```
CAAUCAAGUU GAGAUACCUG AACUUGGGAC UCCUUGGUUG                   40
```

( 2 ) INFORMATION FOR SEQ ID NO:321:

( i ) SEQUENCE CHARACTERISTICS:
        ( A ) LENGTH: 37 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:321:

```
GGGUGCAUUG AGAAACACGU UUGUGGACUC UGUAUCU                      37
```

( 2 ) INFORMATION FOR SEQ ID NO:322:

( i ) SEQUENCE CHARACTERISTICS:
        ( A ) LENGTH: 29 nucleotides
        ( B ) TYPE: nucleic acid
        ( C ) STRANDEDNESS: single ( D ) TOPOLOGY: linear ( x i ) SEQUENCE DESCRIPTION: SEQ ID NO:322:

ACCUUGAGAC ACAUCUAGAU GGACUCGGU 29

( 2 ) INFORMATION FOR SEQ ID NO:323:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:323:

AGAUCGAAUU GAGAAACACU AACUGGCCUC UUUGAUCU 38

( 2 ) INFORMATION FOR SEQ ID NO:324:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:324:

AGCUUGAGAU ACAGAUUUCU GAUUCUGGCU CGCU 34

( 2 ) INFORMATION FOR SEQ ID NO:325:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:325:

CACCUUGAGG UACUCUUAAC AGGCUCGGUG 30

( 2 ) INFORMATION FOR SEQ ID NO:326:

( i ) SEQUENCE CHARACTERISTICS:
        ( A ) LENGTH: 37 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:326:

AGAUGGCUGG AGAUACAAAC UAUUUGGCUC GCCAUCU 37

( 2 ) INFORMATION FOR SEQ ID NO:327:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:327:

AGAAGCCUUG AGAUACACUA UAUAGUGGAC CGGCAUCU 38

( 2 ) INFORMATION FOR SEQ ID NO:328:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:328:

AGGUGGAUUU GAGAUACACG GAAGUGGACU CUCCAUCU 38

( 2 ) INFORMATION FOR SEQ ID NO:329:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:329:

AGAUGAAGAU ACAGCUCUAG AUGCUGGACA CAUCU 35

( 2 ) INFORMATION FOR SEQ ID NO:330:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:330:

AGAGCGAAGA UACAGAAGAC AAUACUGGAC ACGCAUCU 38

( 2 ) INFORMATION FOR SEQ ID NO:331:

( i ) SEQUENCE CHARACTERISTICS:
        ( A ) LENGTH: 32 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:331:

GGCAGCAGAU ACAGGAUAUA CUGGACACUG CC 32

( 2 ) INFORMATION FOR SEQ ID NO:332:

( i ) SEQUENCE CHARACTERISTICS:
        ( A ) LENGTH: 32 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:332:

AUAGUUGAAA CAGAUCAAAC CUGGACAUCU AU 32

( 2 ) INFORMATION FOR SEQ ID NO:333:

( i ) SEQUENCE CHARACTERISTICS:
        ( A ) LENGTH: 33 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:333:

GCACGCAUGA CACAGAUAAA CUGGACUACG UGC 33

( 2 ) INFORMATION FOR SEQ ID NO:334:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:334:

GACGCUGACG GUACAUGGGC GCAGCGUC 28

( 2 ) INFORMATION FOR SEQ ID NO:335:

( i ) SEQUENCE CHARACTERISTICS:
        ( A ) LENGTH: 43 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:335:

GGGACCCUUG AGAUACACGG CUUCGGCCGU GGACUCGGGU CUC 43

( 2 ) INFORMATION FOR SEQ ID NO:336:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:336:

NNNGAGCCUA GCAACCUGGG CUAGGAAU 28

( 2 ) INFORMATION FOR SEQ ID NO:337:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 7-12
        ( D ) OTHER INFORMATION: This symbol stands for
            the complimentary base for the Y's
            located in positions 22-27

( x i ) SEQUENCE DESCRIPTION: SEQ ID NO:337:

UUCCGANNNN NNACGGGANA AYYYYYY 27

( 2 ) INFORMATION FOR SEQ ID NO:338:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:338:

NNCACCAUC AGGGNN 15

( 2 ) INFORMATION FOR SEQ ID NO:339:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:339:

GAGCGCAAGA CGAAUAG 17

( 2 ) INFORMATION FOR SEQ ID NO:340:

( i ) SEQUENCE CHARACTERISTICS:
        ( A ) LENGTH: 12 nucleotides
        ( B ) TYPE: nucleic acid (C) STRANDEDNESS: single
(D) TOPOLOGY: linear (x i) SEQUENCE DESCRIPTION: SEQ ID NO:340:

UAAGGAGGCC AC                                                                                    12

(2) INFORMATION FOR SEQ ID NO:341:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (i x) FEATURE:
        (A) NAME/KEY: N
        (B) LOCATION: 6 AND 18
        (D) OTHER INFORMATION: This symbol stands for A or U (x i) SEQUENCE DESCRIPTION: SEQ ID NO:341:

NNYRSNGACA CGAANNCNSY RNGGAACNNU CGNN                                                             34

(2) INFORMATION FOR SEQ ID NO:342:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (i x) FEATURE:
        (A) NAME/KEY: N
        (B) LOCATION: 1-5, 16
        (D) OTHER INFORMATION: This symbol stands for
            the complimentary base for the Y's
            located at positions 17, and 25-29

(x i) SEQUENCE DESCRIPTION: SEQ ID NO:342:

NNNNNUUGAG ANACANYUGG ACUCYYYYY                                                                   29

(2) INFORMATION FOR SEQ ID NO:343:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (i x) FEATURE:
        (A) NAME/KEY: N
        (B) LOCATION: 1-4
        (D) OTHER INFORMATION: This symbol stands for
            the complimentary base for the Y's
            located in positions 22-25

(x i) SEQUENCE DESCRIPTION: SEQ ID NO:343:

NNNNGNNGAN ACAGCUGGAC ACYYYY                                                                      26

(2) INFORMATION FOR SEQ ID NO:344:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (x i) SEQUENCE DESCRIPTION: SEQ ID NO:344:

UUCGAAUGAU CCCUUAACCG GUUGAUCUAU GAA                                                              33

(2) INFORMATION FOR SEQ ID NO:345:

( i ) SEQUENCE CHARACTERISTICS:
    ( A ) LENGTH: 51 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:345:

UAAUAUAUCA AGAGCCUAAU AACUCGGGCU AUAAACUAAG GAAUAUCUAU    50

G    51

( 2 ) INFORMATION FOR SEQ ID NO:346:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:346:

GAGCCUNNNN NNNNGGGCUA    20

( 2 ) INFORMATION FOR SEQ ID NO:347:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:347:

GAGCCUARYA ACYYGGGCUA    20

( 2 ) INFORMATION FOR SEQ ID NO:348:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:348:

GAGCCUAAUA ACUCGGGCUA    20

( 2 ) INFORMATION FOR SEQ ID NO:349:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:349:

GAGCCUAGCA ACCUGGGCUA    20

( 2 ) INFORMATION FOR SEQ ID NO:350:

( i ) SEQUENCE CHARACTERISTICS:
        ( A ) LENGTH: 73 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:350:

TAATACGACT CACTATAGGG AGCATCAGAC TTTTAATCTG ACAATCAAGA    50

TCTATGAAAG AATTTTATAT CTC    73

( 2 ) INFORMATION FOR SEQ ID NO:351:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:351:

TCAGATTAAA AGTCTGATGC TCCCTATAGT GAGTCGTATT A        41

( 2 ) INFORMATION FOR SEQ ID NO:352:

( i ) SEQUENCE CHARACTERISTICS:
        ( A ) LENGTH: 31 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:352:

CCGGATCCGT TTCAATAGAG ATATAAAATT C        31

( 2 ) INFORMATION FOR SEQ ID NO:353:

( i ) SEQUENCE CHARACTERISTICS:
        ( A ) LENGTH: 50 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:353:

TTTCATAGAT NNNNNNNNN NNNNNNNNN NNNNNNNNN NNCTTGATTG        50

( 2 ) INFORMATION FOR SEQ ID NO:354:

( i ) SEQUENCE CHARACTERISTICS:
        ( A ) LENGTH: 105 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:354:

GGGAGCAUCA GACUUUUAAU CUGACAAUCA AGNNNNNNNN NNNNNNNNNN        50

NNNNNNNNNN NNNNAUCUAU GAAAGAAUUU UAUAUCUCUA UUGAAACGGA        100

UCCGG        105

( 2 ) INFORMATION FOR SEQ ID NO:355:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:355:

UCAAGAAUUC CGUUUUCAGU CGGGAAAAAC UGAACAAUCU        40

( 2 ) INFORMATION FOR SEQ ID NO:356:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:356:

ucaagAAUAU CUUCCGAAGC CGAACGGGAA AACCGGCAUC U 41

( 2 ) INFORMATION FOR SEQ ID NO:357:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:357:

UCAAGAAUAU CUUCCGAGGC CGAACGGGAA AACCGACAUC U 41

( 2 ) INFORMATION FOR SEQ ID NO:358:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:358:

UCAAGGGCAU CUGGGAGGGU AAGGGUAAGG UUGUCGGAUC U 41

( 2 ) INFORMATION FOR SEQ ID NO:359:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:359:

UCAAGAAUAU AUCCGAACUC GACGGGAUAA CGAGAAGAUC U 41

( 2 ) INFORMATION FOR SEQ ID NO:360:

( i ) SEQUENCE CHARACTERISTICS:
        ( A ) LENGTH: 39 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:360:

UCAAGUACCU AGGUGAUAAA AGGGAGAACA CGUGUGACU 39

( 2 ) INFORMATION FOR SEQ ID NO:361:

( i ) SEQUENCE CHARACTERISTICS:
        ( A ) LENGTH: 41 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:361:

UCAAGACAGU AUCCGUUCUU GAUCAUCGGG ACAAAUGAUC U 41

( 2 ) INFORMATION FOR SEQ ID NO:362:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:362:

UCAAGAAUUC CGUUUCAGU CGGGAAAAAC UGAACAAUCU 40

( 2 ) INFORMATION FOR SEQ ID NO:363:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:363:

AGUCGGGAAA AACUGAACAA UCUAUGAAAG 30

( 2 ) INFORMATION FOR SEQ ID NO:364:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:364:

GCCGAACGGG AAAACCGGCA UCUAUGAAAG 30

( 2 ) INFORMATION FOR SEQ ID NO:365:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:365:

CAAUCAAGAA UUCCGUUUUC AGUCG 25

( 2 ) INFORMATION FOR SEQ ID NO:366:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:366:

AAGAAUAUCU UCCGAAGCCG AACGG 25

( 2 ) INFORMATION FOR SEQ ID NO:367:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:367:

NNNRNNCACC AUCAGGGNNY NNN 23

( 2 ) INFORMATION FOR SEQ ID NO:368:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:368:

AGAUGAAGAU ACAGCUCUAG AUGCUGGACA CAUCU 35

( 2 ) INFORMATION FOR SEQ ID NO:369:

( i ) SEQUENCE CHARACTERISTICS:
    ( A ) LENGTH: 33 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:369:

UUCGAAUGAU CCCUUAACCG GUUGAUCUAU GAA    33

( 2 ) INFORMATION FOR SEQ ID NO:370:

( i ) SEQUENCE CHARACTERISTICS:
        ( A ) LENGTH: 31 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:370:

UGGGCGCAGC GUCAAUGACG CUGACGGUAC A    31

( 2 ) INFORMATION FOR SEQ ID NO:371:

( i ) SEQUENCE CHARACTERISTICS:
        ( A ) LENGTH: 16 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:371:

NNNNNUKGAG RHACHN    16

( 2 ) INFORMATION FOR SEQ ID NO:372:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:372:

NDGGMCUCNN NNN    13

( 2 ) INFORMATION FOR SEQ ID NO:373:

( i ) SEQUENCE CHARACTERISTICS:
        ( A ) LENGTH: 14 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:373:

NNNNGHWGAH ACAG    14

( 2 ) INFORMATION FOR SEQ ID NO:374:

( i ) SEQUENCE CHARACTERISTICS:
        ( A ) LENGTH: 12 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:374:

CUGGACACNN NN    12

METHOD FOR DETECTING A TARGET MOLECULE IN A SAMPLE USING A NUCLEIC ACID LIGAND

This is a continuation of application(s) Ser. No. 07/714,131 filed on Jun. 10, 1991, now U.S. Pat. No. 5,475,096, which is a Continuation-in-Part of U.S. patent application Ser. No. 07/536,428, filed Jun. 11, 1990, entitled Systematic Evolution of Ligands By Exponential Enrichment, now abandoned.

This work was supported by grants from the United States Government funded through the National Institutes of Health. The U.S. Government has certain rights in this invention.

FIELD OF THE INVENTION

We describe herein a new class of high-affinity nucleic acid ligands that specifically bind a desired target molecule. A method is presented for selecting a nucleic acid ligand that specifically binds any desired target molecule. The method is termed SELEX, an acronym for Systematic Evolution of Ligands by Exponential enrichment. The method of the invention (SELEX) is useful to isolate a nucleic acid ligand for a desired target molecule. The nucleic acid products of the invention are useful for any purpose to which a binding reaction may be put, for example in assay methods, diagnostic procedures, cell sorting, as inhibitors of target molecule function, as probes, as sequestering agents and the like. In addition, nucleic acid products of the invention can have catalytic activity. Target molecules include natural and synthetic polymers, including proteins, polysaccharides, glycoproteins, hormones, receptors and cell surfaces, and small molecules such as drugs, metabolites, cofactors, transition state analogs and toxins.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, must possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding proteins, it has become possible to describe the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from *E. coli*. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the many roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose functions is to inactivate ribosomes in a target organism. A family of evolutionarily related RNAs with specificity and decent affinity to nucleotides and nucleosides (Bass, B. and Cech, T. (1984) Nature 308:820–826) as well as to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et al. (1983) J. Biomol. Structure Dynamics 1:539 and Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specifity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988) Proc. Natl. Acad. Sci. USA 85:1364–1368).

A type of in vitro evolution was reported in replication of the RNA bacteriophage Qβ. Mills, D. R. et al. (1967) Proc. Natl. Acad. Sci USA 58:217–224; Levinsohn, R. and Spiegleman, S. (1968) Proc. Natl. Acad. Sci. USA 60:866–872; Levisohn, R. and Spiegelman S. (1969) Proc. Natl. Acad. Sci. USA 63:805–811; Saffhill, R. et al. (1970) J. Mol. Biol. 51:531–539; Kacian, D. L. et al. (1972) Proc. Natl. Acad. Sci. USA 69:3038–3042; Mills, D. R. et al. (1973) Science 180:916–927. The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in *RNA: Catalysis, Splicing, Evolution,* Belfort and Shub (eds.), Elsevier, Amsterdam pp. 83–87; and Robertson and Joyce (1990) Nature 344:467) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using an oligodeoxynucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate. Only a limited array of variants was testable, since variation depended upon single nucleotide changes occurring during amplification.

The prior art has not taught or suggested more than a limited range of chemical functions for nucleic acids in their interactions with other substances: as targets for protein ligands evolved to bind certain specific olignocleotide sequences; more recently, as cataysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

SUMMARY OF THE INVENTION

The present invention provides a class of products which are nucleic acid molecules, each having a unique sequence, each of which has the property of binding specifically to a desired target compound or molecule. Each compound of the invention is a specific ligand of a given target molecule. The invention is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets. Most commonly, and preferably, for therapeutic applications, binding takes place in aqueous solution at conditions of salt, temperature and pH near acceptable physiological limits.

The invention also provides a method which is generally applicable to make a nucleic acid ligand for any desired target. The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by a theory of preparation, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have 420 candidate possibilities. Those which have the higher affinity constants for the target are most likely to bind. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The iterative selection/amplification method is sensitive enough to allow isolation of a single sequence variant in a mixture containing at least 65,000 sequence variants. The method is even capable of isolating a small number of high affinity sequences in a mixture containing $10^{14}$ sequences. The method could, in principle, be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the present invention, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly effecting the affinity of the nucleic acid ligands to the target. By terminating the SELEX process prior to completion, it is possible to determine the sequence of a number of members of the nucleic acid ligand solution family, which will allow the determination of a comprehensive description of the nucleic acid ligand solution.

After a description of the nucleic acid ligand family has been resolved by SELEX, in certain cases it may be desirable to perform a further series of SELEX that is tailored by the information received during the SELEX experiment. In one embodiment, the second series of SELEX will fix those conserved regions of the nucleic acid ligand family while randomizing all other positions in the ligand structure. In an alternate embodiment, the sequence of the most representative member of the nucleic acid ligand family may be used as the basis of a SELEX process wherein the original pool of nucleic acid sequences is not completely randomized but contains biases towards the best known ligand. By these methods it is possible to optimize the SELEX process to arrive at the most preferred nucleic acid ligands.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, psuedoknots and myriad combinations of the same. Almost all known cases of such motifs suggest that they can be formed in a nucleic acid sequence of no more than 30 nucleotides. For this reason, it is preferred that SELEX procedures with contiguous randomized segments be initiated with nucleic acid sequences containing a randomized segment of between about 20–50 nucleotides, and in the most preferred embodiments between 25 and 40 nucleotides. This invention includes solutions comprising a mixture of between about $10^9$ to $10^{18}$ nucleic acid sequences having a contiguous randomized sequence of at least about 15 nucleotides in length. In the preferred embodiment, the randomized section of sequences is flanked by fixed sequences that facilitate the amplification of the ligands.

In the case of a polymeric target, such as a protein, the ligand affinity can be increased by applying SELEX to a mixture of candidates comprising a first selected sequence and second randomized sequence. The sequence of the first selected ligand associated with binding or subportions thereof can be introduced into the randomized portion of the nucleic acids of a second test mixture. The SELEX procedure is repeated with the second test mixture to isolate a second nucleic acid ligand, having two sequences selected for binding to the target, which has increased binding strength or increased specificity of binding compared to the first nucleic acid ligand isolated. The sequence of the second nucleic acid ligand associated with binding to the target can then be introduced into the variable portion of the nucleic acids of a third test mixture which, after cycles of SELEX results in a third nucleic acid ligand. These procedures can be repeated until a nucleic acid ligand of a desired binding strength or a desired specificity of binding to the target molecule is achieved. The process of iterative selection and combination of nucleic acid sequence elements that bind to a selected target molecule is herein designated "walking," a term which implies the optimized binding to other accessible areas of a macromolecular target surface or cleft, starting from a first binding domain. Increasing the area of binding contact between ligand and target can increase the affinity constant of the binding reaction. These walking procedures are particularly useful for the isolation of nucleic acid antibodies which are highly specific for binding to a particular target molecule.

A variant of the walking procedure employs a non-nucleic acid ligand termed "anchor" which binds to the target molecule as a first binding domain. (See FIG. 9.) This anchor molecule can in principle be any non-nucleic acid molecule that binds to the target molecule and which can be covalently linked directly or indirectly to a nucleic acid. When the target molecule is an enzyme, for example, the anchor molecule can be an inhibitor or substrate of that enzyme. The anchor can also be an antibody or antibody fragment specific for the target. The anchor molecule is covalently linked to a nucleic acid oligomer of known sequence to produce a bridging molecule. The oligomer is preferably comprised of a minimum of about 3–10 bases. A test mixture of candidate nucleic acids is then prepared which includes a randomized portion and a sequence complementary to the known sequence of the bridging molecule. The bridging molecule is completed to the target molecule. SELEX is then applied to select nucleic acids which bind to the complex of the bridging molecule and the target molecule. Nucleic acid ligands which bind to the complex are isolated. Walking procedures as described above can then be applied to obtain nucleic acid ligands with increased binding strength or increased specificity of binding to the complex. Walking procedures could employ selections for binding to the complex or the target itself. This method is particularly useful to isolate nucleic acid ligands which bind at a particular site within the target molecule. The complementary sequence in the test mixture acts to ensure the isolation of nucleic acid sequences which bind to the target molecule at or near the binding site of the bridging molecule. If the bridging molecule is derived from an inhibitor of the target molecule, this method is likely to result in a nucleic acid ligand which inhibits the function of the target molecule. It is particularly useful, for example, for the isolation of nucleic acids which will activate or inhibit protein function. The combination of ligand and target can have a new or enhanced function.

The nucleic acid ligands of the present invention may contain a plurality of ligand components. As described above, nucleic acid ligands derived by walking procedures may be considered as having more than one nucleic acid ligand component. This invention also includes nucleic acid antibodies that are constructed based on the results obtained by SELEX while not being identical to a nucleic acid ligand identified by SELEX. For example, a nucleic acid antibody may be constructed wherein a plurality of identical ligand structures are made part of a single nucleic acid. In another embodiment, SELEX may identify more than one family of nucleic acid ligands to a given target. In such case, a single nucleic acid antibody may be constructed containing a plurality of different ligand structures. SELEX experiments also may be performed wherein fixed identical or different ligand structures are joined by random nucleotide regions and/or regions of varying distance between the fixed ligand structures to identify the best nucleic acid antibodies.

Screens, selections or assays to assess the effect of binding of a nucleic acid ligand on the function of the target molecule can be readily combined with the SELEX methods. Specifically, screens for inhibition or activation of enzyme activity can be combined with the SELEX methods.

In more specific embodiments, the SELEX method provides a rapid means for isolating and identifying nucleic acid ligands which bind to proteins, including both nucleic acid-binding proteins and proteins not known to bind nucleic acids as part of their biological function. Nucleic acid-binding proteins include among many others polymerases and reverse transcriptases. The methods can also be readily applied to proteins which bind nucleotides, nucleosides, nucleotide co-factors and structurally related molecules.

In another aspect, the present invention provides a method for detecting the presence or absence of, and/or measuring the amount of a target molecule in a sample, which method employs a nucleic acid ligand which can be isolated by the methods described herein. Detection of the target molecule is mediated by its binding to a nucleic acid ligand specific for that target molecule. The nucleic acid ligand can be labeled, for example radiolabeled, to allow qualitative or quantitative detection. The detection method is particularly useful for target molecules which are proteins. The method is more particularly useful for detection of proteins which are not known to bind nucleic acids as part of their biological function. Thus, nucleic acid ligands of the present invention can be employed in diagnostics in a manner similar to conventional antibody-based diagnostics. One advantage of nucleic acid ligands over conventional antibodies in such detection method and diagnostics is that nucleic acids are capable of being readily amplified in vitro, for example, by use of PCR amplification or related methods. Another advantage is that the entire SELEX process is carried out in vitro and does not require immunizing test animals. Furthermore, the binding affinity of nucleic acid ligands can be tailored to the user's needs.

Nucleic acid ligands of small molecule targets are useful as diagnostic assay reagents and have therapeutic uses as sequestering agents, drug delivery vehicles and modifiers of hormone action. Catalytic nucleic acids are selectable products of this invention. For example, by selecting for binding to transition state analogs of an enzyme catalyzed reaction, catalytic nucleic acids can be selected.

In yet another aspect, the present invention provides a method for modifying the function of a target molecule using nucleic acid ligands which can be isolated by SELEX. Nucleic acid ligands which bind to a target molecule are screened to select those which specifically modify function of the target molecule, for example to select inhibitors or activators of the function of the target molecule. An amount of the selected nucleic acid ligand which is effective for modifying the function of the target is combined with the target molecule to achieve the desired functional modification. This method is particularly applicable to target molecules which are proteins. A particularly useful application of this method is to inhibit protein function, for example to inhibit receptor binding to an effector or to inhibit enzyme catalysis. In this case, an amount of the selected nucleic acid molecule which is effective for target protein inhibition is combined with the target protein to achieve the desired inhibition.

BRIEF DESCRIPTION OF THE FIGURES

FIG. 1 is a diagram of the ribonucleotide sequence of a portion of the gene 43 messenger RNA which encodes the bacteriophage T4 DNA polymerase. Shown is the sequence in the region known to bind to gp43. The bold-faced capitalized letters indicate the extent of the information required for binding of gp43. The eight base-pair loop was replaced by randomized sequence to yield a candidate population for SELEX.

FIG. 8 is a series of diagrams showing synthesis of candidate nucleic acid ligands using the enzymes terminal transferase (TDT) and DNA polymerase (DNA pol). A 5' primer or primary ligand sequence is provided with a tail of randomized sequence by incubating with terminal transferase in the presence of the four deoxynucleotide triphosphates (dNTPs). Homopolymer tailing of the randomized segment, using the same enzyme in the presence of a single deoxynucleotide triphosphate (e.g. dCTP) provides an annealing site for poly-G tailed 3' primer. After annealing, the double-stranded molecule is completed by the action of DNA polymerase. The mixture can be further amplified, if desired, by the polymerase chain reaction.

FIGS. 10 and 11 are diagrams of a selection process using SELEX in two stages. In FIG. 10, SELEX is applied to select ligands that bind to secondary binding sites on a target complexed with a bridging oligonucleotide connected to a specific binder, e.g., inhibitor of the target protein. The bridging oligonucleotide acts as a guide to favor selection of ligands that bind to accessible secondary binding sites. In FIG. 11, a second SELEX is applied to evolve ligands that bind at both the secondary sites originally selected for and the primary target domain. The nucleic acids thereby evolved will bind very tightly, and may themselves act as inhibitors of the target protein or to compete against inhibitors or substrates of the target protein.

The top line shows the sequences of oligomers 1b and 2b from left to right, respectively (see Table 2 infra). The second line shown, from left to right, the sequences of oligomers 3b, 4b and 5b (Table 2). Proper ligation of the oligomers was assured by hybridization with oligomers 1b and 2b, whose sequences are complementary. The resultant ligated template was gel-purified, annealed to oligomer 1b and used in an in vitro transcription reaction (Milligan et al. (1987)) to produce an RNA candidate mixture, shown in the last line of the figure, labeled "in vitro transcript." The candidate mixture contained a 32 nucleotide randomized segment, as shown.

Figure 13:
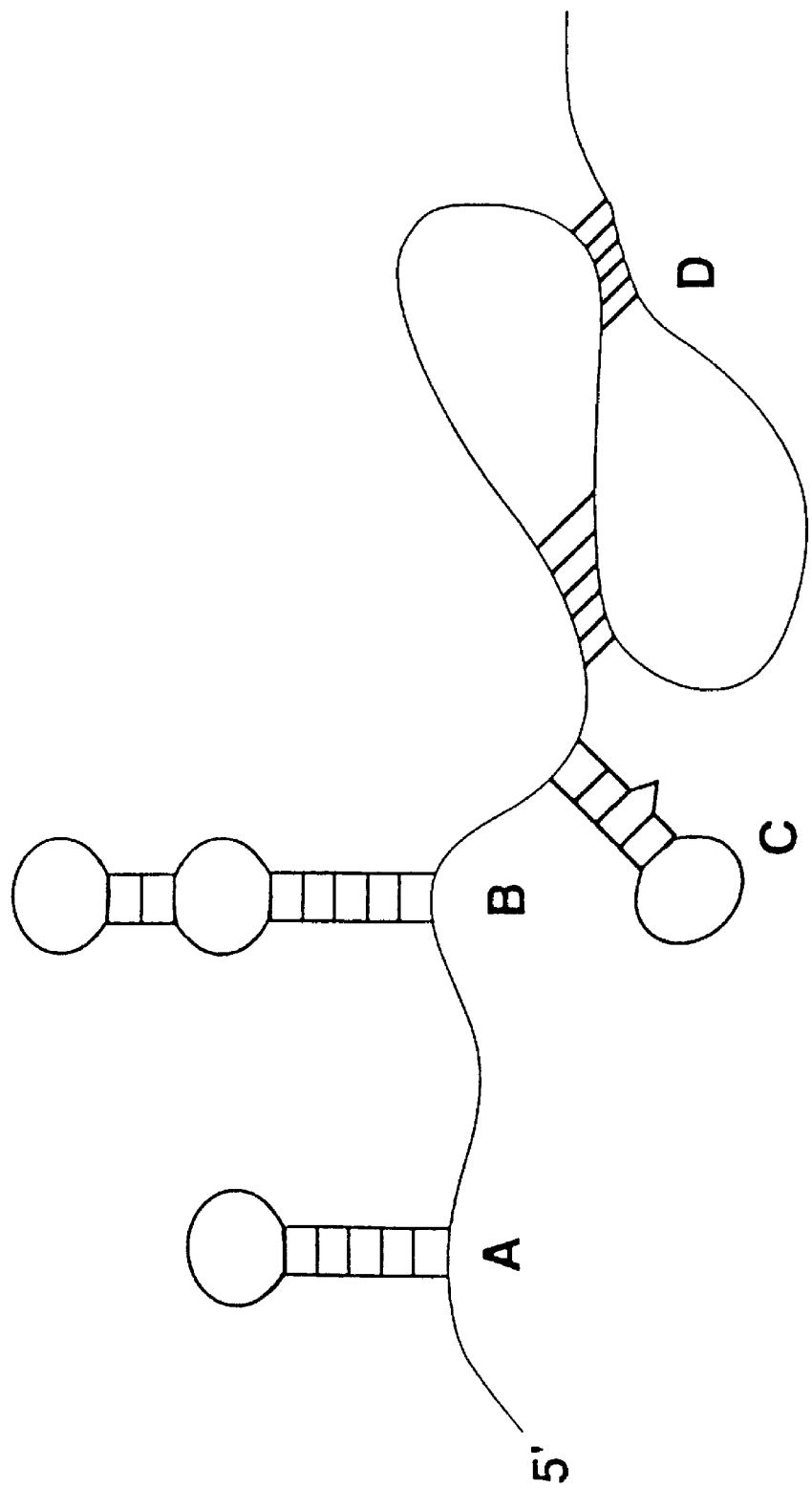

FIG. 13 shows a hypothetical RNA sequence containing a variety of secondary structures that RNA are known to undertake. Included are: A hairpin loops, B bulges, C asymmetric bulges, and D pseudoknots.

Figure 14:
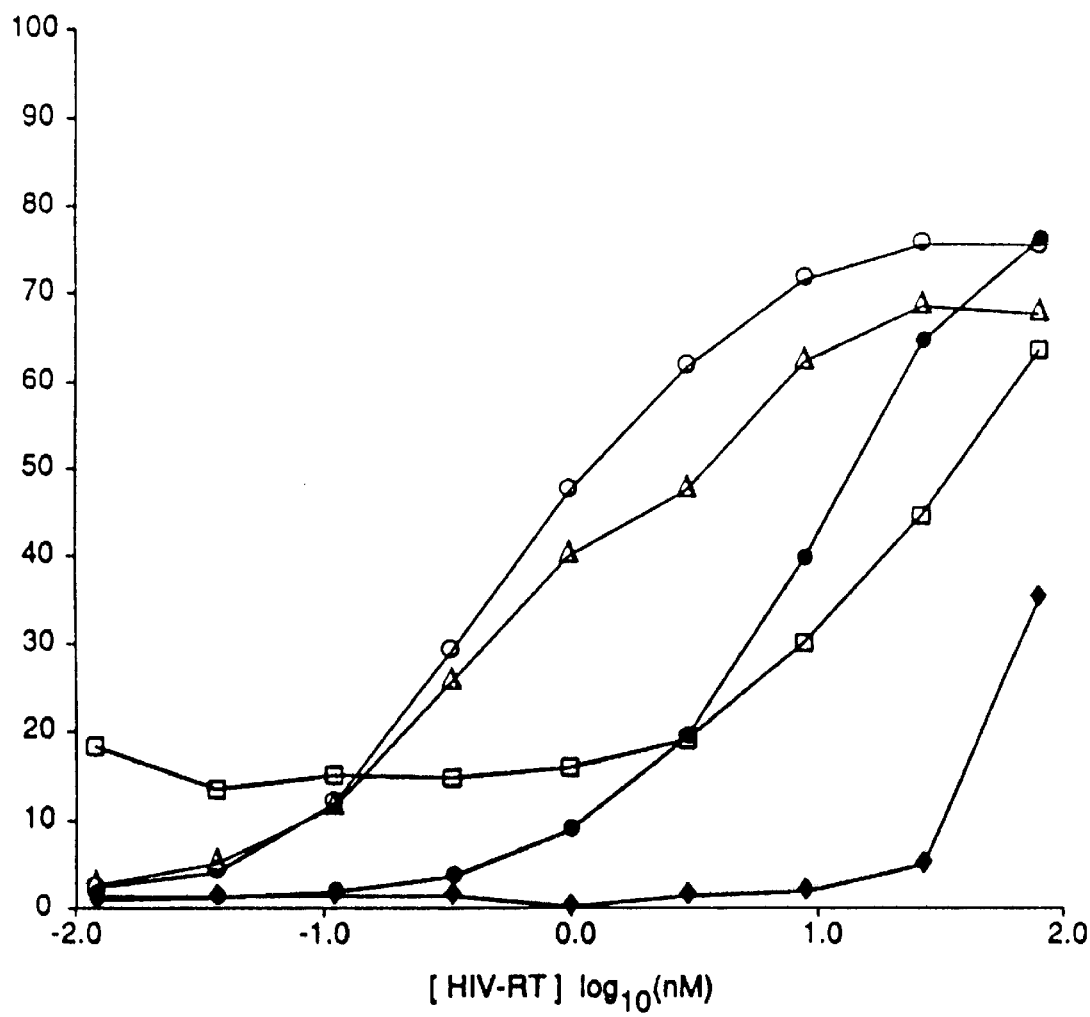

FIG. 14 shows nitrocellulose filter binding assays of ligand affinity for HIV-RT. Shown is the percent of input RNA that is bound to the nitrocellulose filter with varying concentrations of HIV-RT.

Figure 15:
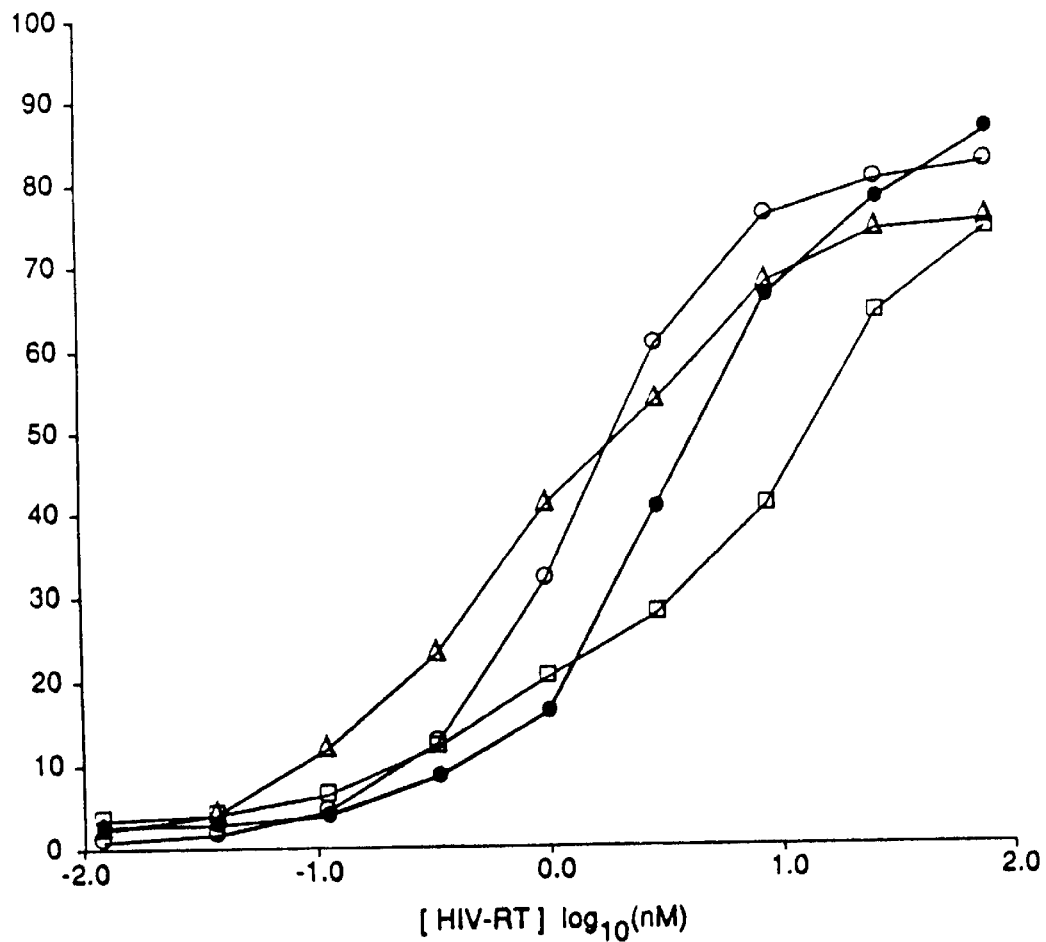

FIG. 15 shows additional nitrocellulose filter binding assays of ligand affinity for HIV-RT.

Figure 16A:
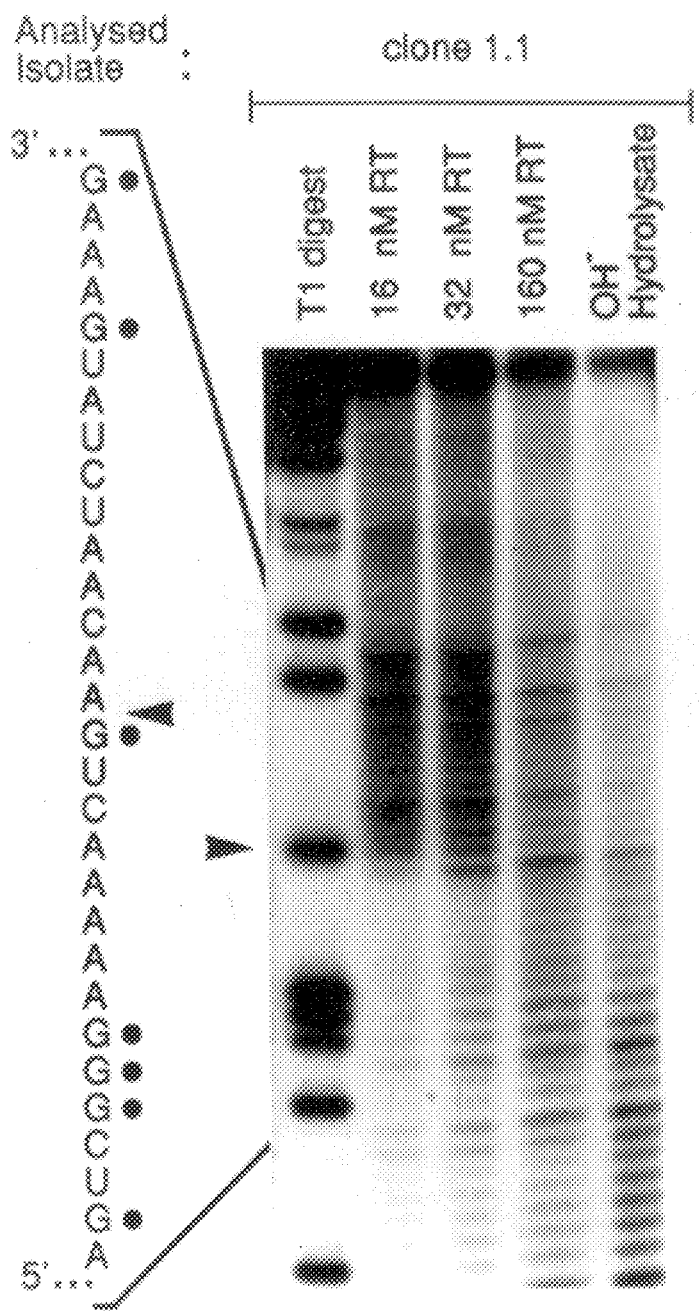
Figure 16B:
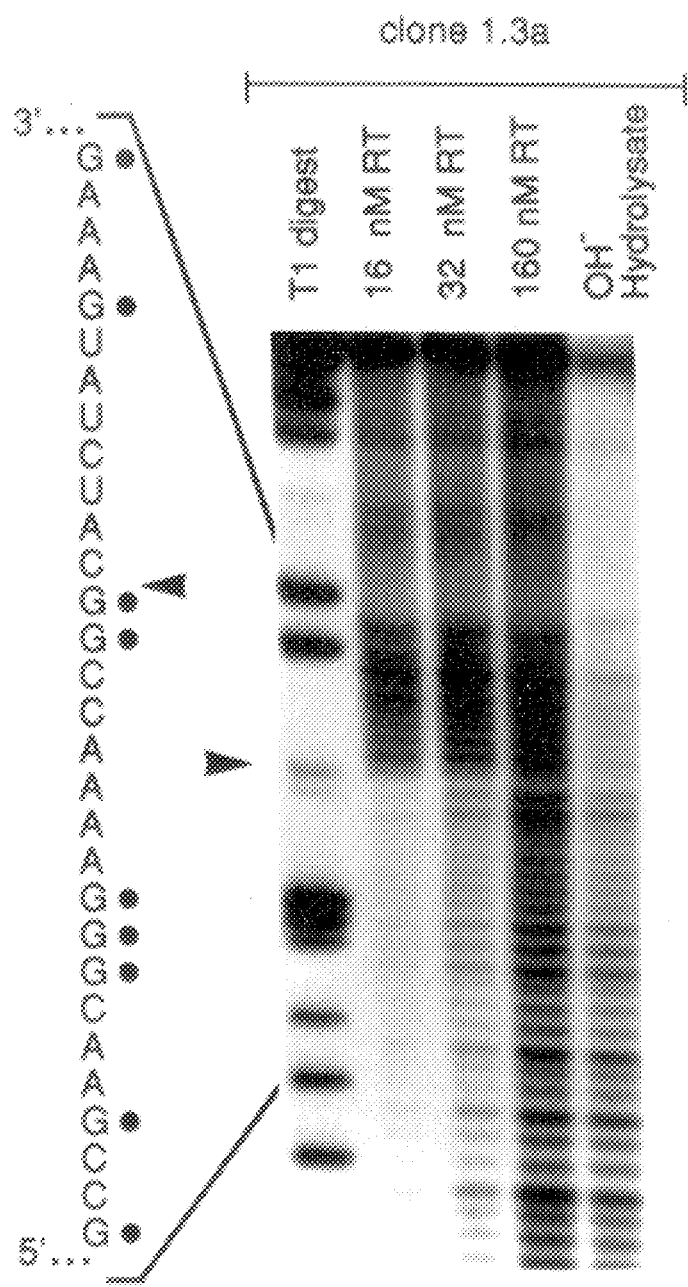
Figure 16:
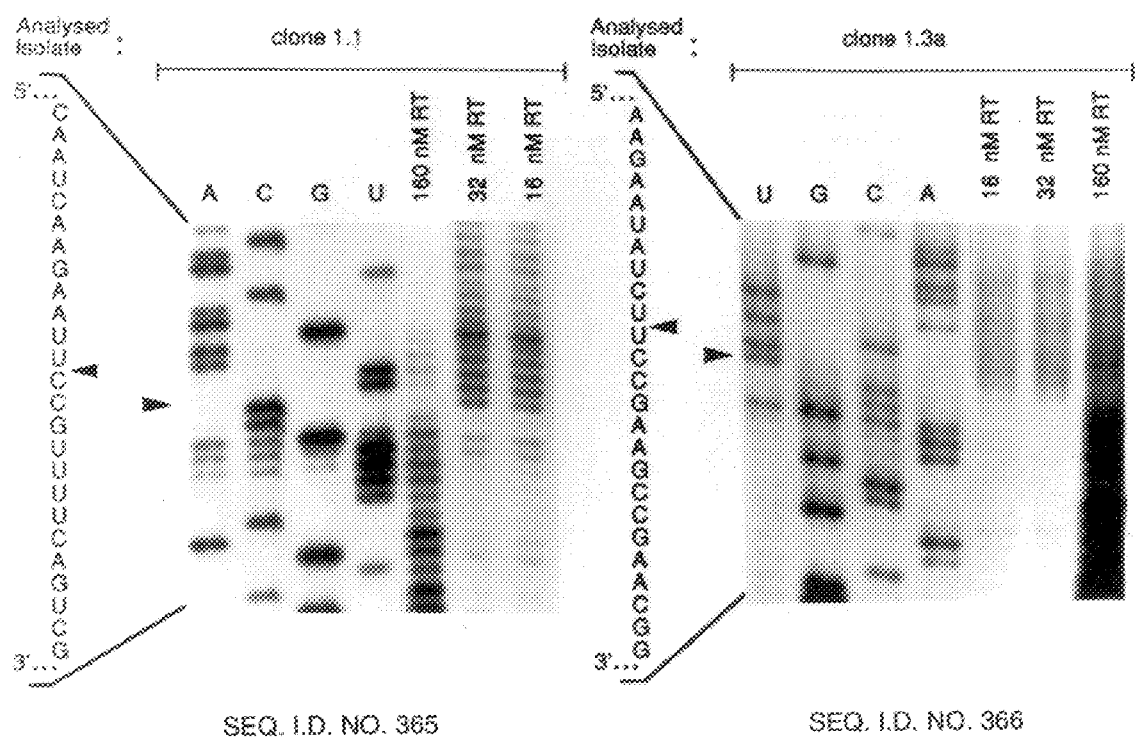

FIG. 16 shows information boundary determination for HIV-1 RT ligands 1.1 and 1.3a a) 3' boundary determination. RNAs were 5'0 end labeled, subjected to partial alkaline hydrolysis and selection on nitrocellulose filters, separated on a denaturing 8% polyacrylamide gel and autoradiographed. Approximately 90 picomoles of labeled RNA and 80 picomoles of HIV-1 RT were mixed in 0.5, 2.5, and 5 mls of buffer and incubated for 5 minutes at 37° C. prior to washing through a nitrocellulose filter. The eluated RNAs are shown under the final concentrations of HIV-1 RT used in each experiment. Also shown are the products of a partial RNase T1 digest which allows identification of the information boundary on the adjacent sequence as shown by arrows b) 5' boundary determination. The 5' boundary was determined in a) under the same conditions listed above.

Figure 17:
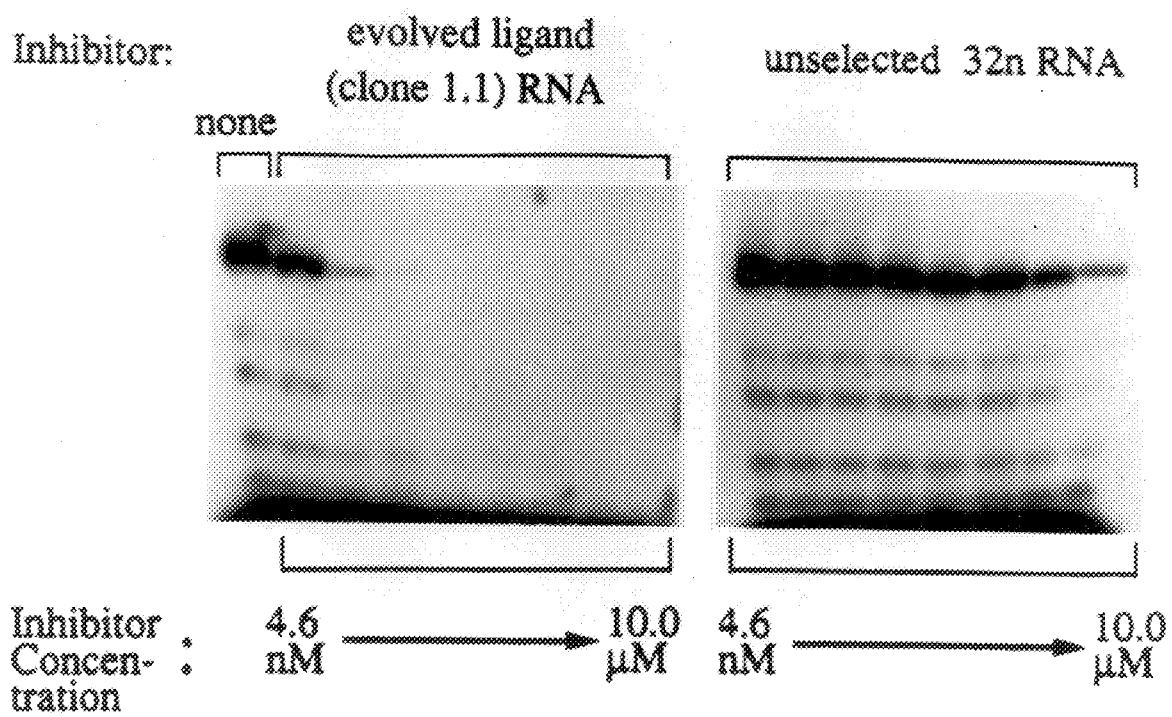

FIG. 17 shows the inhibition of HIV-1 RT by RNA ligand 1.1. A series of three-fold dilutions of 32N candidate mixture RNA and ligand 1.1 RNA ranging in final reaction concentration for 10 micromolar to 4.6 nanomolar and pre-mixed with HIV-RT and incubated for 5 minutes at 37° C. in 6 μL of 200 mM KOAc, 50 mM Tris-HCl, pH 7.7, 10 mM dithiothreitol, 6 mM Mg (OAc)$_2$, and 0.4 mM NTPS. In a separate tube RNA template (transcribed from a PCR product of a T7-1 obtained from U.S. Biochemical Corp. using oligos 7 and 9) and labeled oligo 9 were mixed and heated at 95° C. for one minute and cooled on ice for 15 minutes in 10 mM Tris-HCl, pH 7, 0.1 mM EDTA. Four μl of this template was added to each 6 μl enzyme-inhibitor mixture to start the reaction which was incubated for a further 5 minutes at 37° C. and then stopped. The final concentration of HIV-1 RT was 16 nanomolar, of RNA template was 13 nanomolar, and of labeled primer was 150 nanomolar in all reactions. The extension products of each reaction are shown.

Figure 18:
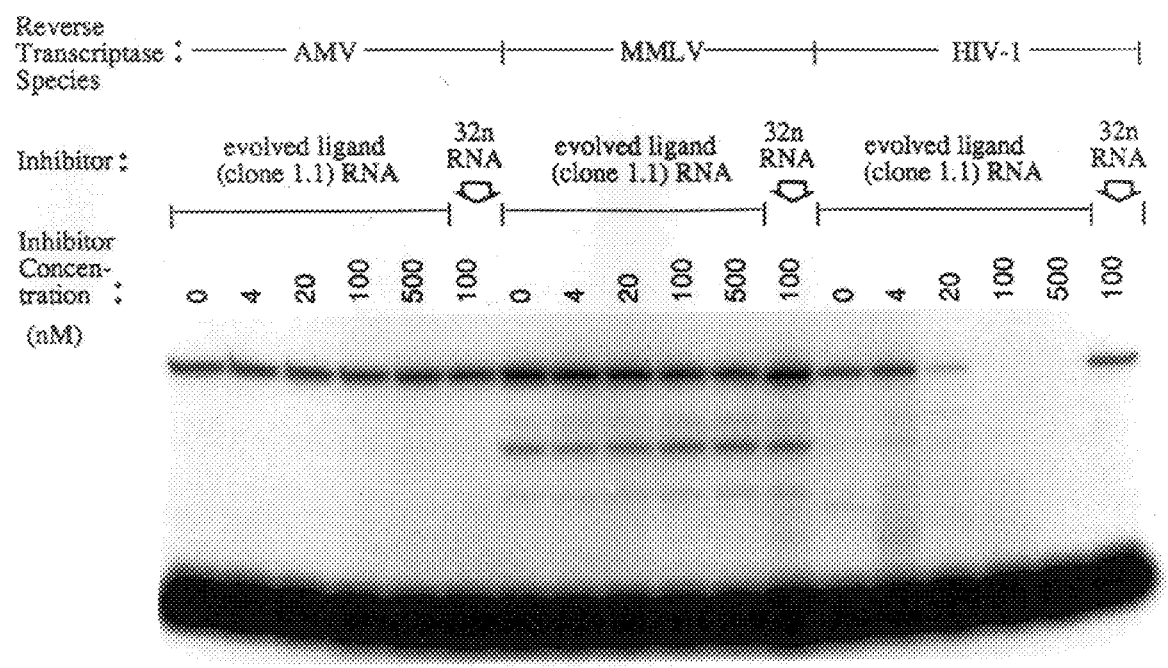

FIG. 18 shows a comparisons of HIV-1 RT inhibition by ligand 1.1 to effects on MMLV RT and AMV RT. Experiments were performed as in FIG. 17 except that 5-fold dilutions of inhibitor were prepared with the resultant concentrations as shown. The concentrations of each RT were normalized to that of HIV-RT by dilutions and comparison of gel band intensity with both Coomassie blue and silver stains, Biorad protein concentration assays, and activity assays.

Figures 19B, 19C:
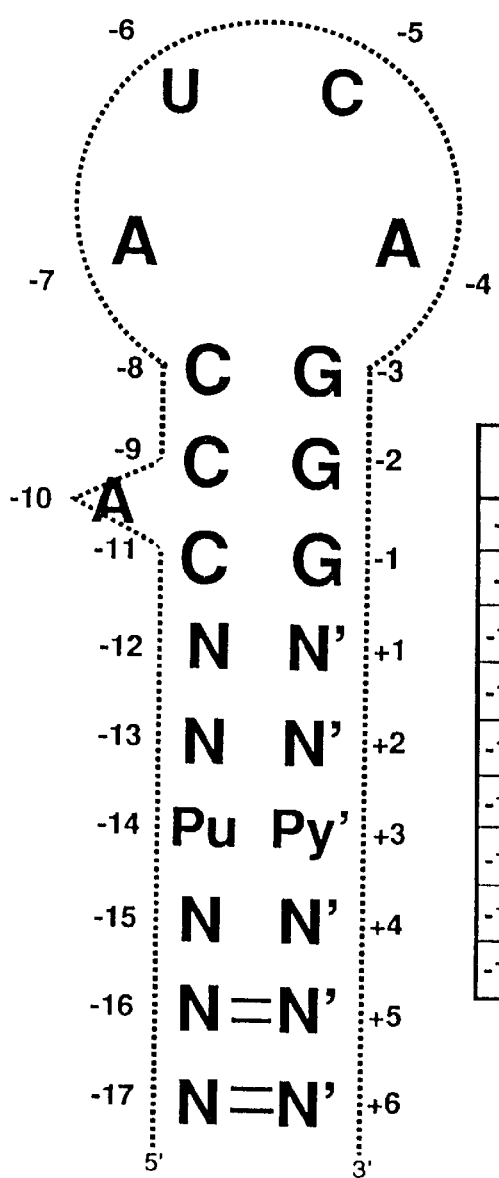

FIG. 19 shows the consensus sequences of selected hairpins representing the R-17 coat protein ligand solution. The nucleotide representation at each position is indicated in grids. The column headed "bulge" represents the number of clones with an extra-helical nucleotide on one or both sides of the stem between the corresponding stem base-pairs. The column headed "end" represents the number of clones whose hairpin terminated at the previous base-pair.

Figure 20:
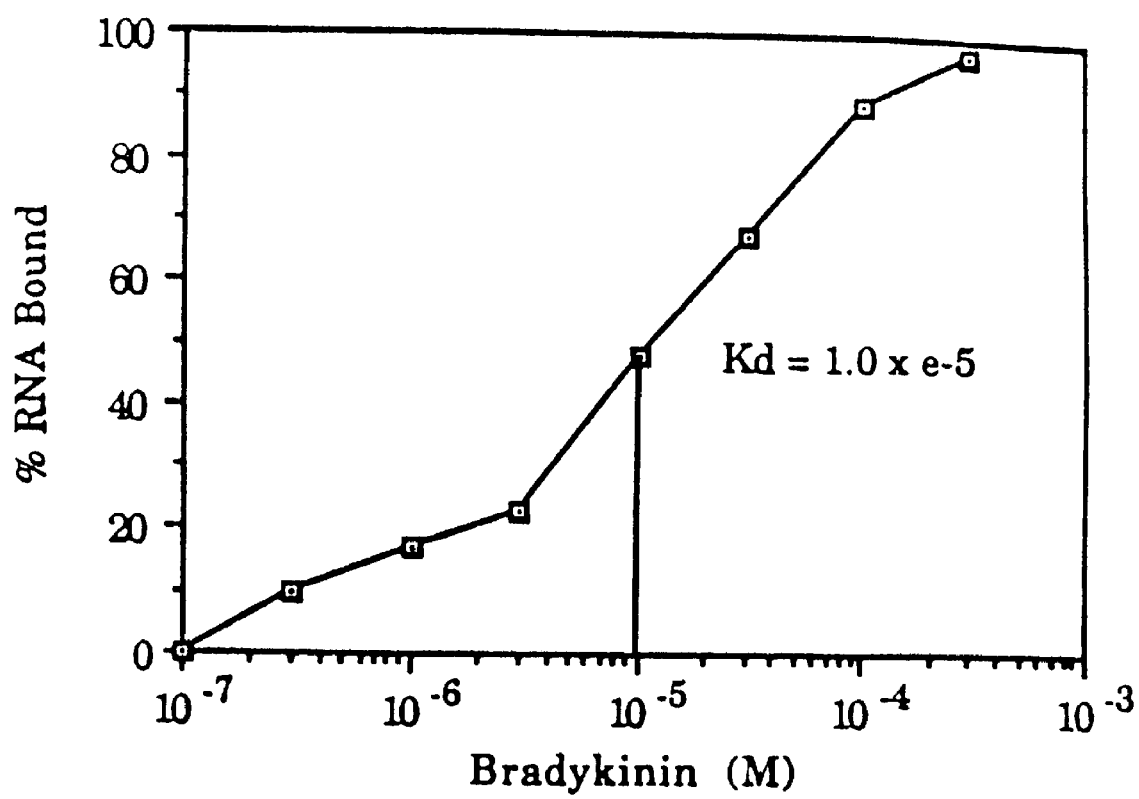

FIG. 20 shows a binding curve of 30N bulk RNA for bradykinin. Anaylsis was done using spin columns; 10 mM KOAc, 10 mM DEM, pH 7.5; RNA concentration $1.5 \times 10^{-8}$M.

FIG. 21 shows templates for use in the generation of candidate mixtures that are enriched in certain structural motifs. Template A is designed to enrich the candidate mixture in hairpin loops. Template B is designed to enrich the candidate mixture in pseudoknots.

Figure 22:
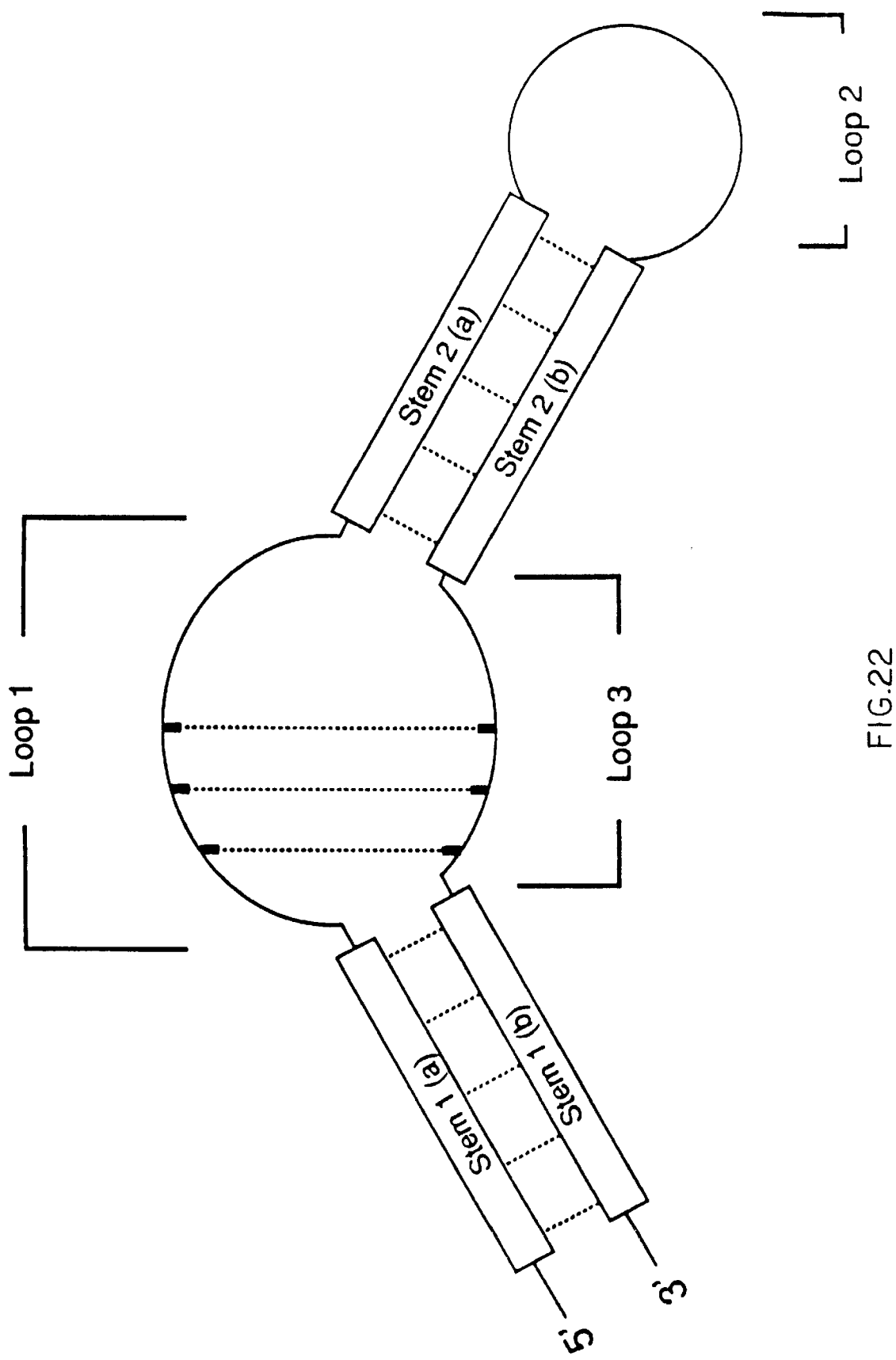

FIG. 22 is a schematic diagram of stem-loop arrangements for Motifs I and II of the HIV-rev ligand solution. The dotted lines in stems 1 and 2 between loops 1 and 3 indicate potential base-pairs.

FIG. 23 shows the folded secondary structures of rev ligand subdomains of isolates 6a, 1a, and 8 to show motifs I, II and III respectively. Also shown for comparison is the predicted fold of the wild type RRE RNA.

Figure 24:
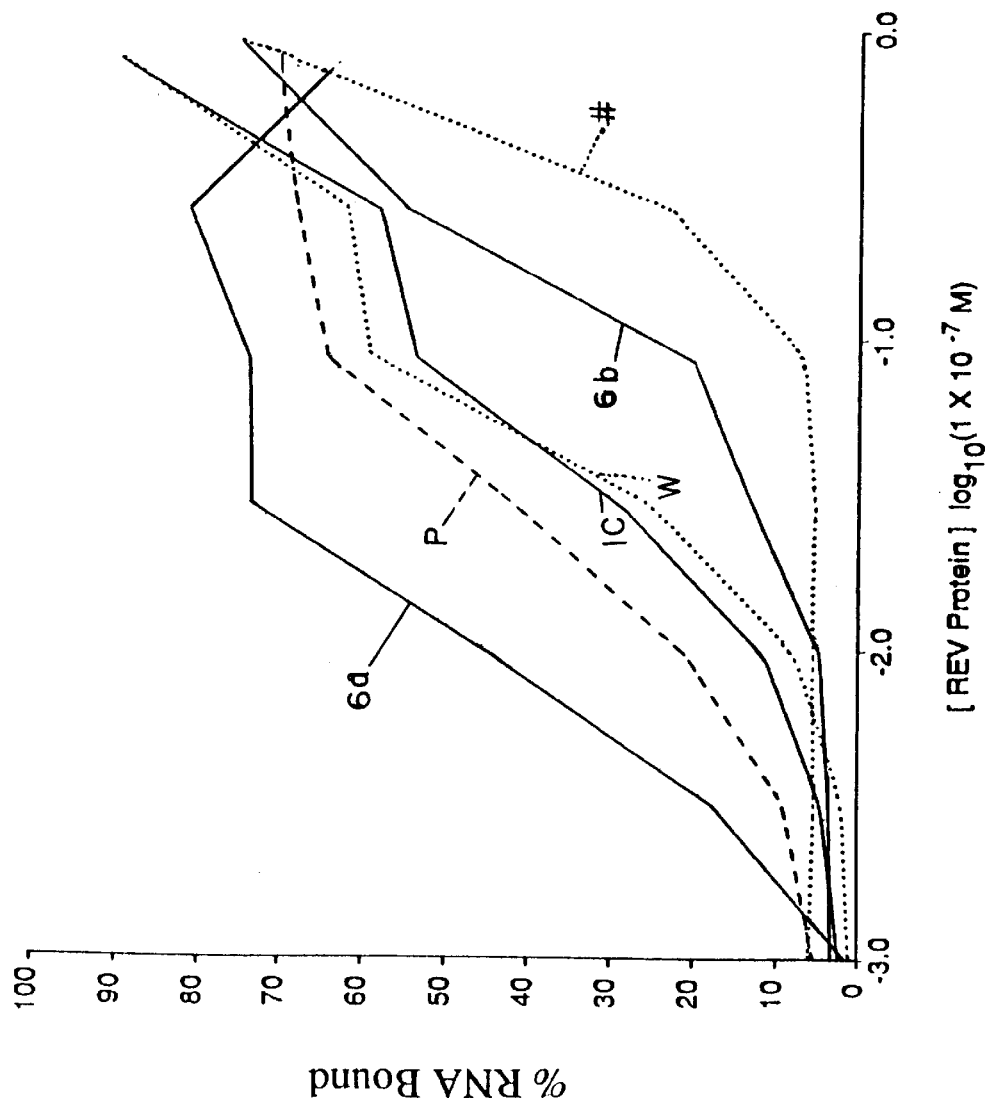

FIG. 24 is a graph of percent of input counts bound to a nitrocellulose filter with various concentrations of HIV rev protein. Also shown are the binding curves of the 32N starting population (#) and of the evolved population after 10 rounds (P) and of the wild type RRE sequence transcribed from a template composed of oligos 8 and 9(W).

Figure 25:
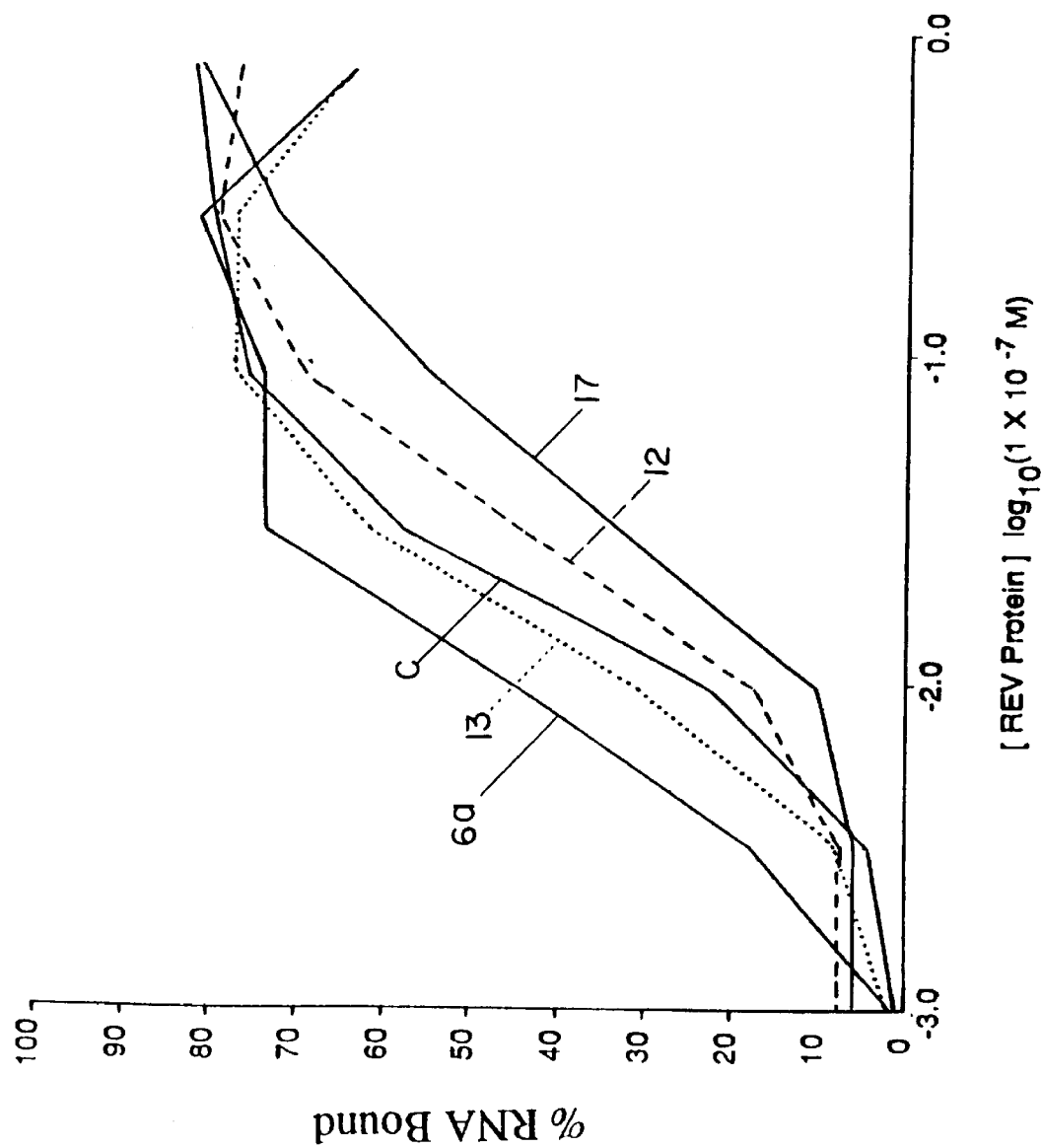

FIG. 25 is a comparison of Motif I(a) rev ligands. Paramenters are as in FIG. 24. Also included is the binding curve of the "consensus" construct (C).

Figure 26:
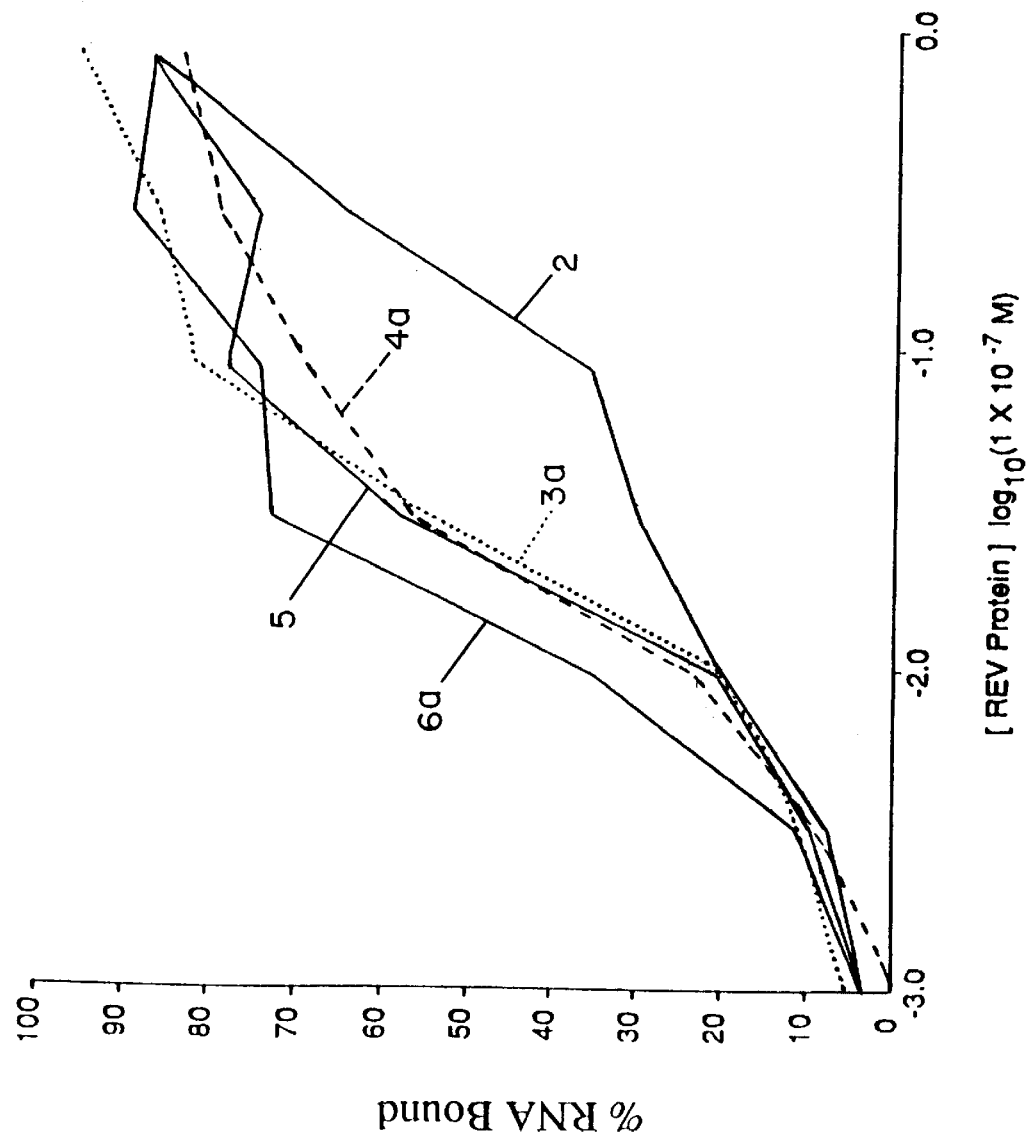

FIG. 26 is a comparison of Motif I(b) rev ligands. Parameters are as in FIG. 24.

Figure 27:
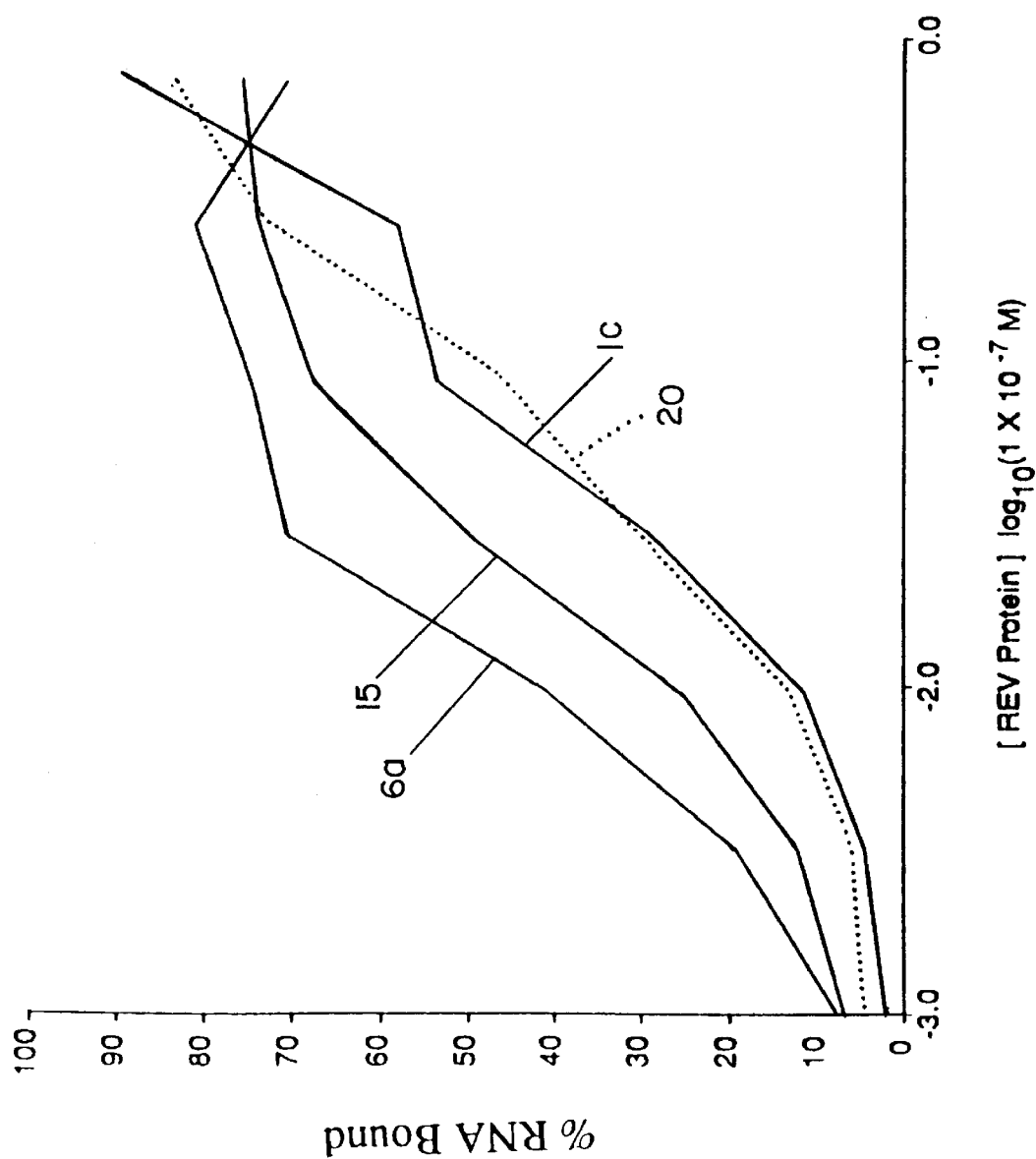

FIG. 27 is a comparison of Motif II rev ligands. Parameters are as in FIG. 24.

Figure 28:
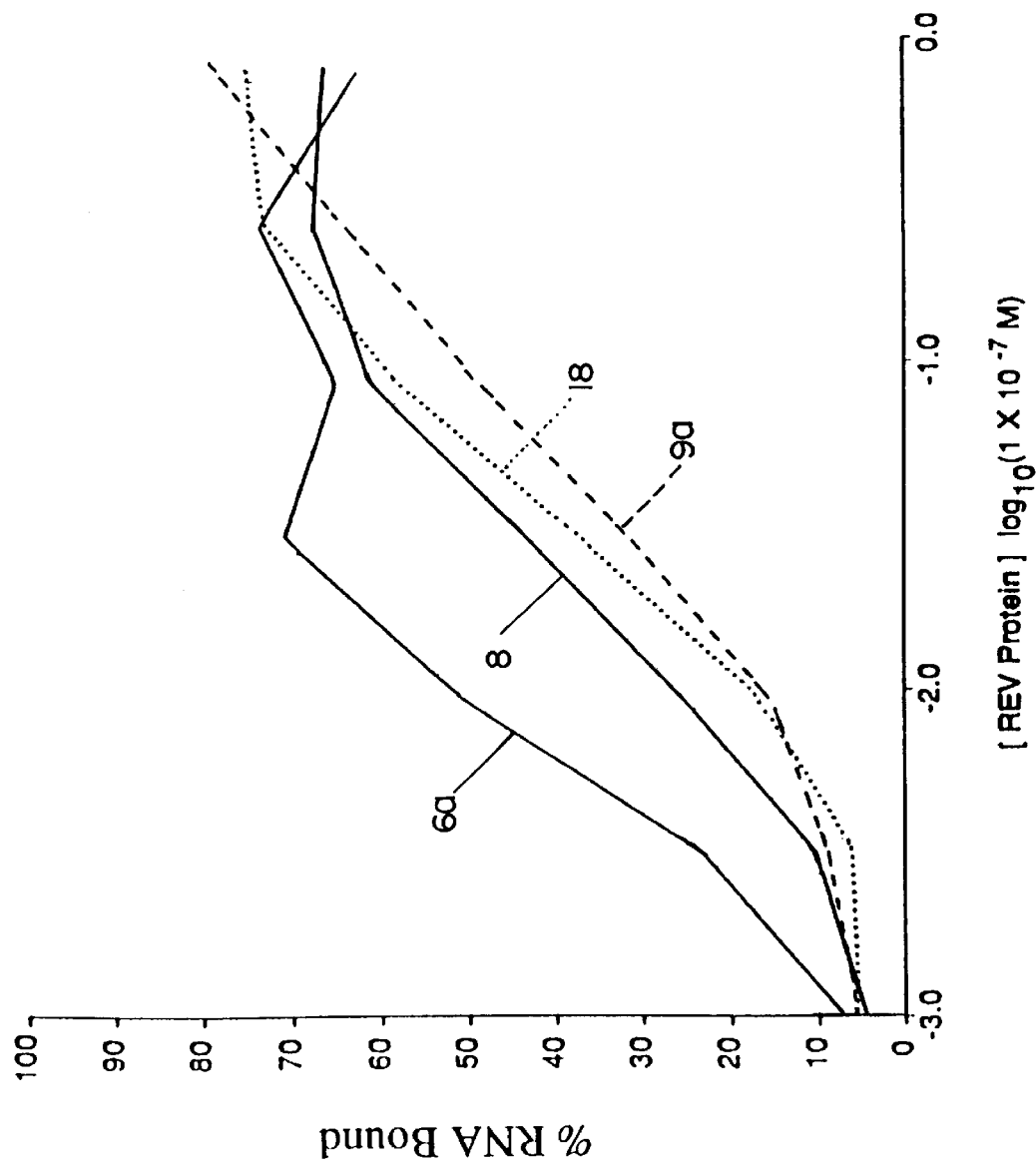

FIG. 28 is a comparison of Motif III rev ligands. Parameters are as in FIG. 24.

Figure 29:
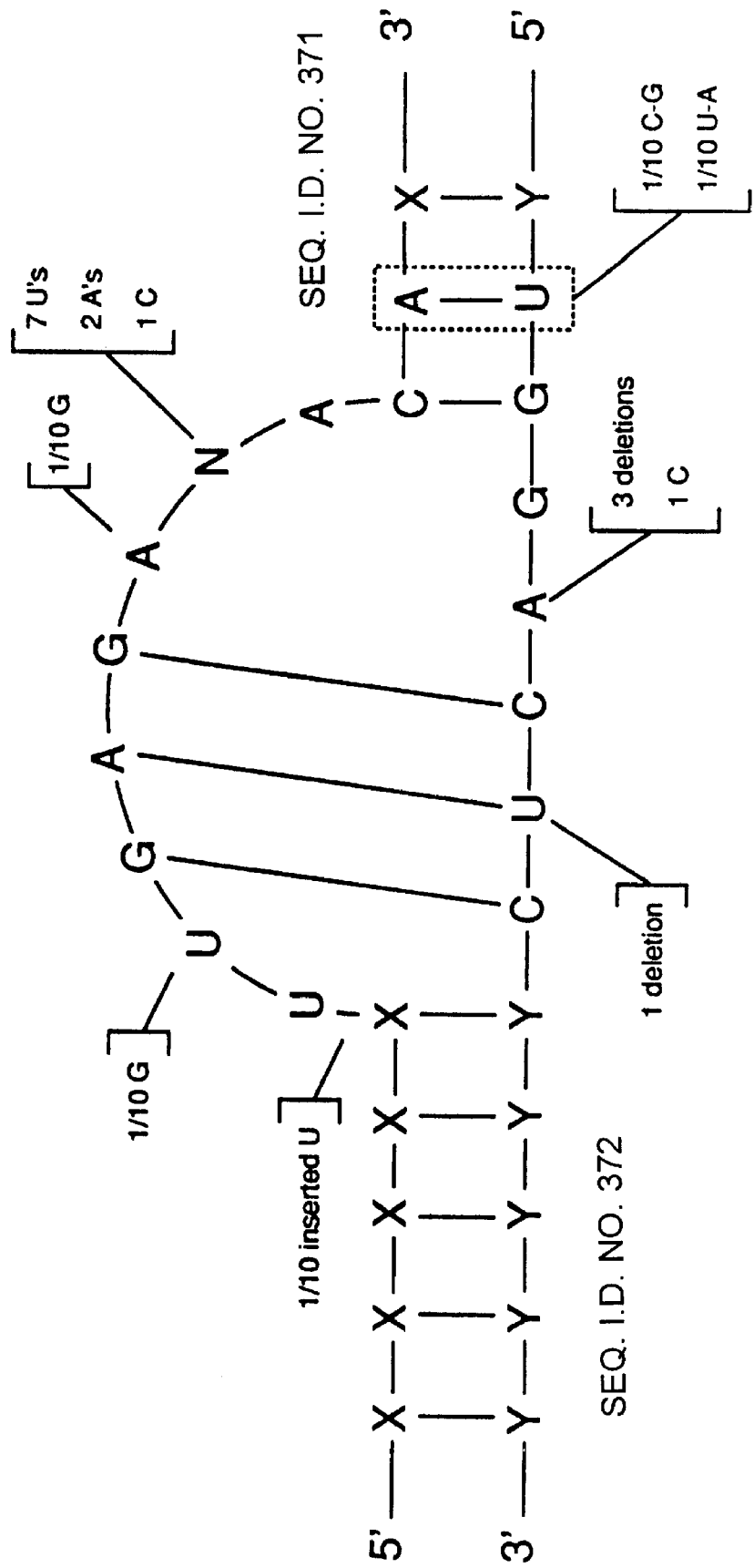

FIG. 29 shows the consensus nucleic acid ligand solution to HIV rev referred to as Motif I.

Figure 30:
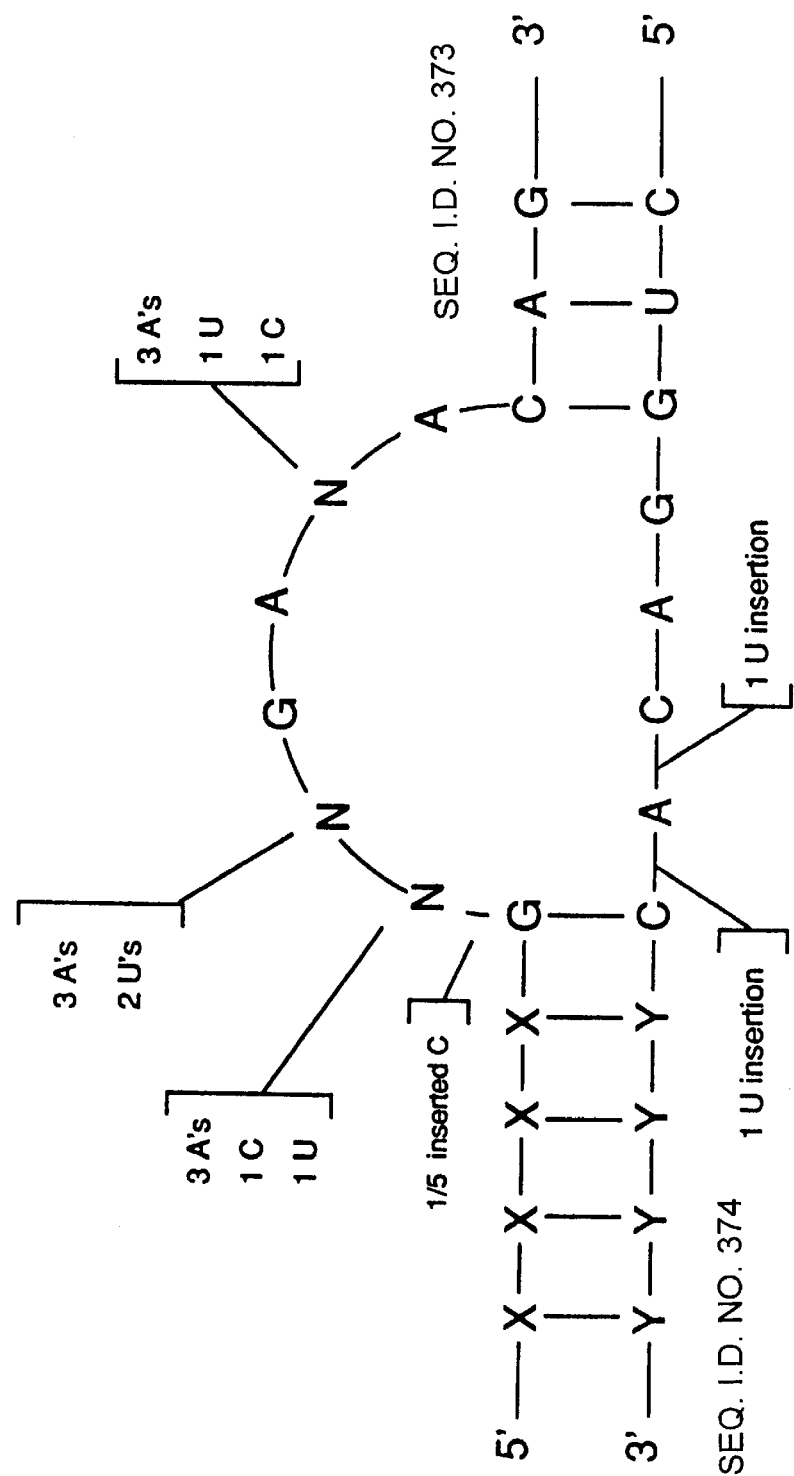

FIG. 30 shows the consensus nucleic acid ligand solution to HIV rev referred to as Motif II.

Figure 31:
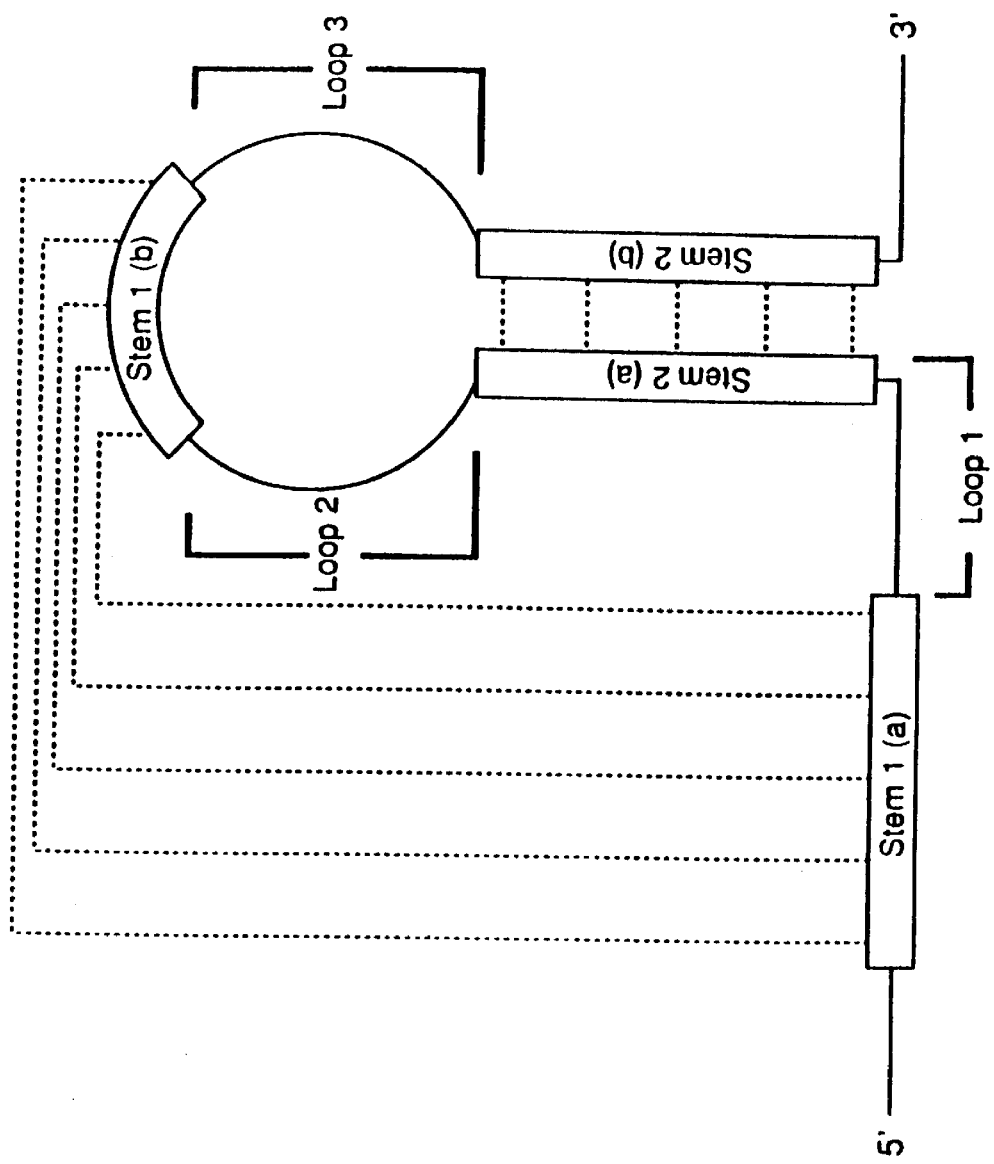

FIG. 31 is a schematic representation of a pseudoknot. The pseudoknot consists of two stems and three loops, referred to herein as stems $S_1$ and $S_2$ and loops 1, 2 and 3.

DETAILED DESCRIPTION OF THE INVENTION

The following terms are used herein according to the definitions.

Nucleic acid means either DNA, RNA, single-stranded or double-stranded and any chemical modifications thereof, provided only that the modification does not interfere with amplification of selected nucleic acids. Such modifications include, but are not limited to, modifications at cytosine exocyclic amines, substitution of 5-bromo-uracil, backbone modifications, methylations, unusual base-pairing combinations and the like.

Ligand means a nucleic acid that binds another molecule (target). In a population of candidate nucleic acids, a ligand is one which binds with greater affinity than that of the bulk population. In a candidate mixture there can exist more than one ligand for a given target. The ligands can differ from one another in their binding affinities for the target molecule.

Candidate mixture is a mixture of nucleic acids of differing sequence, from which to select a desired ligand. The source of a candidate mixture can be from naturally-occurring nucleic acids or fragments thereof, chemically synthesized nucleic acids, enzymically synthesized nucleic acids or nucleic acids made by a combination of the foregoing techniques.

Target molecule means any compound of interest for which a ligand is desired. A target molecule can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

Partitioning means any process whereby ligands bound to target molecules, termed ligand-target pairs herein, can be separated from nucleic acids not bound to target molecules. Partitioning can be accomplished by various methods known in the art. Nucleic acid-protein pairs can be bound to nitrocellulose filters while unbound nucleic acids are not. Columns which specifically retain ligand-target pairs (or specifically retain bound ligand complexed to an attached target) can be used for partitioning. Liquid-liquid partition can also be used as well as filtration gel retardation, and density gradient centrifugation. The choice of partitioning method will depend on properties of the target and of the ligand-target pairs and can be made according to principles and properties known to those of ordinary skill in the art.

Amplifying means any process or combination of process steps that increases the amount or number of copies of a molecule or class of molecules. Amplifying RNA molecules in the disclosed examples was carried out by a sequence of three reactions: making cDNA copies of selected RNAs, using polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the initial mixture.

Specific binding is a term which is defined on a case-by-case basis. In the context of a given interaction between a given ligand and a given target, a binding interaction of ligand and target of higher affinity than that measured between the target and the candidate ligand mixture is observed. In order to compare binding affinities, the conditions of both binding reactions must be the same, and should be comparable to the conditions of the intended use. For the most accurate comparisons, measurements will be made that reflect the interaction between ligand as a whole and target as a whole. The nucleic acid ligands of the invention can be selected to be as specific as required, either by establishing selection conditions that demand the requisite specificity during SELEX, or by tailoring and modifying the ligand through "walking" and other modifications using interactions of SELEX.

Randomized is a term used to described a segment of a nucleic acid having, in principle any possible sequence over a given length. Randomized sequences will be of various lengths, as desired, ranging from about eight to more than 100 nucleotides. The chemical or enzymatic reactions by which random sequence segments are made may not yield mathematically random sequences due unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into randomized sequence, for example, by altering the molar ratios of precursor nucleoside (or deoxynucleoside) triphosphates of the synthesis reaction. A deliberate bias may be desired, for example, to approximate the proportions of individual bases in a given organism, or to affect secondary structure.

SELEXION refers to a mathematical analysis and computer simulation used to demonstrate the powerful ability of SELEX to identify nucleic acid ligands and to predict which variations in the SELEX process have the greatest impact on the optimization of the process. SELEXION is an acronym for Systematic Evolution of Ligands by EXponential enrichment with Integrated Optimization by Nonlinear analysis.

Nucleic acid antibodies is a term used to refer to a class of nucleic acid ligands that are comprised of discrete nucleic acid structures or motifs that selectively bind to target molecules. Nucleic acid antibodies may be made up of double or single stranded RNA or DNA. The nucleic acid antibodies are synthesized, and in a preferred embodiment are constructed based on a ligand solution or solutions received for a given target by the SELEX process. In many cases, the nucleic acid antibodies of the present invention are not naturally occurring in nature, while in other situations they may have significant similarity to a naturally occurring nucleic acid sequence.

The nucleic acid antibodies of the present invention include all nucleic acids having a specific binding affinity for a target, while not including the cases when the target is a polynucleotide which binds to the nucleic acid through a mechanism which predominantly depends on Watson/Crick base pairing or triple helix agents (See, Riordan, M. et al. (1991) Nature 350:442443); provided, however, that when the nucleic acid antibody is double-stranded DNA, the target is not a naturally occuring protein whose physiological function depends on specific binding to double-stranded DNA.

RNA motifs is a term generally used to describe the secondary or tertiary structure of RNA molecules. The primary sequence of an RNA is a specific string of nucleotides (A, C, G or U) in one dimension. The primary sequence does not give information on first impression as to the three dimensional configuration of the RNA, although it is the primary sequence that dictates the three dimensional configuration. In certain cases, the ligand solution obtained after performing SELEX on a given target may best be represented as a primary sequence. Although conformational information pertaining to such a ligand solution is not always ascertainable based on the results obtained by SELEX, the representation of a ligand solution as a primary sequence shall not be interpreted as disclaiming the existence of an integral tertiary structure.

The secondary structure of an RNA motif is represented by contact in two dimensions between specific nucleotides. The most easily recognized secondary structure motifs are comprised of the Watson/Crick basepairs A:U and C:G. Non-Watson/Crick basepairs, often of lower stability, have been recognized, and include the pairs G:U, A:C, G:A, and U:U. (Base pairs are shown once; in RNA molecules the base pair X:Y by convention represents a sequence in which X is 5' -to Y, whereas the base pair Y:X is also allowed.) In FIG. 13 are shown a set of secondary structures, linked by single-stranded regions; the conventional nomenclature for the secondary structures includes hairpin loops, asymmetric bulged hairpin loops, symmetric hairpin loops, and pseudoknots.

When nucleotides that are distant in the primary sequence and not thought to interact through Watson/Crick and non-Watson/Crick base pairs are in fact interacting, these interactions (which are often depicted in two dimensions) are also part of the secondary structure.

The three dimensional structure of an RNA motif is merely the description, in space, of the atoms of the RNA motif. Double-stranded RNA, fully base paired through Watson/Crick pairing, has a regular structure in three dimensions, although the exact positions of all the atoms of the helical backbone could depend on the exact sequence of bases in the RNA. A vast literature is concerned with secondary structures of RNA motifs, and those secondary structures containing Watson/Crick base pairs are thought often to form A-form double stranded helices.

From A-form helices one can extend toward the other motifs in three dimensions. Non-Watson/Crick base pairs, hairpin loops, bulges, and pseudoknots are structures built within and upon helices. The construction of these additional motifs is described more fully in the text.

The actual structure of an RNA includes all the atoms of the nucleotide of the molecule in three dimensions. A fully solved structure would include as well bound water and inorganic atoms, although such resolution is rarely achieved by a researcher. Solved RNA structures in three dimensions will include all the secondary structure elements (represented as three dimensional structures) and fixed positions for the atoms of nucleotides not restrained by secondary structure elements; due to base stacking and other forces extensive single stranded domains may have fixed structures.

Primary sequences of RNAs limit the possible three dimensional structures, as do the fixed secondary structures. The three dimensional structures of an RNA are limited by the specified contacts between atoms in two dimensions, and are then further limited by energy minimizations, the capacity of a molecule to rotate all free rotatable bonds such that the resultant molecule is more stable than other conformers having the same primary and secondary sequence and structure.

Most importantly, RNA molecules have structures in three dimensions that are comprised of a collection of RNA motifs, including any number of the motifs shown in FIG. 13.

Therefore, RNA motifs include all the ways in which it is possible to describe in general terms the most stable groups of conformations that a nucleic acid compound can form. For a given target, the ligand solution and the nucleic acid antibody may be one of the RNA motifs described herein or some combination of several RNA motifs.

Ligand solutions are defined as the three dimensional structure held in common or as a family that define the conserved components identified through SELEX. For example, the ligands identified for a particular target may contain a primary sequence in common (NNNCGNAANUCGN'N'N) (SEQ ID NO:1) which can be represented by a hairpin in two dimensions by:

The three dimensional structure would thus be insensitive to the exact sequence of three of the five base pairs and two of the five loop nucleotides, and would in all or most versions of the sequence/structure be an appropriate ligand for further use. Thus ligand solutions are meant to represent a potentially large collection of appropriate sequence/structures, each identified by the family description which is inclusive of all exact sequence/structure solutions. It is further contemplated through this definition that ligand solutions need not include only members with exact numerical equivalency between the various components of an RNA motif. Some ligands may have loops, for example, of five nucleotides while other ligands for the same target may contain fewer or more nucleotides in the equivalent loop and yet be included in the description of the ligand solution.

Although the ligand solution derived by SELEX may include a relatively large number of potential members, the ligand solutions are target specific and, for the most part, each member of the ligand solution family can be used as a nucleic acid antibody to the target. The selection of a specific member from a family of ligand solutions to be employed as a nucleic acid antibody can be made as described in the text and may be influenced by a number of practical considerations that would be obvious to one of ordinary skill in the art.

The method of the present invention developed in connection with investigations of translational regulation in bacteriophage T4 infection. Autoregulation of the synthesis of certain viral proteins, such as the bacteriophage T4 DNA polymerase (gp43), involves binding of the protein to its own message, blocking its translation. The SELEX method was used to elucidate the sequence and structure requirements of the gp43 RNA binding site. SELEX allowed the rapid selection of preferred binding sequences from a population of random nucleic acid sequences. While exemplified by the isolation and identification of nucleic acid sequences which bind to proteins known to bind to RNA, the method of the present invention is generally applicable to the selection of a nucleic acid capable of binding any given protein. The method is applicable to selection of nucleic acids which bind to proteins which do not (or are not known to) bind to nucleic acid as a part of their natural activity or biological function. The SELEX method requires no knowledge of the structure or sequence of a binding site and no knowledge of the structure or sequence of the target protein. The method does not depend on purified target protein for selections. In general, application of SELEX will enrich for ligands of the most abundant target. In a mixture of ligands, techniques for isolating the ligand of a given target are available. For example, another ligand (e.g., substrate, inhibitor, antibody) of the desired target can be used to compete specifically for binding the target, so that the desired nucleic acid ligand can be partitioned from ligands of other targets.

In the preferred embodiment, ligands derived by SELEX are comprised of single stranded RNA sequences. It is a critical element of this invention that the present inventors were able to make conclusions about RNA that are contrary to those commonly held in the field, and to use these conclusions to tailor the SELEX process to achieve nucleic acid antibodies derived from ligand solutions.

RNA was first appreciated as an information messenger between the DNA sequences that are the genes and the protein sequences that are found within enzymes and other proteins. From the first moments after Watson and Crick described the structure of DNA and the connection between DNA sequence and protein sequence, the means by which proteins were synthesized became central to much experimental biochemistry. Eventually messenger RNA (mRNA) was identified as the chemical intermediate between genes and proteins. A majority of RNA species present in organisms are mRNAs, and thus RNA continues to be seen largely as an informational molecule. RNA serves its role as an informational molecule largely through the primary sequence of nucleotides, in the same way that DNA serves its function as the material of genes through the primary sequence of nucleotides; that is, information in nucleic acids can be represented in one dimension.

As the biochemistry of gene expression was studied, several RNA molecules within cells were discovered whose roles were not informational. Ribosomes were discovered to be the entities upon which mRNAs are translated into proteins, and ribosomes were discovered to contain essential RNA (ribosomal RNAs, or rRNAs). rRNAs for many years were considered to be structural, a sort of scaffold upon which the protein components of the ribosome were "hung" so as to allow the protein components of the ribosome to perform the protein synthetic action of the ribosome. An additional large class of RNAs, the transfer RNAs (tRNAs), were postulated and found. tRNAs are the chemically bifunctional adapters that recognize codons within mRNA and carry the amino acids that are condensed into protein. Most importantly, even though a tRNA structure was determined by X-ray analysis in 1974, RNAs were considered to be primarily "strings" in one dimension for an additional decade. rRNA occupied a strange position in the research community. For a long period almost no one sensed the reason behind the deep similarities in rRNAs from various species, and the true chemical capacity of RNA molecules. Several researchers postulated that RNA might once have served an enzymatic rather than informational role, but these postulates were never intended to be predictive about present functions of RNA.

Tom Cech's work on ribozymes—a new class of RNA molecules—expanded the view of the functional capacity of RNA. The group I introns are able to splice autocatalytically, and thus at least some limited catalysis is within the range of RNA. Within this range of catalysis is the activity of the RNA component of RNase P, an activity discovered by Altman and Pace. Cech and Altman received the Nobel Prize in Chemistry for their work, which fundamentally changed the previous limitations for RNA molecules to informational roles. rRNAs, because of the work of Cech and Altman, are now thought by some to be the catalytic center of the ribosome, and are no longer thought to be merely structural.

It is a central premise of this Invention that RNA molecules remain underestimated by the research community, with respect to binding and other capacities. While ribozymes have caused a remarkable increase in research aimed at RNA functions, the present application contemplates that the shape possibilities for RNA molecules (and probably DNA as well) afford an opportunity to use SELEX to find RNAs with virtually any binding function. It is further contemplated that the range of catalytic functions possible for RNA is broad beyond the present conventional wisdom, although not necessarily as broad as that of proteins.

The three dimensional shapes of some RNAs are known directly from either X-ray diffraction or NMR methodologies. The existing data set is sparse. The structures of four tRNAs have been solved, as well as three smaller RNA molecules: two small hairpins and a small pseudoknot. The various tRNAs, while related, have elements of unique structure; for example, the anticodon bases of the elongator tRNAs are displayed toward the solvent, while the anticodon bases of an initiator tRNA are pointed more away from the solvent. Some of these differences may result from crystal lattice packing forces, but some are also no doubt a result of idiosyncratic energy minimization by different single stranded sequences within homologous secondary and three dimensional structures.

Sequence variations of course are vast. If a single stranded loop of an RNA hairpin contains eight nucleotides, 65,536 different sequences comprise the saturated sequence "space." Although not bound to the theory of this assertion, the inventors of this invention believe that each member of that set will have, through energy minimization, a most stable structure, and the bulk of those structures will present subtly distinct chemical surfaces to the solvent or to potential interacting target molecules such as proteins. Thus, when all 65,536 sequences within a particular structural motif were tested against the bacteriophage T4 DNA polymerase, two sequences from that set bound better than all others. This suggests that structural aspects of those two sequences are special for that target, and that the remaining 65,534 sequences are not as well suited for binding to the target. It is almost certain that within those 65,536 sequences are other individual members or sets that would be best suited for interacting with other targets.

A key concept in this description of RNA structures is that every sequence will find its most stable structure, even though RNAs are often drawn so as to suggest a random coil or floppy, unstructured element. Homopolymers of RNA, unable to form Watson/Crick base pairs, are often found to have a non-random structure attributed to stacking energy gained by fixing the positions of adjacent bases over each other. Clearly sequences involving all four nucleotides may have local regions of fixed structure, and even without Watson/Crick base pairs a non-uniform sequence may have more structure than is at first presumed. The case for fixed structures in RNA loops is even stronger. The anticodon loops of tRNAs have a structure, and so do—presumably—the two winning sequences that bind best to T4 DNA polymerase.

Antiparallel strands of complementary sequence in RNA yield A-form helices, from which loop sequences emerge and return. Even if the loop sequences do not have a strong capacity to interact, energy minimization is an energetically free structure optimization (that is, no obvious energies of activation block energy minimization of a loop sequence). A kinetically likely starting point for optimization may be the loop closing base pair of an RNA stem, which presents a flat surface upon which optimal stacking of loop nucleotides and bases may occur. Loops of RNA are in principle equivalent to loops of protein connecting antiparallel alpha-helices or beta-strands. Although these protein loops are often called random coils, they are neither random nor coiled. Such loops are called "omega" structures, reflecting that the loop emerges and returns to positions that are relatively close to each other (See, Leszczynski, J. and Rose, G. et al. (1986) Science 234:849–855); those positions in a protein are conceptually equivalent to the loop closing base pair of an RNA hairpin.

Many omega structures have been solved by X-ray diffraction, and the structures are idiosyncratic. Clearly each structure is the result of a unique energy minimization acted upon a loop whose ends are close to each other. Both in proteins and RNAs those loops will energy minimize without information from the rest of the structure except, to a first approximation, the loop closing pair of amino acids or base pair. For both protein omega loops and RNA hairpin loops all the freely rotatable bonds will participate in the attempt to minimize the free energy. RNA, it seems, will be rather more responsive to electrostatics than proteins, while proteins will have many more degrees of freedom than RNAs. Thus, calculations of RNA structures through energy minimization are more likely to yield accurate solution structures than are comparable calculations for proteins.

Single stranded regions of both RNAs and protein may be held so as to extend the possible structure. That is, if a single stranded loop emerges and returns in a protein structure from parallel strands of alpha-helix or beta-strands, the points of emergence and return are further from each other than in the omega structures. Furthermore, the distance spanned by the single strand of peptide can be varied by the lengths of parallel alpha-helix or beta-strand.

For those protein structures in which the single strand lies upon a fixed protein secondary structure, the resultant energy minimization could, in principle, allow interactions between the single stranded domain and the underlying structure. It is likely that amino acid side chains that can form salt bridges in secondary structures could do the same in extended single strands lying on top of regular secondary structures. Thus the exact structures of such protein regions will again be idiosyncratic, and very much sequence dependent. In this case the sequence dependence will include both the single strand and the underlying sequence of the secondary structure.

Interestingly, an RNA structure known as a pseudoknot is analogous to these extended protein motifs, and may serve to display toward solvent or target molecules extended single strands of RNA whose bases are idiosyncratically arrayed toward either the solvent/target or an underlying RNA secondary structure. Pseudoknots have, in common with protein motifs based on loops between parallel strands, the capacity to alter the length of single strand and the sequence of the helix upon-which it lies.

Thus, exactly like in protein motifs, by covariation with sequences in the underlying secondary structure it is possible to display single stranded nucleotides and bases toward either the solvent or the underlying structure, thus altering the electrostatics and the functional chemical groups that are interacting with targets. It is important to note that such structure variations follow from energy minimizations, but only one pseudoknot structure is known, even at low resolution. Nevertheless, the value of this Invention arises out of the recognition that the shape and functional displays possible from pseudoknots are recognized to be nearly infinite in unique qualities.

Both hairpin loops and the single stranded domain of pseudoknots are built upon antiparallel RNA helices. Helices of RNA may contain irregularities, called bulges. Bulges can exist in one strand of a helix or both, and will provide idiosyncratic structural features useful for target recognition. Additionally, helix irregularities can provide angled connections between regular helices.

A large bulge (see FIG. 13) on one strand of RNA may be comparable to hairpin loops, except that the loop closing base pair is replaced by the two base pairs flanking the bulge.

Asymmetric bulges (see FIG. 13) may provide an elongated and irregular structure that is stabilized by nucleotide contacts across the bulge. These contacts may involve Watson/Crick interactions or any other stabilizing arrangement, including other hydrogen bonds and base stacking.

Finally, when contemplating fixed RNA shapes or motifs, it is instructive to consider what substantial differences exist between RNA and proteins. Since protein is thought to have displaced RNA during evolution for those activities now carried out almost entirely by proteins and peptides, including catalysis and highly specific recognition, the chemical properties of proteins are thought to be more useful than RNA for constructing variable shapes and activities. The standard reasoning includes the existence of 20 amino acids versus only four nucleotides, the strong ionic qualities of lysine, arginine, aspartic acid, and glutamic acid which have no counterpart in the RNA bases, the relative neutrality of the peptide backbone when compared to the strongly negative sugar-phosphate backbone of nucleic acids, the existence of histidine with a pK near neutrality, the fact that the side chains of the amino acids point toward the solvent in both alpha helices and beta strands, and the regular secondary structures of proteins. In the double stranded nucleic acids, including RNA, base pairs point the bases toward each other and utilize much of the chemical information present at the one dimensional level. Thus, from every angle presently understood to contribute to shape diversity and function, proteins are thought to be the vastly superior chemical to nucleic acids, including RNA. During evolution, proteins were chosen for recognition and catalysis over RNA, thus supporting the present widely held view.

Conversely, and central to this. Invention, the vast number of sequences and shapes possible for RNA will conceivably allow, especially with sequences never tested during evolutionary history, every desired function and binding affinity even though RNA is made up of only four nucleotides and even though the backbone of an RNA is so highly charged. That is, the RNA motifs described above, with appropriate sequence specifications, will yield in space those chemical functions needed to provide tight and specific binding to most targets. It may be suggested that RNA is as versatile as the immune system. That is, while the immune system provides a fit to any desired target, RNA provides those same opportunities. The enabling methodology described herein can utilize $10^{18}$ sequences, and thus try vast numbers of structures such that whatever intrinsic advantages proteins or specifically antibodies may have over RNA are compensated for by the vastness of the possible "pool" from which RNA ligands are selected. In addition, with the use of modified nucleotides, RNA can be used that is intrinsically more chemically varied than natural RNAs.

The SELEX method involves the combination of a selection of nucleic acid ligands which bind to a target molecule, for example a protein, with amplification of those selected nucleic acids. Iterative cycling of the selection/amplification steps allows selection of one or a small number of nucleic acids which bind most strongly to the target from a pool which contains a very large number of nucleic acids.

Cycling of the selection/amplification procedure is continued until a selected goal is achieved. For example, cycling can be continued until a desired level of binding of the nucleic acids in the test mixture is achieved or until a minimum number of nucleic acid components of the mixture is obtained (in the ultimate case until a single species remains in the test mixture). In many case, it will be desired to continue cycling until no further improvement of binding is achieved. It may be the case that certain test mixtures of nucleic acids show limited improvement in binding over background levels during cycling of the selection/ amplification. In such cases, the sequence variation in the test mixture should be increased including more of the possible sequence variants or the length of the sequence randomized region should be increased until improvements in binding are achieved. Anchoring protocols and/or walking techniques can be employed as well.

Specifically, the method requires the initial preparation of a test mixture of candidate nucleic acids. The individual test nucleic acids can contain a randomized region flanked by sequences conserved in all nucleic acids in the mixture. The conserved regions are provided to facilitate amplification or selected nucleic acids. Since there are many such sequences known in the art, the choice of sequence is one which those of ordinary skill in the art can make, having in mind the desired method of amplification. The randomized region can have a fully or partially randomized sequence. Alternatively, this portion of the nucleic acid can contain subportions that are randomized, along with subportions which are held constant in all nucleic acid species in the mixture. For example, sequence regions known to bind, or selected for binding, to the target protein can be integrated with randomized regions to achieve improved binding or improved specificity of binding. Sequence variability in the test mixture can also be introduced or augmented by generating mutations in the nucleic acids in the test mixture during the selection/amplification process. In principle, the nucleic acids employed in the test mixture can be any length as long as they can be amplified. The method of the present invention is most practically employed for selection from a large number of sequence variants. Thus, it is contemplated that the present method will preferably be employed to assess binding of nucleic acid sequences ranging in length from about four bases to any attainable size.

The randomized portion of the nucleic acids in the test mixture can be derived in a number of ways. For example, full or partial sequence randomization can be readily achieved by direct chemical synthesis of the nucleic acid (or portions thereof) or by synthesis of a template from which the nucleic acid (or portions thereof) can be prepared by use of appropriate enzymes. End addition, catalyzed by terminal transferase in the presence of nonlimiting concentrations of all four nucleotide triphosphates can add a randomized sequence to a segment. Sequence variability in the test nucleic acids can also be achieved by employing size-selected fragments of partially digested (or otherwise cleaved) preparations of large, natural nucleic acids, such as genomic DNA preparations or cellular RNA preparations. In those cases in which randomized sequence is employed, it is not necessary (or possible from long randomized segments) that the test mixture contains all possible variant sequences. It will generally be preferred that the test mixture contain as large a number of possible sequence variants as is practical for selection, to insure that a maximum number of potential binding sequences are identified. A randomized sequence of 30 nucleotides will contain a calculated $10^{18}$ different candidate sequences. As a practical matter, it is convenient to sample only about $10^{18}$ candidates in a single selection. Practical considerations include the number of templates on the DNA synthesis column, and the solubility of RNA and the target in solution. (Of course, there is no theoretical limit for the number of sequences in the candidate mixture.) Therefore, candidate mixtures that have randomized segments longer than 30 contain too many possible sequences for all to be conveniently sampled in one selection. It is not necessary to sample all possible sequences of a candidate mixture to select a nucleic acid ligand of the invention. It is basic to the method that the nucleic acids of the test mixture are capable of being amplified. Thus, it is preferred that any conserved regions employed in the test nucleic acids do not contain sequences which interfere with amplification.

The various RNA motifs described above can almost always be defined by a polynucleotide containing about 30 nucleotides. Because of the physical constraints of the SELEX process, a randomized mixture containing about 30 nucleotides is also about the longest contiguous randomized segment which can be utilized while being able to test substantially all of the potential variants. It is, therefore, a preferred embodiment of this invention when utilizing a candidate mixture with a contiguous randomized region, to use a randomized sequence of at least 15 nucleotides and containing at least about $10^9$ nucleic acids, and in the most preferred embodiment contains at least 25 nucleotides.

This invention includes candidate mixtures containing all possible variations of a contiguous randomized segment of at least 15 nucleotides. Each individual member in the candidate mixture may also be comprised of fixed sequences flanking the randomized segment that aid in the amplification of the selected nucleic acid sequences.

Candidate mixtures may also be prepared containing both randomized sequences and fixed sequences wherein the fixed sequences serve a function in addition to the amplification process. In one embodiment of the invention, the fixed sequences in a candidate mixture may be selected in order to enhance the percentage of nucleic acids in the candidate mixture possessing a given nucleic acid motif. For example, the incorporation of the appropriate fixed nucleotides will make it possible to increase the percentage of pseudoknots or hairpin loops in a candidate mixture. A candidate mixture that has been prepared including fixed sequences that enhance the percentage of a given nucleic acid structural motif is, thereof ore, a part of this invention. One skilled in the art, upon routine inspection of a variety of nucleic antibodies as described herein, will be able to construct, without undue experimentation, such a candidate mixture. Examples 2 and 8 below describe specific examples of candidate mixtures engineered to maximize preferred RNA motifs.

Candidate mixtures containing various fixed sequences or using a purposefully partially randomized sequence may also be employed after a ligand solution or partial ligand solution has been obtained by SELEX. A new SELEX process may then be initiated with a candidate mixture informed by the ligand solution.

Polymerase chain reaction (PCR) is an exemplary method for amplifying of nucleic acids. Descriptions of PCR methods are found, for example in Saiki et al. (1985) Science 230:1350–1354; Saiki et al. (1986) Nature 324:163–166; Scharf et al. (1986) Science 233:1076–1078; Innis et al. (1988) Proc. Natl. Acad. Sci. 85:9436–9440; and in U.S. Pat. No. 4,683,195 (Mullis et al.) and U.S. Pat. No. 4,683,202 (Mullis et al.). In its basic form, PCR amplification involves repeated cycles of replication of a desired single-stranded DNA (or cDNA copy of an RNA) employing specific oligonucleotide primers complementary to the 3' and 5' ends of the ssDNA, primer extension with a DNA polymerase, and DNA denaturation. Products generated by extension from one primer serve as templates for extension from the other primer. A related amplification method described in PCT published application WO 89/01050 (Burg et al.) requires the presence or introduction of a promoter sequence upstream of the sequence to be amplified, to give a double-stranded intermediate. Multiple RNA copies of the double-stranded promoter containing intermediate are then produced using RNA polymerase. The resultant RNA copies are treated with reverse transcriptase to produce additional double-stranded promoter containing intermediates which can then be subject to another round of amplification with RNA polymerase. Alternative methods of amplification include among others cloning of selected DNAs or cDNA copies of selected RNAs into an appropriate vector and introduction of that vector into a host organism where the vector and the cloned DNAs are replicated and thus amplified (Guatelli, J. C. et al. (1990) Proc. Natl. Acad. Sci. 87:1874). In general, any means that will allow faithful, efficient amplification of selected nucleic acid sequences can be employed in the method of the present invention. It is only necessary that the proportionate representation of sequences after amplification at least roughly reflects the relative proportions of sequences in the mixture before amplification.

Specific embodiments of the present invention for amplifying RNAs were based on Innis et al. (1988) supra. The RNA molecules and target molecules in the test mixture were designed to provide, after amplification and PCR, essential T7 promoter sequences in their 5' portions. Full-length cDNA copies of selected RNA molecules were made using reverse transcriptase primed with an ologimer complementary to the 3' sequences of the selected RNAs. The resultant cDNAS were amplified by Tag DNA polymerase chain extension, providing the T7 promoter sequences in the selected DNAs. Double-stranded products of this amplification proces were then transcribed in vitro. Transcripts were used in the next selection/amplification cycle. The method can optionally include appropriate nucleic acid purification steps.

In general any protocol which will allow selection of nucleic acids based on their ability to bind specifically to another molecule, i.e., a protein or in the most general case any target molecule, can be employed in the method of the present invention. It is only necessary that the selection partition nucleic acids which are capable of being amplified. For example, a filter binding selection, as described in Example 1, in which a test nucleic acid mixture is incubated with target protein, the nucleic acid/protein mixture is then filtered through a nitrocellulose filter and washed with appropriate buffer to remove free nucleic acids. Protein/nucleic acid often remain bound to the filter. The relative concentrations of protein to test nucleic acid in the incubated mixture influences the strength of binding that is selected for. When nucleic acid is in excess, competition for available binding sites occurs and those nucleic acids which bind most strongly are selected. Conversely, when an excess of protein is employed, it is expected that any nucleic acid that binds to the protein will be selected. The relative concentrations of protein to nucleic acid employed to achieve the desired selection will depend on the type of protein, the strength of the binding interaction and the level of any background binding that is present. The relative concentrations needed to achieve the desired selection result can be readily determined empirically without under experimentation. Similarly, it may be necessary to optimize the filter washing procedure to minimize background binding. Again such optimization of the filter washing procedures is within the skill of the ordinary artisan.

A mathematical evaluation of SELEX referred to as SELEXION has been utilized by the inventors of the present invention. Appendix A to this application includes a brief review of the mathematical analysis utilized to obtain generalizations regarding SELEX derived from SELEXION.

The generalizations obtained from SELEXION are as follows: 1) The likelihood of recovering the best-binding RNA in each round of SELEX increases with the number of such molecules present, with their binding advantage versus the bulk RNA pool, and with the total amount of protein used. Although it is not always intuitively obvious to know in advance how to maximize the difference in binding, the likelihood of recovering the best-binding RNA still can be increased by maximizing the number of RNA molecules and target molecules sampled; 2) the ideal nucleic acid and protein concentrations to be used in various rounds of SELEX are dependent on several factors. The experimental parameters suggested by SELEXION parallel those employed in the Examples hereto. For example, when the relative affinity of the ultimate ligand solution is not known—which will almost inevitably be the case when SELEX is performed—it is preferred that the protein and nucleic acid candidate mixture concentrations are selected to provide a binding between about 3 and 7 percent of the total of nucleic acids to the protein target. By using this criterion it can be expected that a tenfold to twentyfold enrichment in high affinity ligands will be achieved in each round of SELEX.

The experimental conditions used to select nucleic acid ligands to various targets in the preferred embodiment are to be selected to mimic the environment that the target would be found in vivo. Example 10 below indicates how changing the selection conditions will effect the ligand solution received to a particular target. Although the ligand solution to NGF had significant similarities under high and low salt conditions, differences were observed. Adjustable conditions that may be altered to more accurately reflect the in vivo environment of the target include, but are not limited to, the total ionic strength, the concentration of bivalent cations and the pH of the solution. One skilled in the art would be able to easily select the appropriate separation conditions based on a knowledge of the given target.

In order to proceed to the amplification step, selected nucleic acids must be released from the target after partitioning. This process must be done without chemical degradation of the selected nucleic acids and must result in amplifiable nucleic acids. In a specific embodiment, selected RNA molecules were eluted from nitrocellulose filters using a freshly made solution containing 200 $\mu$l of a 7M urea, 20 mM sodium citrate (pH 5.0), 1 mM EDTA solution combined with 500 $\mu$l of phenol (equilibrated with 0.1 M sodium acetate pH 5.2). A solution of 200 $\mu$l 7M urea with 500 $\mu$l of phenol has been successfully employed. The eluted solution of selected RNA was then extracted with ether, ethanol precipitated and the precipitate was resuspended in water. A number of different buffer conditions for elution of selected RNA from the filters can be used. For example, without limitation nondetergent aqueous protein denaturing agents such as quanidinium chloride, quanidinium thiocyanate, etc., as are known in the art, can be used. The specific solution used for elution of nucleic acids from the filter can be routinely selected by one of ordinary skill in the art.

Alternative partitioning protocols for separating nucleic acids bound to targets, particularly proteins, are available to the art. For example, binding and partitioning can be achieved by passage of the test nucleic acid mixture through a column which contains the target molecule bound to a solid support material. Those nucleic acid that bind to the target will be retained on the column and unbound nucleic acids can be washed from the column.

Throughout this application, the SELEX process has been defined as an iterative process wherein selection and amplification are repeated until a desired selectivity has been attained. In one embodiment of the invention, the selection process may be efficient enough to provide a ligand solution after only one separation step. For example, in theory a column supporting the target through which the candidate mixture is introduced—under the proper conditions and with a long enough column—should be capable of separating nucleic acids based on affinity to the target sufficiently to obtain a ligand solution. To the extent that the original selection step is sufficiently selective to yield a ligand solution after only one step, such a process would also be included within the scope of this invention.

In one embodiment of this invention, SELEX is iteratively performed until a single or a discrete small number of nucleic acid ligands remain in the candidate mixture following amplification. In such cases, the ligand solution will be represented as a single nucleic acid sequence, and will not include a family of sequences having comparable binding affinities to the target.

In an alternate embodiment of the invention, SELEX iterations are terminated at some point when the candidate mixture has been enriched in higher binding affinity nucleic acid ligands, but still contains a relatively large number of distinct sequences. This point can be determined by one of skill in the art by periodically analyzing the sequence randomness of the bulk candidate mixture, or by assaying bulk affinity to the target.

At this time, SELEX is terminated, and clones are prepared and sequenced. Of course, there will be an almost unlimited number of clones that could be sequenced. As seen in the Examples below, however, after sequencing between 20 and 50 clones it is generally possible to detect the most predominant sequences and defining characteristics of the ligand solution. In a hypothetical example, after cloning 30 sequences it will be found that 6 sequences are identical, while certain sequence portions of 20 of the other sequences are closely related to sequences within the "winning" sequence. Although the most predominant sequence may be considered a ligand solution to that target, it is often more appropriate to construct or describe a ligand solution that consists of a family of sequences that includes the common characteristics of many of the cloned sequences.

In a further embodiment of this invention, a ligand solution that is represented as a family of sequences having a number of defining characteristics (e.g., where the ligand solution is AAGUNNGUNNCNNNN (SEQ ID NO:2), where N can apparently be any of the four nucleotides) may be used to initiate an additional SELEX process. In this embodiment, the candidate mixture would be comprised of partially fixed and partially random nucleotides, the fixed nucleotides being selected based on the ligand solution received in the initial SELEX process. In this manner, if there is a single nucleotide sequence that binds better than the other members of the ligand solution family, it will be quickly identified.

In an alternate further embodiment of the invention, a second SELEX experiment based on the ligand solution received in a SELEX process is also utilized. In this embodiment, the single most predominant sequence (e.g., AAGUCCGUAACACAC) (SQ ID NO:3) is used to inform the second SELEX process. In this second SELEX process the candidate mixture is prepared in order to yield sequences based on the selected winner, while assuring that there will be sufficient randomization at each of the sequences. This candidate mixture may be produced by using nucleotide starting materials that are biased rather than randomized. For example, the A solution contains 75% A and 25% U, C and G. Although the nucleic acid synthesizer is set to yield the predominant nucleotide, the presence of the other nucleotides in the A solution will yield nucleic acid sequences that are predominant in A but that will also yield variations in this position. Again, this second SELEX round, informed by the results obtained in the initial SELEX process, will maximize the probabilities of obtaining the best ligand solution to a given target. Again, it must be clarified that the ligand solution may consist of a single preferred nucleic acid ligand, or it may consist of a family of structurally related sequences with essentially similar binding affinities.

In practice, it may occasionally be preferred that the SELEX process not be performed until a single sequence is obtained. The SELEX process contains several bias points that may affect the predominance of certain sequences in a candidate mixture after several rounds of. SELEX that are not related to the binding affinity of that sequence to the target. For example, a bias for or against certain sequences may occur during the production of cDNA from the RNA recovered after selection, or during the amplification process. The effects of such unpredictable biases can be minimized by halting SELEX prior to the time that only one or a small number of sequences predominate in the reaction mixture.

As stated above, sequence variation in the test nucleic acid mixture can be achieved or increased by mutation. For example, a procedure has been described for efficiently mutagenizing nucleic acid sequences during PCR amplification (Leung et al. 1989). This method or functionally equivalent methods can optionally be combined with amplification procedures in the present invention.

Alternatively conventional methods of DNA mutagenesis can be incorporated into the nucleic acid amplification procedure. Applicable mutagenesis procedures include, among others, chemically induced mutagenesis and oligonucleotide site-directed mutagenesis.

The present invention can also be extended to utilize additional interesting capacities of nucleic acids and the manner in which they are known or will later be found to interact with targets such as proteins. For example, a SELEX methodology may be employed to screen for ligands that form Michael adducts with proteins. Pyrimidines, when they sit in the correct place within a protein, usually adjacent to a critical cysteine or other nucleophile, can react with that nucleophile to form a Michael adduct. The mechanism by which Michael adducts are formed involves a nucleophilic attack at the 6 position of the pyrimidine base to create a transient (but slowly reversing) intermediate that is really a 5,6 dihydropyrimidine. It is possible to test for the presence of such intermediates by observing whether binding between an RNA and a protein target occurs even after the protein is denatured with any appropriate denaturant. That is, one searches for a continued covalent interaction when the binding pocket of the target has been destroyed. However, Michael adducts are often reversible, and sometimes so quickly that the failure to identify a Michael adduct through this test does not indicate that one was not present at a prior moment.

SELEX may be done so as to take advantage of Michael adduct formation in order to create very high affinity, near-suicide substrates for an enzyme or other protein target. Imagine that after binding between a randomized mixture of RNAs and the target, prior to partitioning on a filter or by other means, the target is denatured. Subsequent partitioning, followed by reversal of the Michael adduct and cDNA synthesis on the released RNA, followed by the rest of the SELEX cycle, will enrich for RNAs that bind to a target prior to denaturation but continue to bind covalently until the Michael adduct is reversed by the scientist. This ligand, in vivo, would have the property of permanently inhibiting the target protein. The protein tRNA-uracil methyl transferase (RUMT) binds substrate tRNAs through a Michael adduct. When RUMT is expressed at high levels in *E. coli* the enzyme is found largely covalently bound to RNA, suggesting strongly that nearly irreversible inhibitors can be found through SELEX.

The method of the present invention has multiple applications. The method can be employed, for example, to assist in the identification and characterization of any protein binding site for DNA or RNA. Such binding sites function in transcriptional or translational regulation of gene expression, for example as binding sites for transcriptional activators or repressors, transcription complexes at promoter sites, replication accessory proteins and DNA polymerases at or near origins of replication and ribosomes and translational repressors at ribosome binding sites. Sequence information of such binding sites can be used to isolate and identify regulatory regions bypassing more labor intensive methods of characterization of such regions. Isolated DNA regulatory regions can be employed, for example, in heterologous constructs to selectively alter gene expression.

It is an important and unexpected aspect of the present invention that the methods described herein can be employed to identify, isolate or produce nucleic acid molecules which will bind specifically to any desired target molecule. Thus, the present methods can be employed to produce nucleic acids specific for binding to a particular target. Such a nucleic acid ligand in a number of ways functionally resembles an antibody. Nucleic acid ligands which have binding functions similar to those of antibodies can be isolated by the methods of the present invention. Such nucleic acid ligands are designated herein nucleic acid antibodies and are generally useful in applications in which polyclonal or monoclonal antibodies have found application. Nucleic acid antibodies can in general be substituted for antibodies in any in vitro or in vivo application. It is only necessary that under the conditions in which the nucleic acid antibody is employed, the nucleic acid is substantially resistant to degradation. Applications of nucleic acid antibodies include the specific, qualitative or quantitative detection of target molecules from any source; purification of target molecules based on their specific binding to the nucleic acid; and various therapeutic methods which rely on the specific direction of a toxin or other therapeutic agent to a specific target site.

Target molecules are preferably proteins, but can also include among others carbohydrates, peptidoglycans and a variety of small molecules. As with conventional proteinaceous antibodies, nucleic acid antibodies can be employed to target biological structures, such as cell surfaces or viruses, through specific interaction with a molecule that is an integral part of that biological structure. Nucleic acid antibodies are advantageous in that they are not limited by self tolerance, as are conventional antibodies. Also nucleic acid antibodies do not require animals or cell cultures for synthesis or production, since SELEX is a wholly in vitro process. As is well-known, nucleic acids can bind to complementary nucleic acid sequences. This property of nucleic acids has been extensively utilized for the detection, quantitation and isolation of nucleic acid molecules. Thus, the methods of the present invention are not intended to encompass these well-known binding capabilities between nucleic acids. Specifically, the methods of the present invention related to the use of nucleic acid antibodies are not intended to encompass known binding affinities between nucleic acid molecules. A number of proteins are known to function via binding to nucleic sequences, such as regulatory proteins which bind to nucleic acid operator sequences. The known ability of certain nucleic acid binding proteins to bind to their natural sites, for example, has been employed in the detection, quantitation, isolation and purification of such proteins. The methods of the present invention related to the use of nucleic acid antibodies are not intended to encompass the known binding affinity between nucleic acid binding proteins and nucleic acid sequences to which they are known to bind. However, novel, non-naturally-occurring sequences which bind to the same nucleic acid binding proteins can be developed using SELEX. It should be noted that SELEX allows very rapid determination of nucleic acid sequences that will bind to a protein and, thus, can be readily employed to determine the structure of unknown operator and binding site sequences which sequences can then be employed for applications as described herein. It is believed that the present invention is the first disclosure of the general use of nucleic acid molecules for the detection, quantitation, isolation and purification of proteins which are not known to bind nucleic acids. As will be discussed below, certain nucleic acid antibodies isolatable by SELEX can also be employed to affect the function, for example inhibit, enhance or activate the function, of specific target molecules or structures. Specifically, nucleic acid antibodies can be employed to inhibit, enhance or activate the function of proteins.

Proteins that have a known capacity to bind nucleic acids (such as DNA polymerases, other replicases, and proteins that recognize sites on RNA but do not engage in further catalytic action) yield, via SELEX, high affinity RNA ligands that bind to the active site of the target protein. Thus, in the case of HIV-1 reverse transcriptase the resultant RNA ligand (called 1.1 in Example 2) blocks cDNA synthesis in the presence of a primer DNA, an RNA template, and the four deoxynucleotide triphosphates.

The inventors theory of RNA structures suggests that nearly every protein will serve as a target for SELEX. The initial experiments against non-nucleic acid binding protein were performed with three proteins not thought to interact with nucleic acids in general or RNA in particular. The three proteins were tissue plasminogen activator (tPA), nerve growth factor (NGF), and the extracellular domain of the growth factor receptor (gfR-Xtra). All of these proteins were tested to see if they would retain mixed randomized RNAs on a nitrocellulose filter. tPA and NGF showed affinity for randomized RNA, with Kd's just below uM. gfR-Xtra did not bind with measurable affinity, suggesting that if an RNA antibody exists for that protein it must bind to a site that has no affinity for most other RNAs.

tPA and NGF were taken through the SELEX drill using RNAs with 30 randomized positions. Both tPA and NGF gave ligand solutions in the SELEX drill, suggesting that some site on each protein bound the winning sequences more tightly than that site (or another site) bound other RNAs. The winning sequences are different for the two proteins.

Since tPA and NGF worked so well in the SELEX drill, a random collection of proteins and peptides were tested to see if they had any affinity for RNA. It was reasoned that if a protein has any affinity for RNA that the SELEX drill will, on the average, yield higher affinity sequences which contact the same region of the target that provides the low, generalized affinity. A set of proteins and peptides, were tested to see if randomized RNAs (containing 40 randomized positions) would be retained on nitrocellulose filters. About two thirds of the proteins tested bound RNA, and a few proteins bound RNA very tightly. See Example 9.

Proteins that do not bind RNA to nitrocellulose filters may fail for trivial reasons having nothing to do with the likelihood of raising RNA antibodies. One example, bradykinin, fails to bind to nitrocellulose filters, and thus would fail in the above experiment. A bradykinin linked to a solid matrix through the amino terminus of the peptide was prepared, and then found that randomized RNA bound tightly to the matrix (see Example 7). Thus in the initial experiments two short peptides, bradykinin and bombesin, bind randomized RNAs quite tightly. Any high affinity RNA ligand obtained through SELEX with these peptide targets would, perhaps, be an antagonist of these active peptides, and might be useful therapeutically. It is difficult to imagine an RNA of about 30 nucleotides binding to a very small peptide without rendering that peptide inactive for virtually any activity.

As described in Examples 4, 7, 9 and 10 below, proteins not thought to interact with nucleic acids in nature were found to bind a random mixture of nucleic acids to a non-trivial extent. It has further been shown that for such proteins that were found to bind RNA mixtures non-specifically that a ligand solution can be obtained following SELEX. It is, therefore, a potentially valuable screen—prior to the performance of SELEX—to determine if a given target shows any binding to a random mixture of nucleic acids.

It is a second important and unexpected aspect of the present invention that the methods described herein can be employed to identify, isolate or produce nucleic acid molecules which will bind specifically to a particular target molecule and affect the function of that molecule. In this aspect, the target molecules are again preferably proteins, but can also include, among others, carbohydrates and various small molecules to which specific nucleic acid binding can be achieved. Nucleic acid ligands that bind to small molecules can affect their function by sequestering them or by preventing them from interacting with their natural ligands. For example, the activity of an enzyme can be affected by a nucleic acid ligand that binds the enzyme's substrate. Nucleic acid ligands, i.e., nucleic acid antibodies, of small molecules are particularly useful as reagents for diagnostic tests, (or other quantitative assays). For example, the presence of controlled substances, bound metabolites or abnormal quantities of normal metabolites can be detected and measured using nucleic acid ligands of the invention. A nucleic acid ligand having catalytic activity can affect the function of a small molecule by catalyzing a chemical change in the target. The range of possible catalytic activities is at least as broad as that displayed by proteins. The strategy of selecting a ligand for a transition state analog of a desired reaction is one method by which catalytic nucleic acid ligands can be selected.

It is believed that the present invention for the first time discloses the general use of nucleic acid molecules to effect, inhibit or enhance protein function. The binding selection methods of the present invention can be readily combined with secondary selection or screening methods for modifying target molecule function on binding to selected nucleic acids. The large population of variant nucleic acid sequences that can be tested by SELEX enhances the probability that nucleic acid sequences can be found that have a desired binding capability and function to modify target molecule activity. The methods of the present invention are useful for selecting nucleic acid ligands which can selectively affect function of any target protein including proteins which bind nucleic acids as part of their natural biological activity and those which are not known to bind nucleic acid as part of their biological function. The methods described herein can be employed to isolate or produce nucleic acid ligands which bind to and modify the function of any protein which binds a nucleic acid, either DNA or RNA, either single-stranded or double-stranded; a nucleoside or nucleotide including those having purine or pyrimidine bases or bases derived therefrom, specifically including those having adenine, thymine, guanine, uracil, cytosine and hypoxanthine bases and derivatives, particularly methylated derivatives, thereof; and coenzyme nucleotides including among others nicotinamide nucleotides, flavin-adenine dinucleotides and coenzyme A. It is contemplated that the method of the present invention can be employed to identify, isolate or produce nucleic acid molecules which will affect catalytic activity of target enzymes, i.e., inhibit catalysis or modify substrate binding, affect the functionality of protein receptors, i.e., inhibit binding to receptors or modify the specificity of binding to receptors; affect the formation of protein multimers, i.e., disrupt quaternary structure of protein subunits; and modify transport properties of protein, i.e., disrupt transport of small molecules or ions by proteins.

The SELEX process is defined herein as the iterative selection and amplification of a candidate mixture of nucleic acid sequences repeated until a ligand solution has been obtained. A further step in the process is the production of nucleic acid antibodies to a given target. Even when the ligand solution derived for a given process is a single sequence, the nucleic acid antibody containing just the ligand solution must be synthesized. For example, a SELEX experiment may give a preferred single ligand solution that consists of only 20 of the 30 randomized nucleotide sequences used in the SELEX candidate mixture. The therapeutically valuable nucleic acid antibody would not, preferably, contain the 10 non-critical nucleotides or the fixed sequences required for the amplification step of SELEX. Once the desired structure of the nucleic acid antibody is determined based on the ligand solution, the actual synthesis of the nucleic acid antibody will be performed according to a variety of techniques well known in the art.

The nucleic acid antibody may also be constructed based on a ligand solution for a given target that consists of a family of sequences. In such case, routine experimentation will show that a given sequence is preferred due to circumstances unrelated to the relative affinity of the ligand solution to the target. Such considerations would be obvious to one of ordinary skill in the art.

In an alternate embodiment of the present invention, the nucleic acid antibody may contain a plurality of nucleic acid ligands to the same target. For example, SELEX may identify two discrete ligand solutions. As the two ligand solutions may bind the target at different locations, the nucleic acid antibody may preferably contain both ligand solutions. In another embodiment, the nucleic acid antibody may contain more than one of a single ligand solution. Such multivalent nucleic acid antibodies will have increased binding affinity to the target unavailable to an equivalent nucleic acid antibody having only one ligand.

In addition, the nucleic acid antibody may also contain other elements, that will 1) add independent affinity for the target to the nucleic acid antibody; 2) dependently enhance the affinity of the nucleic acid ligand to the target; 3) direct or localize the nucleic acid antibody to the proper location in vivo where treatment is desired; or 4) utilize the specifity of the nucleic acid ligand to the target to effect some additional reaction at that location.

The methods of the present invention are useful for obtaining nucleic acids which will inhibit function of a target protein, and are particularly useful for obtaining nucleic acids which inhibit the function of proteins whose function involves binding to nucleic acid, nucleotides, nucleosides and derivatives and analogs thereof. The methods of the present invention can provide nucleic acid inhibitors, for example, of polymerases, reverse transcriptases, and other enzymes in which a nucleic acid, nucleotide or nucleoside is a substrate or co-factor.

Secondary selection methods that can be combined with SELEX include among others selections or screens for enzyme inhibition, alteration of substrate binding, loss of functionality, disruption of structure, etc. Those of ordinary skill in the art are able to select among various alternatives those selection or screening methods that are compatible with the methods described herein.

It will be readily apparent to those of skill in the art that in some cases, i.e., for certain target molecules or for certain applications, it may be preferred to employ RNA molecules in preference to DNA molecules as ligands, while in other cases DNA ligands may be preferred to RNA.

The selection methods of the present invention can also be employed to select nucleic acids which bind specifically to a molecular complex, for example to a substrate/protein or inhibitor/protein complex. Among those nucleic acids that bind specifically to the complex molecules, but not the uncompleted molecules there are nucleic acids which will inhibit the formation of the complex. For example, among those nucleic acids ligands which are selected for specific binding to a substrate/enzyme complex there are nucleic acids which can be readily selected which will inhibit substrate binding to the enzyme and thus inhibit or disrupt catalysis by the enzyme.

Figure 9:
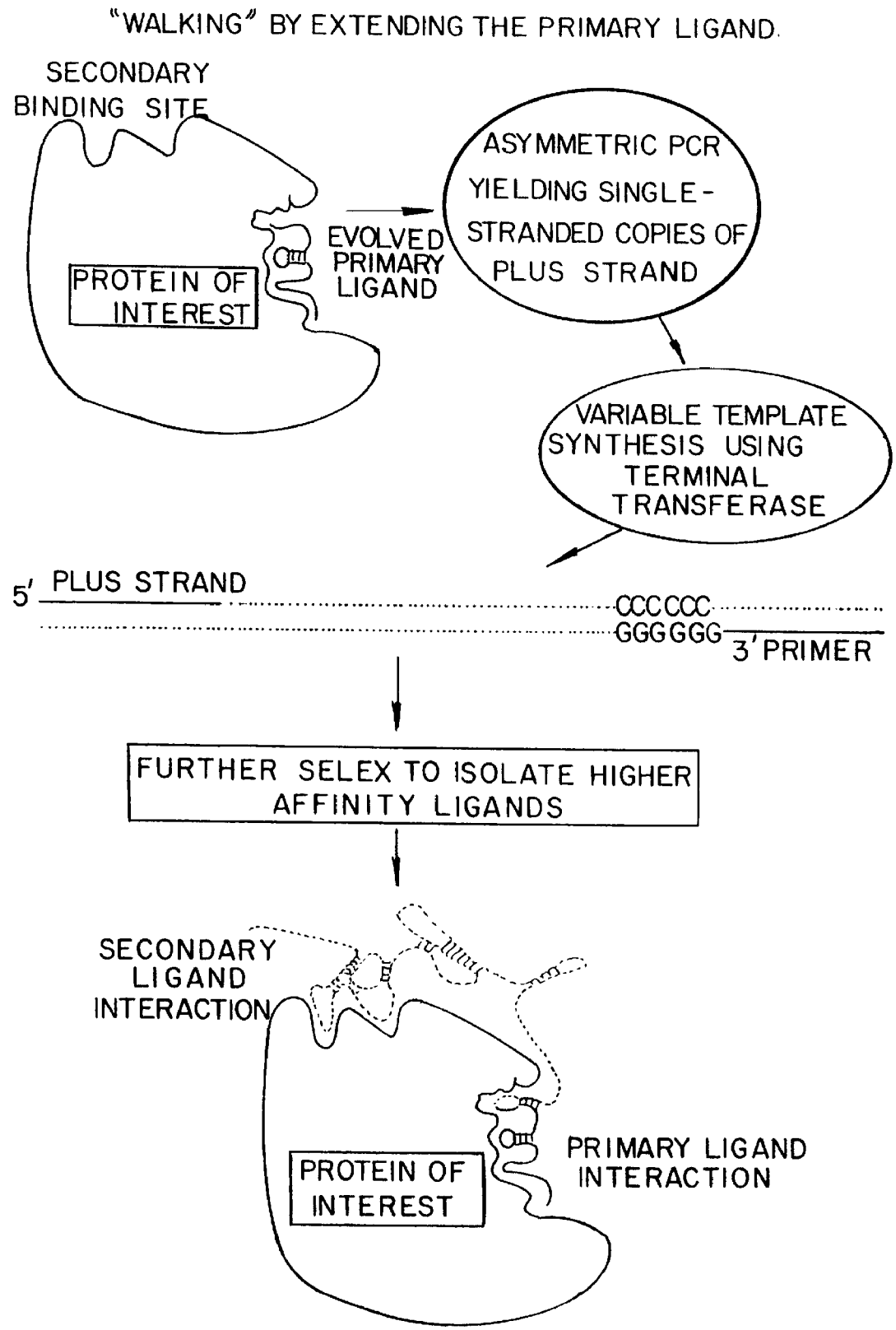
FIG. 9 is a diagram showing a process using SELEX to select a large nucleic acid ligand having two spatially separate binding interactions with a target protein. The process is termed "walking" since it includes two stages, the second being an extension of the first. The upper part of the figure depicts a target ("protein of interest") with a bound nucleic acid ligand selected by a first round of SELEX ("evolved primary ligand") bound to the protein at a first binding site. A reaction catalyzed by terminal transferase extends the length of the evolved primary ligand and generates a new set of randomized sequence candidates having a conserved region containing the primary ligand. The lower part of the figure depicts the result of a second round of SELEX based upon improved binding that results from the secondary ligand interaction at the secondary binding site of the protein. The terms "primary" and "secondary" are merely operative terms that do not imply that one has higher affinity than the other.
Figure 11:
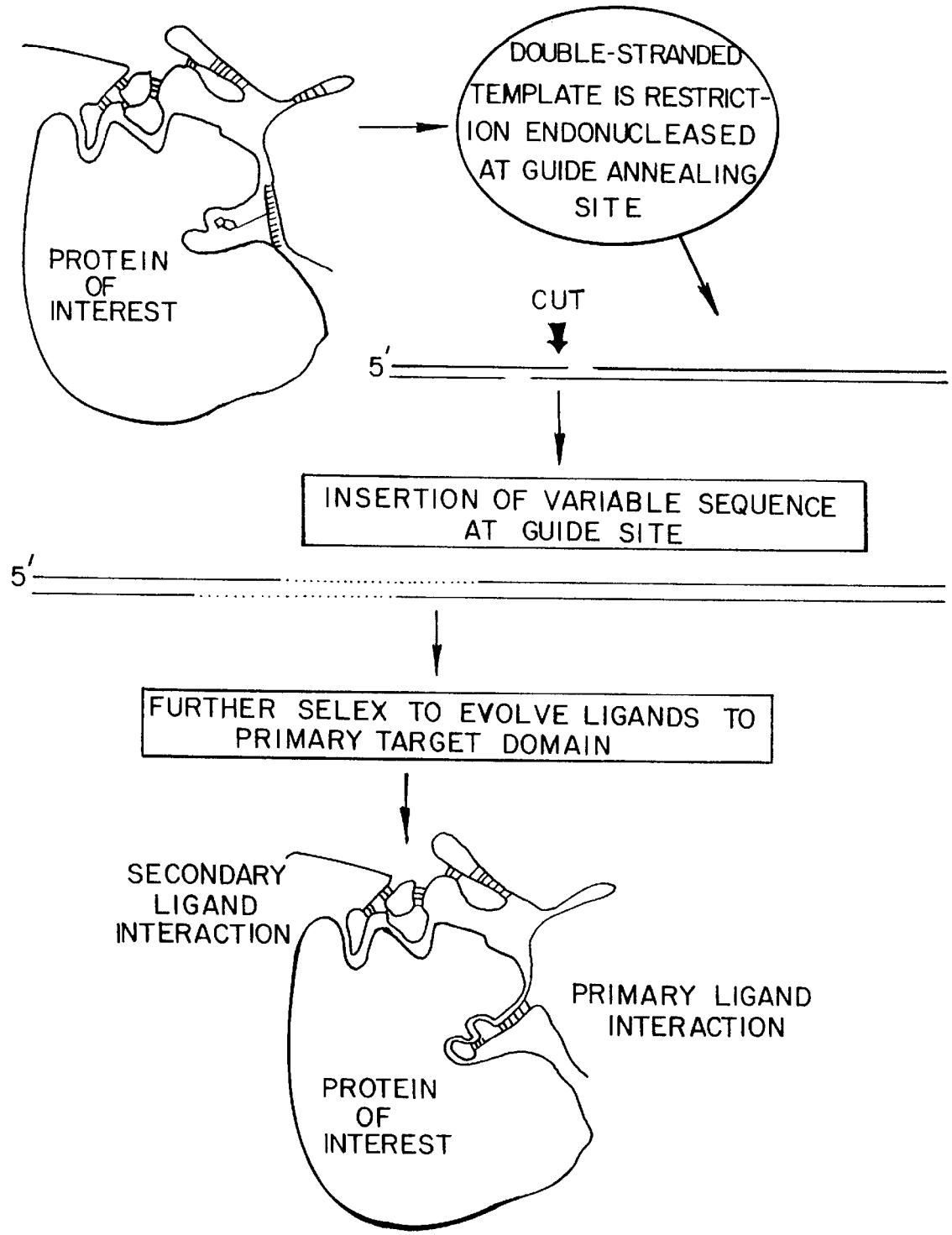
Figure 12B:
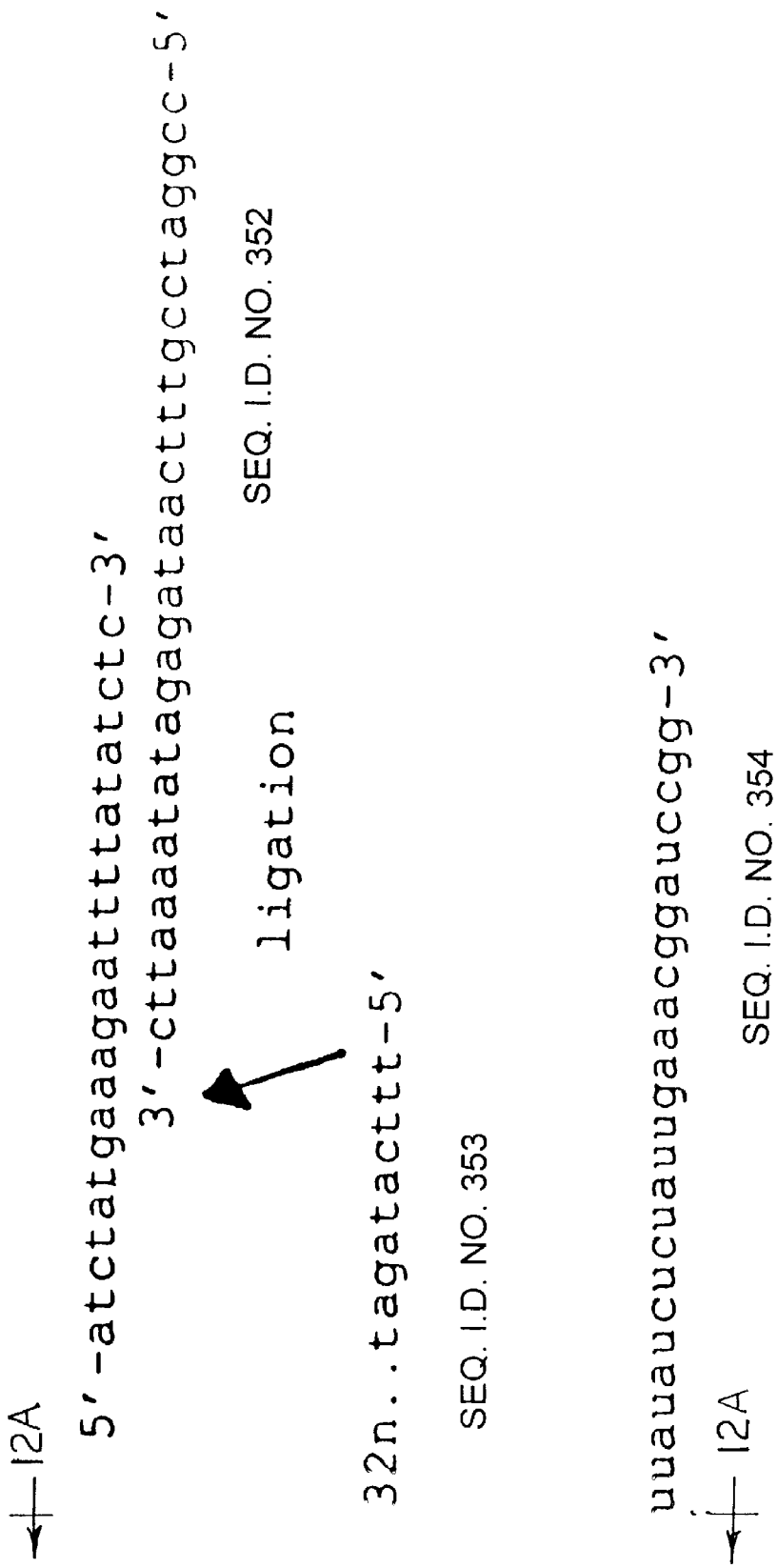
FIG. 12 shows the sequence and placement of oligomers used to construct the candidate mixture used in Example 2.

An embodiment of the present invention, which is particularly useful for the identification or isolation of nucleic acids which bind to a particular functional or active site in a protein, or other target molecule, employs a molecule known, or selected, for binding to a desired site within the target protein to direct the selection/amplification process to a subset of nucleic acid ligands that bind at or near the desired site within the target molecule. In a simple example, a nucleic acid sequence known to bind to a desired site in a target molecule is incorporated near the randomized region of all nucleic acids being tested for binding. SELEX is then used (FIG. 9) to select those variants, all of which will contain the known binding sequence, which bind most strongly to the target molecule. A longer binding sequence, which is anticipated to either bind more strongly to the target molecule or more specifically to the target can thus be selected. The longer binding sequence can then be introduced near the randomized region of the nucleic acid test mixture and the selection/amplification steps repeated to select an even longer binding sequence. Iteration of these steps (i.e., incorporation of selected sequence into test mixtures followed by selection/amplification for improved or more specific binding) can be repeated until a desired level of binding strength or specificity is achieved. This iterative "walking" procedure allows the selection of nucleic acids highly specific for a particular target molecule or site within a target molecule. Another embodiment of such an iterative "walking" procedure, employs an "anchor" molecule which is not necessarily a nucleic acid (see FIGS. 10 and 11). In this embodiment a molecule which binds to a desired target, for example a substrate or inhibitor of a target enzyme, is chemically modified such that it can be covalently linked to an oligonucleotide of known sequence (the "guide oligonucleotide" of FIG. 10). The guide oligonucleotide chemically linked to the "anchor" molecule that binds to the target also binds to the target molecule. The sequence complement of guide oligonucleotide is incorporated near the randomized region of the test nucleic acid mixture. SELEX is then performed to select for those sequences that bind most strongly to the target molecule/ anchor complex. The iterative walking procedure can then be employed to select or produce longer and longer nucleic acid molecules with enhanced strength of binding or specifity of binding to the target. The use of the "anchor" procedure is expected to allow more rapid isolation of nucleic acid ligands that bind at or near a desired site within a target molecule. In particular, it is expected that the "anchor" method in combination with iterative "walking" procedures will result in nucleic acids which are highly specific inhibitors of protein function (FIG. 11).

In certain embodiments of the performance of SELEX it is desireable to perform plus/minus screening in conjunction with the selection process to assure that the selection process is not being skewed by some factor unrelated to the affinity of the nucleic acid sequences to the target. For example, when selection is performed by protein binding nitrocellulose, it has been seen that certain nucleic acid sequences are preferentially retained by nitrocellulose and can be selected during the SELEX process. These sequences can be removed from the candidate mixture by incorporating additional steps wherein the preceding SELEX mixture is passed through nitrocellulose to selectively remove those sequences selected solely for that property. Such screening and selection may be performed whenever the target contains impurities or the selection process introduces biases unrelated to affinity to the target.

SELEX has been demonstrated by application to the isolation of RNA molecules which bind to and inhibit the function of bacteriophage T4 DNA polymerase, also termed gp43. The novel RNA ligand of T4 DNA polymerase is useful as a specific assay reagent for T4 DNA polymerase. The synthesis of T4 DNA polymerase is autogenously regulated. In the absence of functional protein, amber fragments and mutant proteins are overexpressed when compared to the rate of synthesis of wild-type protein in replication-deficient infections (Russel (1973) J. Mol. Biol. 79:83–94). In vitro translation of an N-terminal fragment of gp43 is specifically repressed by the addition of purified gp43, and gp43 protects a discrete portion of the mRNA near its ribosome binding site from nuclease attack (Andrake et al. (1988) Proc. Natl. Acad. Sci. USA 85:7942–7946). The size and sequence of the RNA translational operator to which gp43 binds and the strength of that binding have been established. The minimal size of the gp43 operator is a sequence of about 36 nucleotides, as illustrated in FIG. 1, which is predicted to have a hairpin loop structure as indicated therein. The minimal size of the operator was determined by analysis of binding of end-labeled hydrolysis fragments of the operator to gp43. Analysis of binding of operator mutants in the hairpin and loop sequence indicate that gp43 binding to the operator is sensitive to primary base changes in the helix. Binding to the polymerase was even more reduced by changes-which significantly reduce hairpin stability. Operator binding was found to be very sensitive to loop sequence. It was found that replication and operator binding in gp43 are mutually exclusive activities. The addition of micromolar amounts of purified RNAs containing intact operator was found to strongly inhibit in vitro replication by gp43.

The wild-type gp43 operator, FIG. 1, was employed as the basis for the design of an initial mixture of RNA molecules containing a randomized sequence region to assess the ability of the selection/amplification process to isolate nucleic acid molecules that bind to a protein. The RNA test mixture was prepared by in vitro transcription from a 110 base single-stranded DNA template. The template was constructed as illustrated in FIG. 1 to encode most of the wild-type operator sequence, except for the loop sequence. The eight base loop sequence was replaced by a randomized sequence region which was synthesized to be fully random at each base. The template also contained sequences necessary for efficient amplification: a sequence at its 3' end complementarily to a primer for reverse transcription and amplification in polymerase chain reactions and a sequence in its 5' end required for T7 RNA polymerase transcriptional initiation and sufficient sequence complementary to the cDNA of the in vitro transcript. The DNA template is this a mixture of all loop sequence variants, theoretically containing 65,536 individual species.

The dissociation constant for the wild-type loop RNA was found to be about $5\times10^{-9}$M. The dissociation constant for the population of loop sequence variants was measured to be about $2.5\times10^{-7}$. Randomization of the loop sequence lowered binding affinity 50-fold.

In vitro transcripts containing the loop sequence variants were mixed with purified gp43 and incubated. The mixture was filtered through a nitrocellulose filter. Protein-RNA complexes are retained on the filter and unbound RNA is not. Selected RNA was then eluted from the filters as described in Example 1. Selected RNAs were extended with AMV reverse transcriptase in the presence of 3' primer as described in Gauss et al. (1987) supra. The resulting cDNA was amplified with Tag DNA polymerase in the presence of the 5' primer for 30 cycles as described in Innis et al. (1986) supra. The selected amplified DNA served as a template for in vitro transcription to produce selected amplified RNA transcripts which were then subject to another round of binding selection/amplification. The RNA/protein ratio in the binding selection mixture was held constant throughout the cycles of selection. The iterative selection/amplification was performed using several different RNA/protein molar ratios. In all experiments RNA was in excess: experiment A employed an RNA/gp43 of 10/1 (moles/moles); experiment B employed an RNA/gp43 of 1000/1; and experiment C employed an RNA/gp43 of 100/1.

Figure 3:
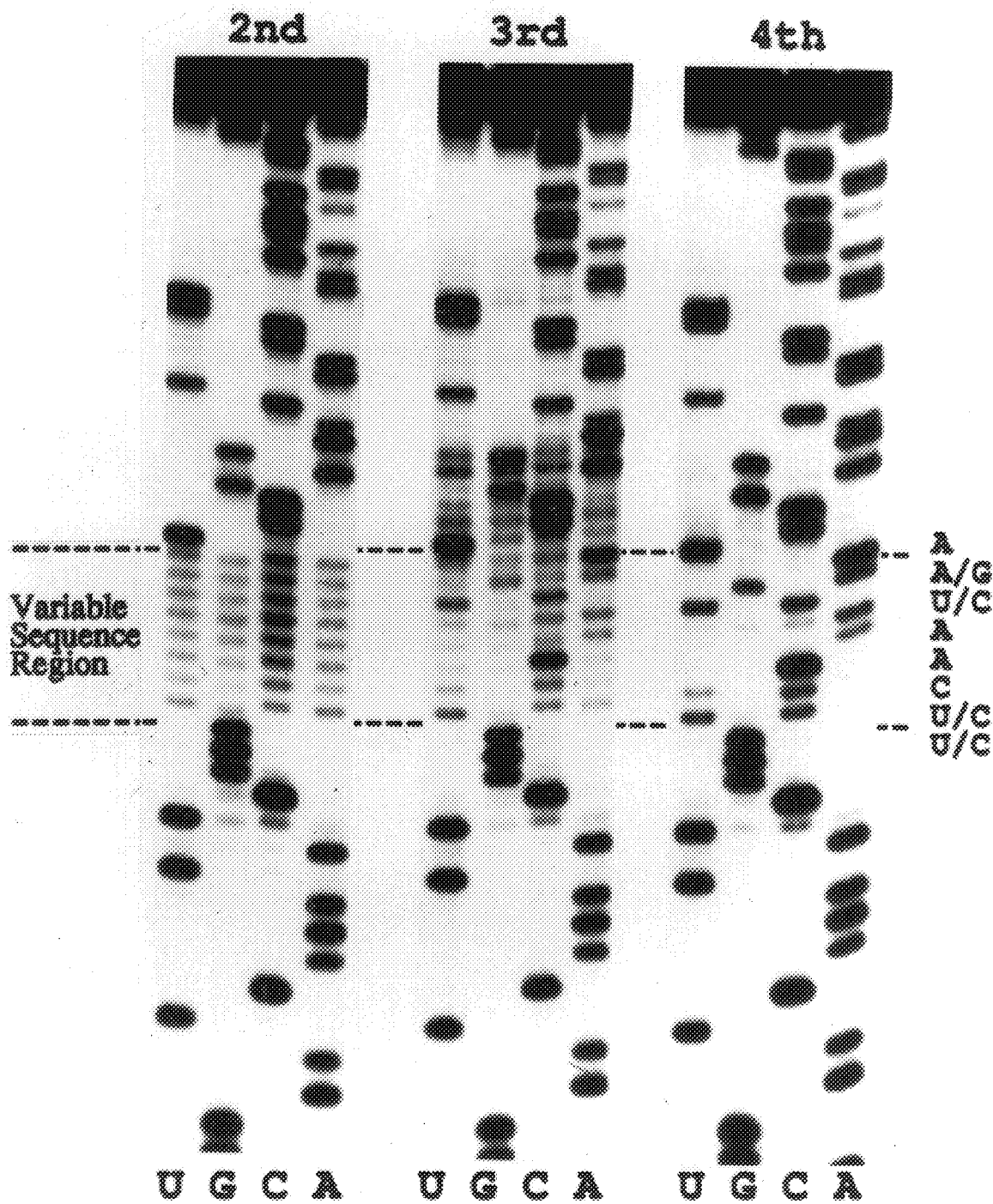
FIG. 3 is a composite of autoradiographs of electrophoresed batch sequencing reactions of the in vitro transcripts derived from SELEX for binding of RNA loop variants to gp43. The figure indicates the change in loop sequence components as a function of number of selection cycles (for 2, 3 and 4 cycles) for selection conditions of experiment B in which the concentration of gp43 was $3\times10^{-8}$M and the concentration of RNA was about $3\times10^{-5}$M in all selection cycles. Sequencing was performed as described in Gauss et al. (1987) Mol. Gen. Genet. 206:24–34.

The progress of the selection process was monitored by filter binding assays of labelled transcripts of amplified cDNA at the completion of each cycle of the procedure. Batch sequencing of the RNA products from each round for experiment B was also done to monitor the progress of the selection. Autoradiograms of sequencing gels of RNA products after 2, 3 and 4 rounds of selection/amplification are shown in FIG. 3. It is clear that there was no apparent loop sequence bias introduced until after the third selection. After the fourth round of selection, an apparent consensus sequence for the eight base loop sequence is discernable as: A(a/g)(u/c)AAC(u/c)(u/c). Batch sequencing of selected RNA after the fourth round of selection for experiments A, B and C is compared in FIG. 4. All three independent SELEX procedures using different RNA/protein ratios gave similar apparent consensus sequences. There was, however, some apparent bias for wild-type loop sequence (AAUAACUC) in the selected RNA from experiments A and C.

Figure 6:
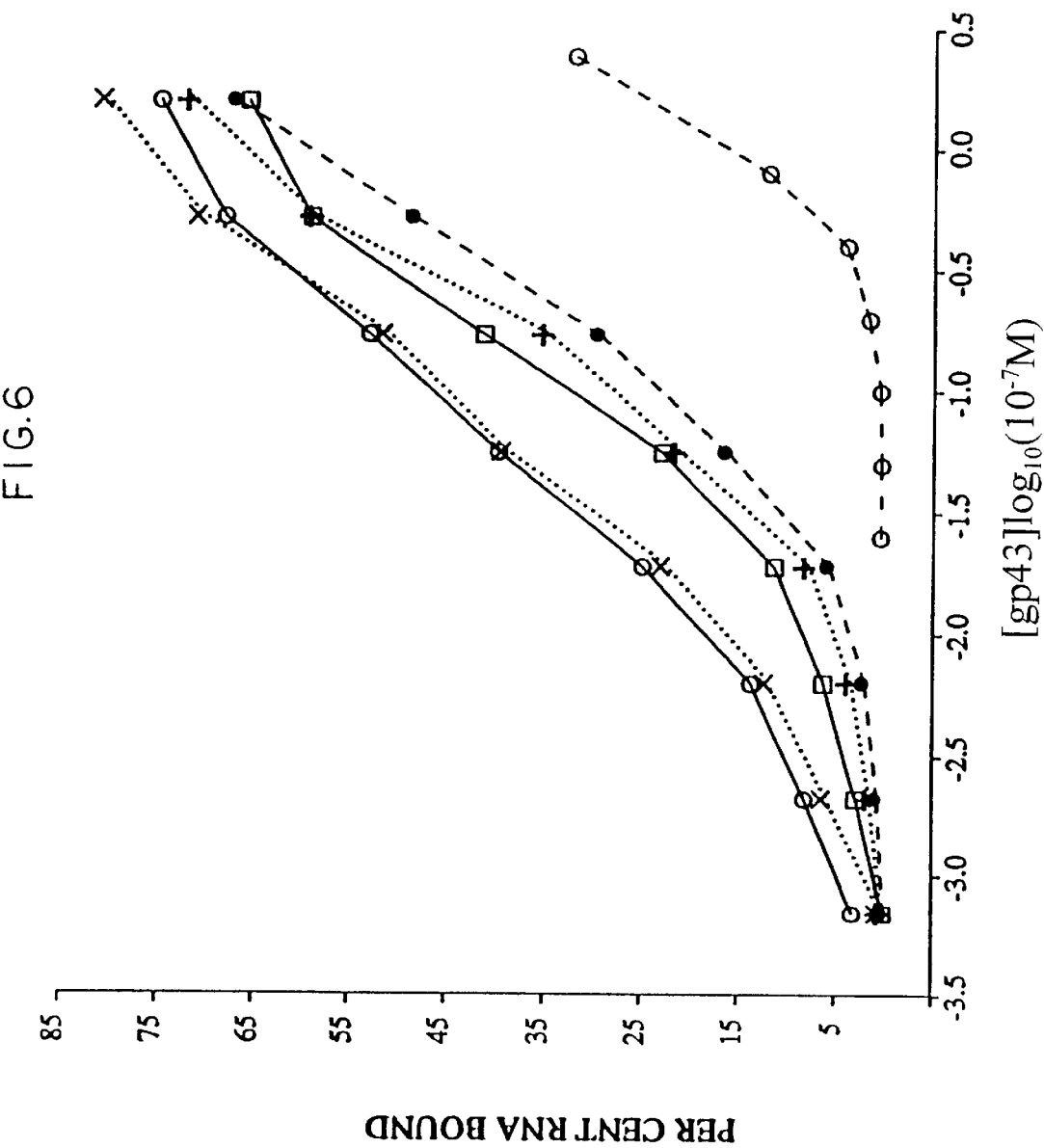
FIG. 6 is a graph of percent RNA bound to gp43 as a function of gp43 concentration for different selected RNA loop sequence variants and for RNA with a randomized loop sequence. Binding of the wild-type loop sequence AAUAACUC is indicated as open-circles, solid line; major variant loop sequence AGCAACCU as "x," dotted line; minor variant loop sequence AAUAACUU as open squares, solid line; minor variant loop sequence AAUGACUC as solid circles, dotted line; minor variant loop sequence AGCGACCU as crosses, dotted line; and binding of the randomized mixture (NNNNNNNN) of loop sequences as open circles, dotted line.
Figure 7:
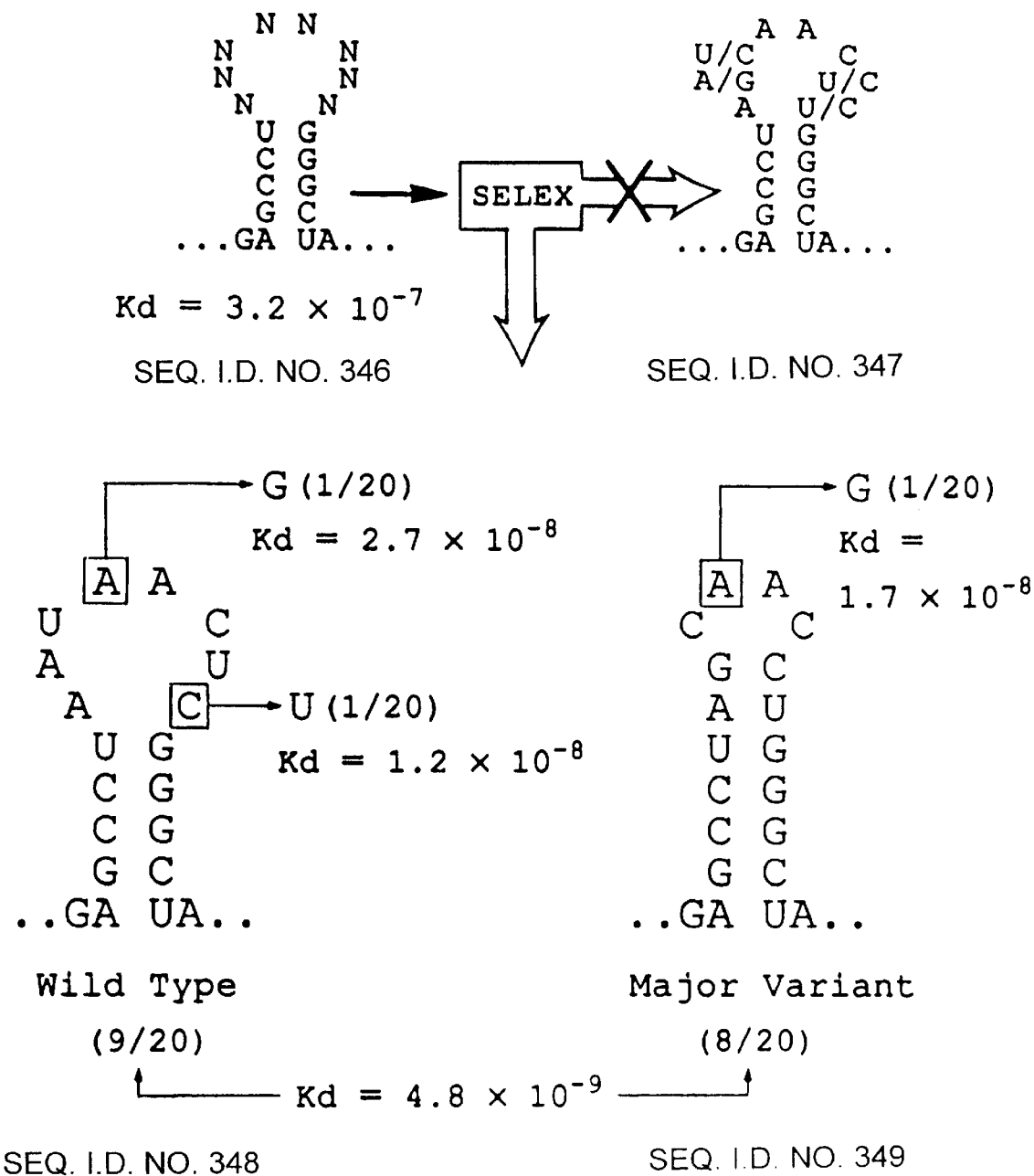
FIG. 7 is a pictorial summary of results achieved after four rounds of SELEX to select a novel gp43 binding RNA from a candidate population randomized in the eight base-pair loop. SELEX did not yield the "apparent" consensus expected from the batch sequences shown in FIG. 4, but instead yielded wild type and a single major variant in about equal proportions and three single mutants. The frequencies of each species out of twenty cloned isolates are shown together with the approximate affinity constants (Kd) for each, as derived from filter binding assays shown in FIG. 6.

In order to determine what allowable sequence combinations were actually present in the selected RNAs, individual DNAs were cloned from selected RNAs after the fourth round of selection in experiment B. The batch sequence result from experiment B appeared to indicate an even distribution of the two allowable nucleotides which composed each of the four variable positions of the loop sequence. Individuals were cloned into pUC18 as described by Sambrook, J. et al. (1989) *Molecular Cloning: A Laboratory Manual*, (Cold Spring Harbor, N.Y.), Sections 1.13; 1.85–1.86. Twenty individual clones that were identified by colony filter hybridization to the 3' primer were sequenced. None of the sequenced clones were mutant at any place in the operator sequence outside of the loop sequence. Only five variant sequences were observed as shown in FIG. 7, and surprisingly only two sequence variants were the major components of the selected mixture. The frequencies of each sequence in the 20 individual isolates sequenced are also given in FIG. 7. The wild-type sequence AAUAACUC and the loop AGCAACCU were present in approximately equal amount in the selected RNA of experiment B. The other selected variants were 1 base mutants of the two major variants. The strength of binding of the sequence variants was compared in filter binding assays using labelled in vitro transcripts derived from each of the purified clonal isolates. As shown in FIG. 6, a rough correlation between binding affinity of an RNA for gp43 and the abundance of the selected sequence was observed. The two major loop sequence variants showed approximately equal binding affinities for gp43.

The loop sequence variant RNAs isolated by the selection/amplification process, shown in FIG. 7, can all act as inhibitors of gp43 polymerase activity as has been demonstrated for the wild-type operator sequence.

An example of the use of SELEX has been provided by selection of a novel RNA ligand of bacteriophage T4 DNA polymerase (gp43) (Andrake et al. (1988) Proc. Natl. Acad. Sci. USA 85:7942–7946).

The present invention includes specific ligand solutions, derived via the SELEX process, that are shown to have an increased affinity to HIV-1 reverse transcriptase, R17 coat protein, HIV-l rev protein, HSV DNA polymerase, *E. coli* ribosomal protein S1, tPA and NGF. These ligand solutions can be utilized by one of skill in the art to synthesize nucleic acid antibodies to the various targets.

The following examples describe the successful application of SELEX to a wide variety of targets. The targets may generally be divided into two categories—those that are nucleic acid binding proteins and those proteins not known to interact with nucleic acids. In each case a ligand solution is obtained. In some cases it is possible to represent the ligand solution as a nucleic acid motif such as a hairpin loop, an asymmetric bulge or a pseudoknot. In other examples the ligand solution is presented as a primary sequence. In such cases it is not meant to be implied that the ligand solution does not contain a definitive tertiary structure.

In addition to T4 DNA polymerase, targets on which SELEX has been successfully performed include bacteriophage R17 coat protein, HIV reverse transcriptase (HIV-RT), HIV-1 rev protein, HSV DNA polymerase plus or minus cofactor, *E. coli* ribosomal protein S1, tPA and NGF. The following experiments also describe a protocol for testing the bulk binding affinity of a randomized nucleic acid candidate mixture to a variety of proteins. Example 7 also describes the immobilization of bradykinin and the results of bulk randomized nucleic acid binding studies on bradykinin.

The examples and illustrations herein are not to be taken as limiting in any way. The fundamental insight underlying the present invention is that nucleic acids as chemical compounds can form a virtually limitless variety of sizes, shapes and configurations and are capable of an enormous repertoire of binding and catalytic functions, of which those known to exist in biological systems are merely a glimpse.

EXAMPLES

The following materials and methods were used throughout.

The transcription vector pT7-2 is commercially available (U.S. Biochemical Company, Cleveland, Ohio). Plasmid pUC18 is described by Norrander et al. (1983) Gene 24:15–27 and is also commercially available from New England Biolabs. All manipulations of DNA to create new recombinant plasmids were as described in Maniatis et al. (1982) *Molecular Cloning: A Laboratory Manual*, Cold Spring Harbor Laboratory, Cold Spring Harbor, N.Y., except as otherwise noted. DNA olignucleotides were synthesized and purified as described in Gauss et al. (1987) Mol. Gen. Genet. 206:24–34.

In vitro transcriptions with T7 RNA polymerase and RNA gel-purification were performed as described in Milligan et al. (1987) Nucl. Acids Res. 15:8783–8798, except that in labeling reactions the concentrations of ATP, CTP, and GTP were 0.5 mM each, and the UTP concentration was 0.05 mM. The UTP was labeled at the alpha position with $^{32}P$ at a specific activity of approximately 20 Ci/mmol. Crude mRNA preparations from T4 infections, labeling of oligos, and primer extension with AMV reverse transcriptase were all according to Gauss et al. (1987) supra.

Dilutions of labeled, gel-purified RNA and purified gp43 were made in 200 mM potassium acetate, 50 mM Tris-HCl pH 7.7 at 4° C. In nitrocellulose filter binding assays, purified gp43 was serially diluted and 30 μl aliquots of each dilution of protein were added to 30 μl aliquots of diluted, labeled, gel-purified RNA. The RNA dilution (50 μl) was spotted on a fresh nitrocellulose filter, dried and counted to determine input counts per tube. The concentration of protein in the reactions ranged from $10^{-10}M$ to $10^{-8}M$ and the concentration of the RNAs in each experiment was approximately $10^{-12}M$. After incubation at 4° C. for 30 minutes, each tube was placed at 37° C. for 3 minutes and 50 μl of each sample filtered through pre-wet nitrocellulose filters (Millipore #HAWP 025 00) and washed with 3 ml of 200 mM Tris-HCl pH 7.7. The filters were dried and counted in Ecolume™ scintillation fluid (ICN Biomedicals, Inc.). Controls were done in the absence of gp43, from which the background (always less than about 5% of the input counts) was determined. From each set of measurements the background was subtracted, and the percent of total input counts remaining on the filters calculated. From each set of data points, a best-fit theoretical bimolecular binding curve was generated using a version of a published program (Caceci and Cacheris, 1984 supra) modified to construct a curve described by the equation, $$\rho = A[gp43]/(Kd+[gp43])$$

where ρ is the fraction of the total RNA that is bound to the filter, A is the percent of RNA at which binding saturates (approximately 60% for this protein-RNA interaction), [gp43] is the input gp43 concentration, and Kd is the dissociation constant for the bimolecular reaction. This equation is an algebraic rearrangement of equation [1–5] from Bisswanger (1979) *Theorie und Methoden der Enzvmkinetik*, Verlag Chemie, Weinheim, FRG, p. 9 with the simplifying assumption that the concentration of the protein far exceeds the concentration of RNA-protein complexes, an assumption which is valid in the experiments described.

Example 1

Selection of RNA Inhibitors of T4 DNA Polymerase

Figure 2:
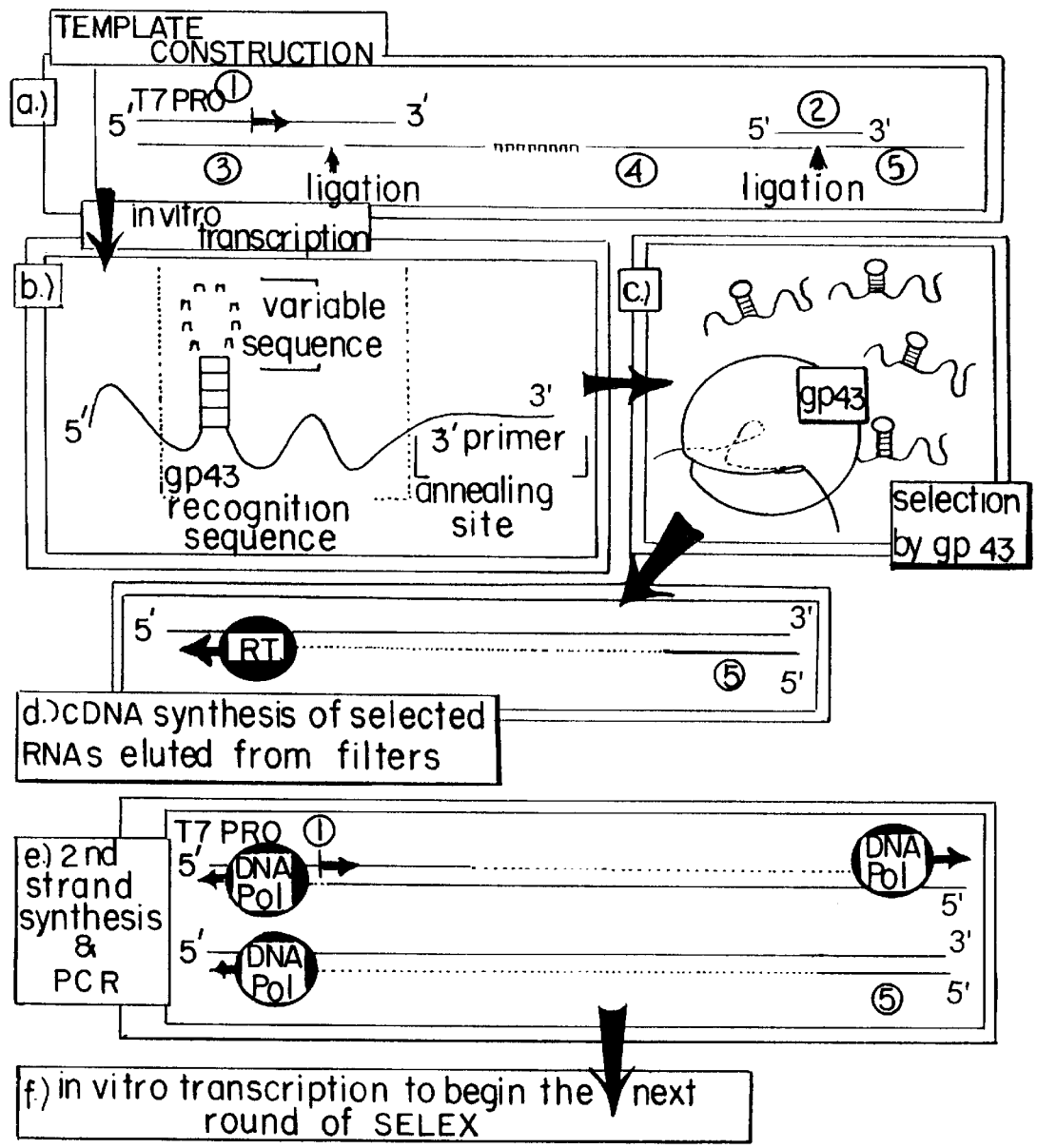
FIG. 2 is a schematic diagram of the SELEX process as exemplified for selecting loop sequence variants for RNAs that bind to T4 DNA polymerase (gp43). A DNA template for preparation of a test mixture of RNAs was prepared as indicated in step a by ligation of oligomers 3, 4 and 5, whose sequences are given in Table 1 infra. Proper ligation in step a was assured by hybridization with oligomers 1 and 2, which have complementary sequence (given in Table 1) that bridges oligomers 3 and 4 and 4 and 5, respectively. The resultant 110-base long template was gel-purified, annealed to oligo 1 and was used in vitro transcription reactions (Miligan et al. (1987) Nucl. Acids Res. 15:8783–8798) to produce an initial RNA mixture containing randomized sequences of the 8-base loop, step b. The resultant transcripts were gel-purified and subjected to selection on nitrocellulose filters for binding to gp43 (step c), as described in Example 1. Selected RNAs were amplified in a three step process: (d) cDNA copies of the selected RNAs were made by reverse transcriptase synthesis using oligo 5 (Table 1) as a primer; (e) cDNAs were amplified using Taq DNA polymerase chain extension of oligo 1 (Table 1), which carries essential T7 promoter sequences, and oligo 5 (Table 1) as described in Innis et al. (1988) Proc. Natl. Acad. Sci. USA 85:9436; and (f) double-stranded DNA products of amplification were transcribed in vitro. The resultant selected amplified RNAs were used in the next round of selection.

A 110 base single-stranded DNA template for in vitro transcription was created as shown in FIG. 2 by ligation of three synthetic oligonucleotides (Tables 1, 3, 4 and 5) in the presence of two capping oligonucleotides (Tables 1 and 2). One of the template-creating oligos was also used as the 3' primer in reverse transcription of the in vitro transcript and subsequent amplification in polymerase chain reactions (PCRs) (Innis et al. (1988) Proc. Natl. Acad. Sci. USA 85:9436–9440). One of the capping oligos (1) contains the information required for T7 RNA polymerase transcriptional initiation and sufficient sequence complementarily to the cDNA of the in vitro transcript to serve as the 5' primer in the PCR amplification steps. The DNA template encoded an RNA which contains the entire RNA recognition site for T4 DNA polymerase except that a completely random sequence was substituted in place of the sequence which would encode the wild-type loop sequence AAUAACUC. The random sequence was introduced by conventional chemical synthesis using a commercial DNA synthesizer (Applied Biosystems) except that all four dNTP's were present in equimolar amounts in the reaction mixture for each position indicated by N in the sequence of oligonucleotide number 4 (Table 1). The random sequence is flanked by primer annealing sequence information for the 5' and 3' oligos used in PCR. The DNA template is thus a mixture of all loop sequence variants, theoretically containing 65,536 individual species. The dissociation constant for the wild-type loop variant RNA sequence is about $5 \times 10^{-9}$ M and for the population of sequences was measured to be about $2.5 \times 10^{-7}M$, a 50-fold lower binding affinity.

TABLE 1

| | | |
|---|---|---|
| 1) | 5'-TAATACGACTCACTATAGGGAGCCAACACCACAATTCCAATCAAG-3' | (SEQ ID NO: 4) |
| 2) | 5'-GGGCTATAAACTAAGGAATATCTATGAAAG-3' | (SEQ ID NO: 5) |
| 3) | 5'-GAATTGTGGTGTTGGCTCCCTATAGTGAGTCGTATTA-3' | (SEQ ID NO: 6) |
| 4) | 5'-ATATTCCTTAGTTTATAGCCCNNNNNNNNAGGCTCTTGATTG-3' and | (SEQ ID NO: 7) |
| 5) | 5'-GTTTCAATAGAGATATAAAATTCTTTCATAG-3' | (SEQ ID NO: 8) |

In vitro transcripts containing the loop sequence variants were mixed with purified gp43 at three different RNA-protein ratios throughout the multiple rounds of selection. (For A and B the concentration of gp43 was $3 \times 10^{-8}M$, "low protein," and for C the concentration of gp43 was $3 \times 10^{-7}M$, "high protein." For A the concentration of RNA was about $3 \times 10^{-7}$, "low RNA," and for B and C the concentration of RNA was about 3×10⁻⁵M, "high RNA.") One round consisted of the following steps:

1) Selection. The RNA and protein were mixed in the desired ratios described above, incubated at 37° C., washed through a nitrocellulose filter, and RNA was eluted from the filters as described supra.

2) Amplification. The RNA eluted from filters was extended with AMV reverse transcriptase in the presence of 50 picomoles of 3' promer in a 50 μl reaction under conditions described in Gauss et al. (1987) supra. To the resulting cDNA synthesis 50 picomoles of 5' primer was added and in a reaction volume of 100 μl and was amplified with Taq DNA polymerase as described in Innis (1988) supra for 30 cycles.

Figure 4:
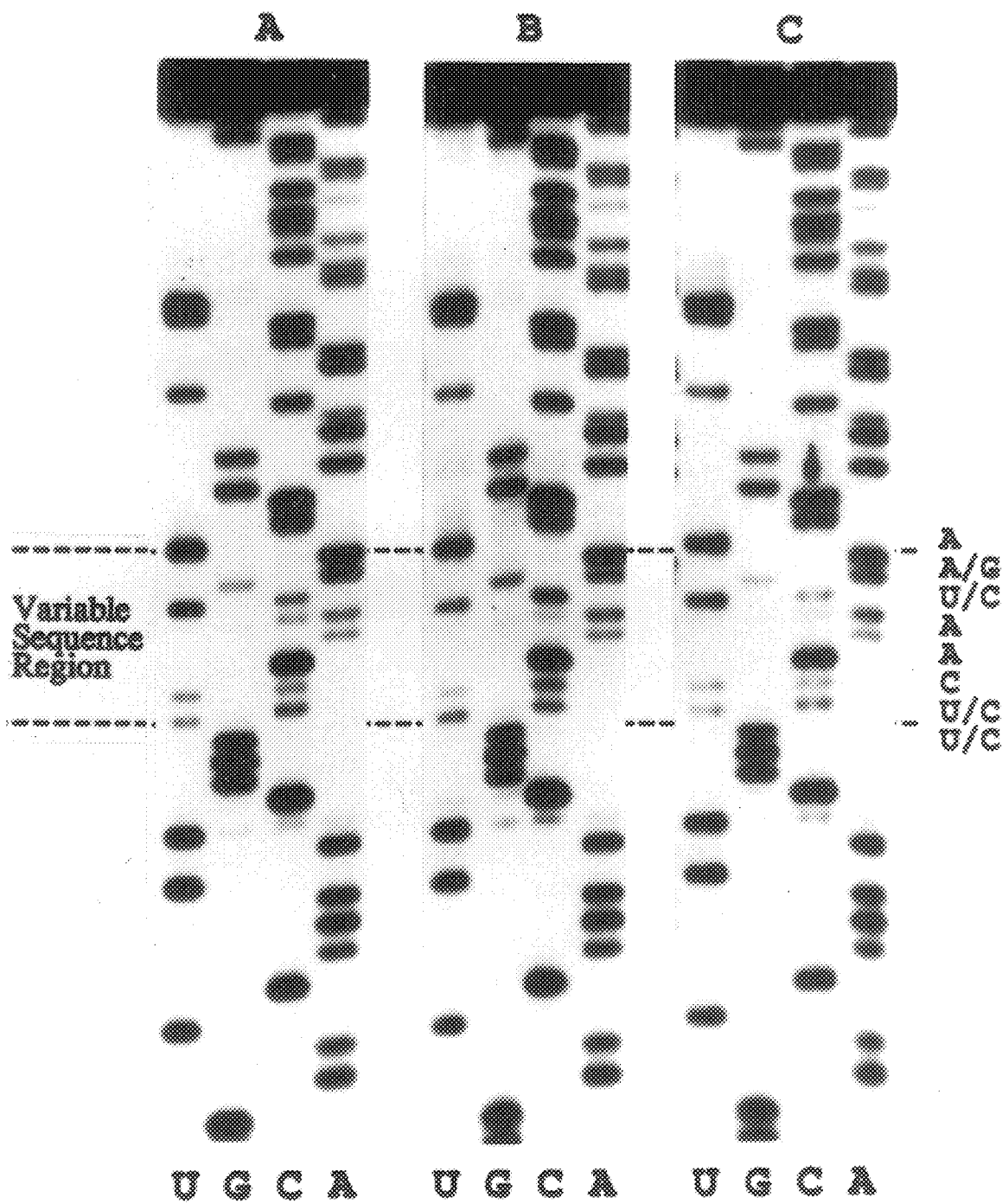
FIG. 4 is a composite of autoradiographs of batch RNA sequences of those RNAs selected from the fourth round of SELEX amplification for binding of RNA loop variants to gp43 employing different binding conditions. In experiment A gp43 concentration was $3\times10^{-8}$M and RNA concentration was about $3\times10^{-7}$M. In experiment B, gp43 was $3\times10^{-8}$M and RNA was about $3\times10^{-5}$M. In experiment C, gp43 was $3\times10^{-7}$M and RNA was about $3\times10^{-5}$M.
Figure 5:
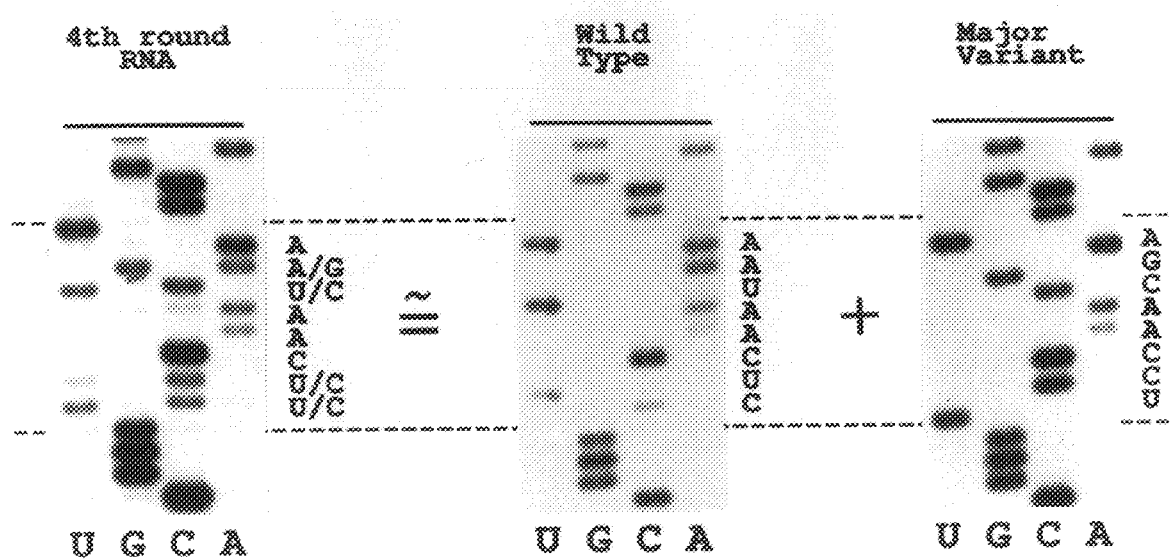
FIG. 5 is a composite of autoradiographs of three sequencing gels for loop variants selected for binding to gp43 under the selection conditions of experiment B (see Example 1). The left hand sequence gel is the batch sequencing of selected RNAs after the fourth round of selection/amplification. The middle and right hand sequence gels are double-stranded DNA sequencing gels of two clonal isolates derived form the batch RNAs. The batch of RNA selected is composed of two major variants, one of which was the wild-type sequence (middle sequence gel), and a novel sequence (right hand gel).

3) Transcription. In vitro transcription is performed on the selected amplified templates as described in Milligan et al. (1987) supra, after which DNaseI is added to remove the DNA template. The resultant selected RNA transcripts were then used in step 1 of the next round. Only one-twentieth of the products created at each step of the cycle were used in the subsequent cycles so that the history of the selection could be traced. The progress of the selection method was monitored by filter binding assays of labeled transcripts from each PCR reaction. After the fourth round of selection and amplification, the labeled selected RNA products produced binding to gp43 equivalent to that of wild-type control RNA. The RNA products from each round for one experiment (B) and from the fourth round for all three experiments were gel-purified and sequenced. In FIG. 3, we show the sequence of the purified in vitro transcripts derived from the second, third and fourth rounds of selection and amplification for experiment B. It is clear that there was no apparent loop sequence bias introduced until after the third selection. By this point in the selection, there was a detectable bias which was complete by the fourth round for the apparent consensus sequence A(a/g)(u/c)AAC(u/c)(u/c). Batch sequencing of the RNA transcribed after the fourth selection and amplification for trials A, B, and C is shown in FIG. 4. All three independent runs with different protein/RNA ratios gave similar results. There is some apparent bias for wild-type sequence at each of the four "variable" positions in experiments A and C.

In order to find out what allowable combinations actually existed, we used two "cloning" oligonucleotides which contained restriction site information, to amplify sequences from RNA from the fourth round of experiment B from which individuals were cloned into pUC18 as described (Sambrook et al. (1989) supra; Innis et al. (1988) supra). The selected batches of trial B were chosen for further examination because there appeared to be an even distribution of the two allowable nucleotides which composed each of the four "variable" positions. Twenty individual clones that were identified by colony filter hybridization to the 3' primer were sequenced. None of these individuals were mutant at any place in the operator sequence outside of the loop sequence positions that were deliberately varied. The sequence distributions are summed up in FIG. 7. Surprisingly, the selected RNA mixture was actually composed of two major loop sequences. One was the wild-type sequence, AAUAACUC of which 9 out of 20 were isolated. The other, AGCAACCU, was mutant at four positions and existed in 8 of the 20 clones (see FIG. 7). The other three loop sequences detected were single mutations of these two major sequences. Filter binding experiments with labeled in vitro transcripts derived from each of these clonal isolates indicated that there was a rough correlation between binding affinity of an RNA for gp43 and selected abundance (see FIG. 7)

Example 2

Isolation of a specific RNA ligand for HIV reverse transcriptase

The reverse transcriptase activity of HIV-1 is composed of a heterodimer of two subunits (p51 and p66) that have common amino termini. The extra carboxyterminal region of the larger peptide comprises the RNaseH domain of reverse transcriptase; the structure of that domain has recently been determined at high resolution.

It has been previously shown that this HIV-1 reverse transcriptase directly and specifically interacts with its cognate primer tRNA$^{Lys3}$ to which it was experimentally cross-linked at the anti-codon loop and stem. It was also found that only the heterodimer exhibited this specific RNA recognition; neither homodimeric species of reverse transcriptase bound with specificity to this tRNA.

Two template populations (with approximately 10$^{14}$ different sequences each) were created for use in SELEX by ligation. One template population was randomized over 32 nucleotide positions, using fixed sequences at the ends of the randomized region to afford cDNA synthesis and PCR amplification. The second template population had, as additional fixed sequence at the 5' end of the RNA, the anticodon loop and stem of tRNA$^{Lys3}$. (All oligos used in this work are shown in Table 2). There was no difference in the affinity of the two randomized populations for HIV-1 reverse transcriptase [RT] (and, as is shown, the RNAs which were selected did not utilize either 5' region in specific binding). Nine rounds of SELEX with each population were performed using the heterodimer HIV-RT as the target protein.

The mechanism by which the randomized DNA was prepared utilizing ligations and bridging oligonucleotides was described previously. Such methodology can diminish the total number of different sequences in the starting population from the theoretical limit imposed by DNA synthesis at the 1 micromole scale.

In these ligation reactions about 1 nanomole of each oligonucleotide was used. The ligated product was gel-purified with an approximate yield of 50%. This purified template was transcribed with T7 RNA polymerase as described above. It was found that HIV RT could saturably bind this random population with a half-maximal binding occuring at about 7×10⁻⁷ M as determined by nitrocellulose assays. All RNA-protein binding reactions were done in a binding buffer of 200 mM KOAc, 50 mM Tris-HCl pH 7.7, 10 mM dithiothreitol. RNA and protein dilutions were mixed and stored on ice for 30 minutes then transferred to 37° C. for 5 minutes. (In binding assays the reaction volume is 60 μl of which 50 ul is assayed; in SELEX rounds the reaction volume is 100 ul). Each reaction is suctioned through a prewet (with binding buffer) nitrocellulose filter and rinsed with 3 mls of binding buffer after which it is dried and counted for assays or subjected to elution as part of the SELEX protocol. Nine rounds were performed. The RNA concentration for all nine rounds was approximately 3×10⁻⁵M. HIV-RT was 2×10⁻⁸M in the first selection and 1×10⁻⁸M in selections 2–9.

The experiment using RNA containing the tRNA$^{Lys3}$ anticodon loop and stem was completed first. Nitrocellulose filter binding assays performed at the ninth round revealed that the RNA population had increased about 100-fold in affinity to HIV-1 RT when compared to the starting canidate mixture, but that the background binding to nitrocellulose filters in the absence of protein had increased from about 2% of input RNA to 15%. Individual sequences were cloned from this population (after filtration through nitrocellulose filters to delete some of the high background of potential sequences selected for retention by filters alone) and are listed in Table 3. Nitrocellulose filter binding assays of selected sequences' affinity for HIV RT are shown in FIG. 14. Some of the sequences were selected as ligands for HIV-RT, exemplified by the binding curves of ligands 1.1 and 1.3a, and show some sequence homology as illustrated by Tables 4 and 5. Some of the ligand sequences exhibit significant retention on nitrocellulose filters in the absence of protein, exemplified by ligand 1.4 (FIG. 14), and seem to be characterized by a long helix with a loop of purine repeat elements (as shown in Table 4). In spite of our minimal, late efforts to delete them in this experiment prior to cloning, these sequences represented a significant part of those collected from this experiment.

As a consequence, experiment 2 (which has a different 5' fixed sequence) was pre-filtered through nitrocellulose before the first, third, sixth and ninth rounds of selection. The sequences collected from this experiment are shown in Table 6. There are again many sequences with homology to those of high affinity from experiment 1 as shown in Tables 4 and 5. There are many fewer, if any, sequences that fit the motif of sequences retained by nitrocellulose filters alone. Nitrocellulose binding assays of selected ligand sequences from this experiment compared to that of ligand 1.1 are shown in FIG. 15.

High affinity ligand RNAs with the most common sequence (1.1) and a similar sequence (1–3a) were further analyzed to determine the boundaries of the information required for high affinity binding to RIV-1 RT. The results of these experiments are shown in FIG. 16. These experiments establish that the motif common to these sequences, UUC-CGNNNNNNNNCGGGAAA (SEQ ID NO:9), are similarly positioned within the recognition domain. The sequences UUCCG and CGGGA of this motif may base-pair to form an RNA helix with an eight base loop. In order to discover what besides these fixed sequences may contribute to high affinity binding to HIV-1 RT, a canidate mixture template was created that contained random incorporation at the nucleotide positions that differ from these two sequences as shown in Table 7. After eight rounds of SELEX, individual sequences were cloned and sequenced. The 46 sequences are shown in Table 7. Inspection of these sequences reveals extensive base-pairing between the central 8n variable region and the downstream 4n variable region and flanking sequences; base-pairing which in combination with that discussed above would indicate an RNA pseudoknot. That no specific sequences predominate in this evolved population suggests that there is no selection at the primary sequence level and that selection occurs purely on the basis of secondary structure, that is, there are many sequence combinations that give similar affinities for HIV-1 RT, and none have competitive advantage. Analysis of the first and second SELEX experiments reveals that the individual sequences which comprise those populations that have homology to the UUCCG . . . CGGGANAA motif also show a strong potential for this pseudoknot base-pairing.

FIG. 31 shows a schematic diagram of what is referred to herein as a pseudoknot. A pseudoknot is comprised of two helical sections and three loop sections. Not all pseudoknots contain all three loops. For the purposes of interpreting the data obtained, the various sections of the pseudoknot have been labeled as shown in FIG. 31. For example, in Table 5 several of the sequences obtained in experiments one and two are listed according to the pseudoknot configuration assumed by the various sequences.

The results of experiments one and two, as defined in Table 5, led to experiment three wherein sequences in S1(a), S1(b) and L3 were fixed. Again, the SELEX derived nucleic acids were configured almost exclusively in pseudoknots. Examination of the results in each of the experiments reveals that the nucleic acid solution to HIV-RT contains a relatively large number of members, the most basic common denominator being that they are all configured as pseudoknots. Other generalizations defining the nucleic acid solution for HIV-RT are as follows:

1) S1(a) often comprises the sequence 5'-UUCCG-3' and S1(b) often comprises the sequence 5'-CGGGA-3'. However, base pair flips are allowed, and the stem may be shortened.

2) L1 may be short or long, but often comprises two nucleotides in the best binding nucleic acids. The 5' nucleotide in L1 often is either a U or an A.

3) S2 is usually comprised of 5 or 6 base pairs, and appears to be sequence independent. This stem may contain non-Watson/Crick pairs.

4) L2 may be comprised of no nucleotides, but when it exists, the nucleotides are preferably A's.

5) L3 is generally 3 or more nucleotides, enriched in A.

6) In most sequences obtained by SELEX, the total number of nucleotides in L1, 52(a) and L2 equals 8.

A primary purpose of this experiment was to find ligand solutions to HIV-1 RT. The ability of the evolved ligand clone 1.1. was compared to the ability of the starting population for experiment 1 to inhibit reverse transcriptase activity, and is shown in FIG. 17. Even at equal concentrations of inhibitor RNA to RT, the reverse transcriptase is significantly inhibited by ligand 1.1. In contrast, only at 10 mM (or 200-fold excess) starting population RNA is there any significant inhibition of the HIV-1 RT. Thus, the high affinity ligand to HIV-1 RT either blocks or directly interacts with the catalytic site of the enzyme.

In order to test the specifity of this inhibition, various concentrations of ligand 1.1 were assayed for inhibition of KMLV, AMV and HIV-1 reverse transcriptase the results of that experiment which are shown in FIG. 18 show that the inhibition of ligand 1.1 is specific to HIV-1 reverse transcriptase.

Example 3

Isolation of specific RNA ligand for bacteriophaae R17 coat protein.

SELEX was performed on the bacteriophage R17 coat protein. The protein was purified as described by Carey et al., Biochemistry, 22, 2601 (1983). The binding buffer was 100 mM potassium acetate plus 10 mM dithiothreitol plus 50 mM Tris-acetate pH 7.5. Protein and RNA were incubated together for three minutes at 37° C. and then filtered on nitrocellulose filters to separate protein-bound RNA from free RNA. The filters were washed with 50 mM Tris-acetate pH 7.5. Protein was at $1.2 \times 10^{-7}$ for the first four rounds of SELEX and at $4 \times 10^{-8}$ for rounds five through 11.

The starting RNA was transcribed from DNA as described previously. The DNA sequence includes a bacteriophage T7 RNA polymerase promoter sequence that allows RNA to be synthesized according to standard techniques. cDNA synthesis during the amplification portion of the SELEX cycle is primed by a DNA of the sequence: cDNA primer (PCR primer 1) (SEQ ID NO:10): 5' GTTTCAATA-GAGATATAAAATTCTTCATAG 3'

The DNA primers used to amplify the cDNA was, thus, the sequence including the T7 promoter, 32 randomized positions, an AT dinucleotide, and the fixed sequence complementary to PCR primer 1. The RNA that is used to begin the first cycle of SELEX thus has the sequence (SEQ ID NO:11): pppGGGAGCCAACACCACAAUUCCAAUCAAG-32W-AUCUAUGAAAGAAUUUUAUCUCUAUUGAAC A set of clones from after the 11th round of SELEX was obtained and sequenced. Within the 38 different sequences obtained in the 47 clones were three found more than once: one sequence was found six times, one sequence four times, and another two times. The remaining 35 sequences were found once each. Two sequences were not similar to the others with respect to primary sequences or likely secondary structures, and were not analyzed further. Thirty-six sequences had in common the sequence ANCA situated as a tetranucleotide loop of a bulged hairpin; the bulged nucleotide was an adenine in all 36 cases. The sequences of the entire set are given in Table 8, aligned by the four nucleotides of the hairpin loop. The two nucleotides 3' to the randomized portion of the starting RNA (an AU) are free to change or be deleted since the cDNA primer does not include the complementary two nucleotides; many clones have changed one or both of those nucleotides.

The winning RNA motif, shown in FIG. 19, bears a direct relationship to the coat binding site identified earlier through site-directed mutagenesis and binding studies. See, Uhlenbeck et al. supra (1983); Ramaniuk et al. supra (1987). However, some of the sequences are more conserved in this set than might have been expected. The loop sequence AUCA predominates, while earlier binding data might have suggested that ANCA sequences are all equivalent. The natural binding site on the R17 genome includes the sequence and structure shown below:

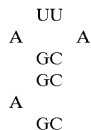

The natural structure includes the sequence GCAG, which serves to facilitate ribosome binding and initiation of translation of the R17 replicate coding region. During SELEX that requirement is not present, and the winning sequences contain around the loop and bulge C:G base pairs more often than G:C base pairs. SELEX, therfore, relaxes the constraints of biology and evolutionary history, leading to ligands with higher affinities than the natural ligand. Similarly, the loop cytidine found in each of the 36 sequences is a uridine in the natural site, and it is known that C provides higher affinity than U. During evolution natural sites must have an appropriate affinity rather than the highest affinity, since the tightest binding may lead to disadvantages for the organism.

Example 4

Isolation of a nucleic acid ligand for a serine protease

Serine proteases are protein enzymes that cleave peptide bonds within proteins. The serine proteases are members of a gene family in mammals, and are important enzymes in the life of mammals. Serine proteases are not known to bind to nucleic acids. Examples of serine proteases are tissue plasminogen activator, trypsin, elastase, chymotrypsin, thrombin, and plasmin. Many disease states can be treated with nucleic acid ligands that bind to serine proteases, for example, disorders of blood clotting and thrombus formation. Proteases other than serine proteases are also important in mammalian biology, and these too would be targets for nucleic acid ligands with appropriate affinities obtained according to the invention herein taught.

Human tissue plasminogen activator (htPA), available from commercial sources, was chosen as a serine protease to place through the SELEX method of this invention. The RNA candidate mixture used was identical to that described in Example 11 below in the HSV DNA polymerase experiment.

Binding during SELEX was in 50 mM NaCl plus 50 mM Tris-acetate pH 7.5 for 3 minutes at 37 degrees. SELEX was carried out for ten rounds. The 30N candidate mixture bound to tPA with an affinity (kd) of 7×10(−8) M in 150 mM NaAc plus 50 mM Tris-acetate pH 7.5; the affinity of the RNA present after nine rounds of SELEX was about threefold tighter. Nine clones were isolated, sequenced, and some of these were tested for binding to tPA as pure RNAs. The sequences of the nine clones obtained at low salt were as follows:

Name # Sequence of random region
A1  3  ACGAAACAAAUAAGGAGGAGGAGGGAUUGU
       (SEQ ID NO:12)
A2  1  AGGAGGAGGAGGGAGAGGGCAAAUGAGAUU
       (SEQ ID NO:13)
A3  1  AGGAGGAGGAGGUAGAGCAUGUAUUAAGAG
       (SEQ ID NO:14)
B   1  UAAGCAAGAAUCUACGAUAAAUACGUGAAC
       (SEQ ID NO:15)
C   1  AGUGAAAGACGACAAACGAAAAACGACCACA
       (SEQ ID NO:16)
D   1  CCGAGCAUGAGCCUAGUAAGUGGUGGAUA
       (SEQ ID NO:17)
E   1  UAAUAAGAGAUACGACAGAAUACGACAUAA
       (SEQ ID NO:18)

All tested sequences bound at least somewhat better than the starting 30N candidate mixture. However, the A series bound to nitocellulose better in the absence of tPA than did the candidate mixture, as though the shared sequence motif caused retention on the nitrocellulose matrix by itself. That motif is underlined in the sequences shown above. In other SELEX experiments AGG repeats have been isolated when trying to identify a ligand solution to HIV-1 reverse transcriptase, the human growth hormone receptor extracellular domain, and even the R17 coat protein in a first walking experiment. When tested, these sequences show modest or substantial binding to nitrocellulose filters without the target protein being present. It appears that the AGG repeats may be found in hairpin loops. Since SELEX is an iterative process in most embodiments, it is not surprising that such binding motifs would emerge.

The existence of nitrocellulose binding motifs may be avoided by one or more of several obvious strategies. RNA may be filtered through the nitrocellulose filters prior to SELEX to eliminate such motifs. Alternative matrices may be used in alternative rounds of SELEX, e.g., glass fiber filters. Alternative partitioning systems may be used, e.g., columns, sucrose gradients, etc. It is obvious that any given single process will lead to biases in the iterative process that will favor motifs that do not have increased binding to the target, but are selected by the selection process. It is, therefore, important to use alternating processes or screening processes to eliminate these motifs. It has been shown that the AGG repeats, like other motifs isolated as biases that are target independent, will tend to emerge most frequently when the affinity of the best sequences for the target are rather low or when the affinities of the best sequences are only slightly better than the affinity of the starting candidate mixture for the target.

Example 5

Isolation of a nucleic acid ligand for a mammalian receptor

Mammalian receptors often are proteins that reside within the cytomplasmic membranes of cells and respond to molecules circulating outside of those cells. Most receptors are not known to bind to nucleic-acids. The human growth hormone receptor responds to circulating human growth hormone, while the insulin receptor responds to circulating insulin. Receptors often have a globular portion of the molecule on the extracellular side of the membrane, and said globular portion specifically binds to the hormone (which is the natural ligand). Many disease states can be treated with nucleic acid ligands that bind to receptors.

Ligands that bind to a soluble globular domain of the human growth hormone receptor (shGHR) are identified and purified using the candidate mixture of Example 4. Again, the binding buffers are free of DTT. The soluable globular domain of the human growth hormone receptor is available from commercial and academic sources, having usually been created through recombinant DNA technology applied to the entire gene encoding a membrane-bound receptor protein. SELEX is used reiteratively until ligands are found. The ligands are cloned and sequenced, and binding affinities for the soluble receptor are measured. Binding affinities are measured for the same ligand for other soluble receptors in order to ascertain specifity, even though most receptors do not show strong protein homologies with the extracellular domains of other receptors. The ligands are used to measure inhibition of the normal binding activity of shGHR by measuring competitive binding between the nucleic acid ligand and the natural (hormone) ligand.

Example 6

Isolation of a nucleic acid ligand for a mammalian hormone or factor

Mammalian hormones or factors are proteins, e.g., growth hormone, or small molecules (e.g., epinephrine, thyroid hormone) that circulate within the animal, exerting their effects by combining with receptors that reside within the cytoplasmic membranes of cells. For example, the human growth hormone stimulates cells by first interacting with the human growth hormone receptor, while insulin stimulates cells by fist interacting with the insulin receptor. Many growth factors, e.g., granulocyte colony stimulating factor (GCSF), including some that are cell-type specific, first interact with receptors on the target cells. Hormones and factors, then, are natural ligands for some receptors. Hormones and factors are not known, usually, to bind to nucleic acids. Many disease states, for example, hyperthyroidism, chronic hypoglycemia, can be treated with nucleic acid ligands that bind to hormones or factors.

Ligands that bind to human insulin are identified purified using the starting material of Example 3. Human insulin is available from commercial sources, having usually been created through recombinant DNA technology. SELEX is used reiteratively until a ligand is found. The ligands are cloned and sequenced, and the binding affinities for human insulin are measured. Binding affinities are measured for the same ligand for other hormones or factors in order to ascertain specificity, even though most hormones and factors do not show strong protein homologies with human insulin. However, some hormone and factor gene families exist, including a small family of IGF, or insulin-like growth factors. The nucleic acid ligands are used to measure inhibition of the normal binding activity of human insulin to its receptor by measuring competitive binding with the insulin receptor and the nucleic acid ligand in the presence or absence of human insulin, the natural ligand.

Example 7

Preparation of column matrix for SELEX

Following the procedures as described in Example 9 below, it was shown that the polypeptide bradykinin is not retained by nitrocellulose. To enable the SELEX process on bradykinin, the protein was attached to Activated CH Sepharose 4B (Pharmacia LKB) as a support matrix according to standard procedures. The resulting matrix was determined to be 2.0 mM bradykinin by ninhydrin assay. See Crestfield et al. *J. Biol. Chem.* vol. 238, pp. 238, pp. 622–627 (1963); Rosen *Arch. Biochem. Biophys.*, vol. 67, pp. 10–15 (1957). The activated groups remaining on the support matrix were blocked with Tris. See Pharmacia, *Affinity Chromatography: Principles and Methods*, Ljungforetagen AB, Uppsala, Sweden (1988).

Spin-column separation was used to contact solutions of candidate mixtures with beaded matrix. In a general procedure for performing a selection step for SELEX, 40 μL of a 50:50 slurry of target sepharose in reaction buffer is transferred to a 0.5 ml Eppendorf tube. The RNA candidate mixture is added with 60 μL of reaction buffer, the reaction mixture is allowed to equilibrate for 30 minutes at 37° C. A hole is pierced in the bottom of the tube, and the tube is placed inside a larger Eppendorf tube, both caps removed, and the tubes spun (1000 RPM, 10", 21° C.) to separate the eluate. The small tube is then transferred to a new larger tube, and the contents washed four times by layering with 50 μL of the selected wash buffer and spinning. To conduct binding assays, the tube containing the radioactive RNA is transferred to a new Eppendorf tube and spun to dryness.

A bulk binding experiment was performed wherein a RNA candidate mixture comprised of a 30 nucleic acid randomized segment was applied to the bradykinin sepharose matrix. Using the spin-column technique, the binding of the bulk 30N RNA to various matrices was determined under high salt concentrations to determine the best conditions for minimizing background binding to the sepharose. Background binding of RNA to sepharose was minimized by blocking activiated groups on the sepharose with Tris, and using a binding buffer of 10 mM DEM and 10–20 mM KOAc. At this buffer condition, a binding curve of the randomized bulk solution of RNA yielded a bulk Kd of about $1.0 \times 10^{-5}$. See FIG. 20. The curve was determined by diluting the bradykinin sepharose against blocked, activated sepharose.

Example 8

Preparation of candidate mixtures enhanced in RNA motif structures.

In the preferred embodiment, the candidate mixture to be used in SELEX is comprised of a contiguous region of between 20 and 50 randomized nucleic acids. The randomized segment is flanked by fixed sequences that enable the amplification of the selected nucleic acids.

In an alternate embodiment, the candidate mixtures are created to enhance the percentage of nucleic acids in the candidate mixture possessing given nucleic acid motifs. Although two specific examples are given here, this invention is not so limited. One skilled in the art would be capable of creating equivalent candidate mixtures to achieve the same general result.

In one specific example, shown as Sequence A in FIG. 21, the candidate mixture is prepared so that most of the nucleic acids in the candidate mixture will be biased to form a helical region of between 4 and 5 base pairs, and a "loop" of either 20 or 21 contiguous randomized sequences. Both 5' and 3' ends of the sequence mixture will contain fixed sequences that are essential for the amplification of the nucleic acids. Adjacent these functional fixed sequences will be fixed sequences chosen to base pair with fixed sequences on the alternate side of the randomized region. Going from the 5' to the 3' end of the sequences, there will be 5 distinct regions; 1) fixed sequences for amplification; 2) fixed sequences for forming a helical structure; 3) 20 or 21 randomized nucleic acid residues; 4) fixed sequences for forming a helical structure with the region 2 sequences; and 5) fixed sequences for amplification. The A candidate mixture of FIG. 21 will be enriched in hairpin loop and symmetric and asymmetric bulged motifs. In a preferred embodiment, the candidate mixture would contain equal amounts of sequences where the randomized region is 20 and 21 bases long.

A second example, shown in FIG. 21 as sequence B, is designed to enrich the candidate mixture in nucleic acids held in the psuedoknot motif. In this candidate mixture, the fixed amplification sequences flank three regions of 12 randomized positions. The three randomized regions are separated by two fixed regions of four nucleotides, the fixed sequences selected to preferably form a four basepair helical structure. Going from the 5' to the 3' end of the sequence, there will be 7 district regions: 1) fixed sequences for amplification: 2) 12 randomized nucleotides; 3) fixed sequences for forming a helical structure; 4) 12 randomized nucleotides; 5) fixed sequences for forming a helical structure with the region 3 nucleotides; 6) 12 randomized nucleotides; and 7) fixed sequences for amplification.

In a preferred candidate mixture, the engineered helical regions are designed to yield alternating GC, CG, GC, CG basepairs. This basepair motif has been shown to give a particularly stable helical structure.

Example 9

Bulk binding of randomized RNA sequences to proteins not known to bind nucleic acids Following the general nitrocellulose selection procedures as described in Example 1 above for SELEX, a group of randomly selected proteins were tested to determine if they showed any affinity to a bulk candidate mixture of RNA sequences. The candidate mixture utilized in each experiment consisted of a 40N RNA solution (a randomized mixture having a 40 randomized nucleic acid segment) that was radiolabled to detect the percentage of binding. The candidate mixture was diluted in binding buffer (200 mM KoAc, 50 mM TrisoAc pH 7.7, 10 mM DTT) and 30 µL was used in a 60 µL binding reaction. To each reaction was added 20 µL, 10 µL or 1 µL of each protein. Binding buffer was added to reach a total volume of 60 µL. The reactions were incubated at 37° C. for 5 minutes and then subjected to filter binding.

The proteins tested were Acetylcholinesterase (MW 230,000); N-acetyl-β-D-glucosaminidase (MW 180,000); Actin (MW 43,000); Alcohol Dehydrogenase (240,000); Aldehyde Dehydrogenase (MW 200,000); Angiotensin (MW 1297); Ascorbate Oxidase (MW 140,000); Atrial Nutriuretic Factor (XW 3,064): and Bombesin (MW 1621). The proteins were purchased from Boehringer Ingelheim, and were utilized in the buffer composition in which they are sold.

The RNA candidate mixture used in each experiment contained 10,726 counts of radiolable, and a background binding of about 72 counts was found. The results are summarized in Table 9. All proteins tested except Acetylcholinesterase, N-acetyl-β-D-glucosaminidase and Actin were found to yield some bulk RNA affinity. Because of the low concentration of N-acetyl-β-D-glucosaminidase in solution as purchased, the results for that protein are not definitive. In addition, if any of the proteins tested do not bind to nitrocellulose—which is the case for bradykinin—no affinity would be detected in this experiment. Example 7 above discussing column supported bradykinin demonstrates that the failure to show bulk binding in this experiment does not mean that bulk binding does not exist for a given protein.

Example 10

Isolation of RNA ligand solution for Nerve Growth Factor

Nerve growth factor (NGF) is a protein factor that acts through a receptor on the outside surfaces of target cells. Antagonists toward growth factors and other hormones can act by blocking a receptor or by titrating the factor or hormone. An RNA was sought by the SELEX process that binds directly to NGF.

The starting RNAs were prepared exactly as in the case of HSV DNA polymerase (Example 11).

Two different experiments were done with NGF. The first was a ten round SELEX using low salt binding buffer, 3 minutes at 37 degrees incubation, and then filtration and a wash with the same buffer during the SELEX. The low salt binding buffer was 50 mM NaCl plus 50 mM Tris-acetate pH 7.5. The second experiment used as the binding buffer 200 mM NaCl plus 50 mM Tris-acetate pH 7.5, and then after filtration a wash with 50 mM Tris-acetate pH 7.5; this SELEX experiment went through only seven rounds.

The low salt experiment yielded 36 cloned sequences. Fifteen of the clones were nearly identical —#'s 2, 3, 4, 5, 6, 8, 11, 13, 19, 22, 28, 33, and 34 were identical, while #'s 15 and 25 had a single difference:

ACAUCGAUGACCGGAAUGCCGCACACAGAG (SEQ ID NO:19) +A G (15) (25)

A second abundant sequence, found six times, was (SEQ ID NO:20): CCUCAGAGCGCAAGAGUCGAAC-GAAUACAG (#'s 12, 20, 27, and 31) G C (21) (1)

From the high salt SELEX ten clones have been sequenced, but eight of them are identical and obviously related to the abundant (but minor) second class from the low salt experiment. The winning sequence is (SEQ ID NO:21):

----CUCAUGGAGCGCAAGACGAAUAGCUACAUA----

Between the two experiments a total of 14 different sequences were obtained (sequences with one difference are lumped together in this analysis); they are listed here, with the similarities overmarked and the frequencies noted. ngf.a through ngf.k are from the low salt experiment, while hsngf.a through hsngf.c are from the high salt experiment:

11227–11232 (1990). The second form of DNA polymerase, a heterodimer, is purified from HSV-1 infected cells according to Crute, J. J. and Lehman, I. R., J. Biol. Chem., 264, 19266–19270 (1989); the heterodimer contains one peptide

|  |  | Frequency |
|---|---|---|
| ngf.a | xxxxxxxxxxx  #######<br>ACAUCGAUGACCGGAAUGCCGCACACAGAG | 15/36 (SEQ ID NO: 22) |
| ngf.b | xxxxxxxxxxx           #######<br>CCUCAGAGCGCAAGAGUCGAACGAAUACAG<br>$$$$$$$$$$$$$$    $$$$       $$$$ | 6/36 (SEQ ID NO: 23) |
| ngf.c | #######       xxxxxxxxxxx<br>CGGGUGAUUAGUACUGCAGAGCGGAAUGAC | 5/36 (SEQ ID NO: 24) |
| ngf.d | #######      xxxxxxxxxxx<br>UGCGAUAAGACUUGCUGGGCGAGACAAACA | 3/36 (SEQ ID NO: 25) |
| ngf.e | #######                xxxxxxxxxxx<br>AGUCCACAGGGCACUCCCAAAGGGCAAACA | 1/36 (SEQ ID NO: 26) |
| ngf.f | xxxxxxxxxxx#######<br>ACUCAUGGAGCGCUCGACGAUCACCAUCGA | 1/36 (SEQ ID NO: 27) |
| ngf.g | xxxxxxxxxxx           #######<br>CAAGGGAGAAUGUCUGUAGCGUCCAGGUA | 1/36 (SEQ ID NO: 28) |
| ngf.h | xxxxxxxxxxx  #######<br>CGACGCAGAGAUACGAAUACGACAAAACGC | 1/36 (SEQ ID NO: 29) |
| ngf.i | ######xxxxxxxxxxxx<br>GAGGGUGAGGUGGGAGGCAGUGGCAGUUUA | 1/36 (SEQ ID NO: 30) |
| ngf.j | xxxxxxxxxxx#######<br>UGAACUAGGGGGAGGGAGGGUGGAAGACAG | 1/36 (SEQ ID NO: 31) |
| ngf.k | #######  xxxxxxxxxxx<br>GUGGAGGGGACGUGGAGGGGAGAGCAAGA | 1/36 (SEQ ID NO: 32) |
| hsngf.a | xxxxxxxxxxx#######<br>CUCAUGGAGCGCAAGACGAAUAGCUACAUA<br>$$$$    $$$$$$$$$$$$$$      $$$$ | 8/10 (SEQ ID NO: 33) |
| hsngf.b | xxxxxxxxxxx      #######<br>CCAUAGAGGCCACAAGCAAAGACUACGCA | 1/10 (SEQ ID NO: 34) |
| hsngf.c | #######     xxxxxxxxxxx<br>CCUACAAGAAAAGAGGGAAGGAGAAAAAAA | 1/10 (SEQ ID NO: 35) |

While no obvious secondary structure is embedded within the similar sequences, it is likely that the winning sequences place critical nucleotides into a structure that is well fit by an NGF binding site.

A binding assay of nucleic acid hsngf.a to NGF was performed, and this nucleic acid was found to have a Kd of about 20 to 30 fold higher than the bulk 30N candidate mixture. The same nucleic acid was also found to have a lower or equal affinity to R17 coat protein and tPA than a 30N candidate mixture. Thus, the SELEX derived nucleic acid ligand hsngf.a is a selective ligand to NGF.

Example 11

Isolation of a nucleic acid ligand for HSV-1 DNA polymerase

Herpes simplex virus (HSV-1) is a DNA-containing virus of mammals. HSV-1, like many DNA-containing viruses, encodes its own DNA polymerase. The HSV-1 DNA polymerase has been purified in two forms, which have different qualities but each of which will catalyze DNA replication in vitro. The simple form, which is one polypeptide, is purified from cells expressing the cloned gene according to Hernandez, T. R. and Lehman, I. R., J. Biol. Chem., 265, corresponding to the polymerase itself and another, UL42, also encoded by HSV-1.

SELEX was performed on both the single polypeptide and the heterodimer. The binding buffer in each case was 50 mM potassium acetate plus 50 mM Tris acetate, pH 7.5, and 1 mM dithiothreitol. Filtration to separate bound RNA was done after four minutes of incubation at 37 degrees; the filters were washed with binding buffer minus dithiothreitol.

The RNA candidate mixture was transcribed from DNA as described previously. As is the case in other embodiments, the DNA sequence includes a bacteriophage T7 RNA polymerase promoter sequence that allows RNA to be synthesized according to standard techniques. cDNA synthesis during the amplification portion of SELEX is primed by a DNA of the sequence:

cDNA primer (PCR primer 1)(SEQ ID NO:36): 5' GCCGGATC-
CGGGCCTCATGTGAA 3'

The DNA primers used to amplify the cDNA in that portion of the SELEX cycle include, in one of them, the T7 promoter; that PCR primer has the sequence:

PCR primer 2(SQ ID NO:32): 5'CCGAAGCTTAATACGACT-
CACTATAGGGAGCTCAGAATAAACGCTCAA 3'

The initial randomized DNA included the sequence with the T7 promoter, 30 randomized positions, and the fixed sequence complementary to PCR primer 1. The RNA that is used to begin the first cycle of SELEX thus has the sequence (SEQ ID NO:38):

pppGGGAGCUCAGAAUAAACGCUCAA—30W—UUCGA-CAUGAGGCCCGGAUCCGGC

SELEX was performed for seven rounds, after which cDNA was prepared and cloned as described previously. The series of sequences designated "H" were obtained with the simple HSV DNA polymerase as the target, while the "U" series was obtained with the heterodimeric polymerase that includes the UL42 polypeptide.

About 25% of the sequences from the H series contain an exact sequence of 12 nucleotides at the 5' end of the randomized region (the upper case letters are from the randomized region). In some sequences the length between the fixed primers was not exactly 30 nucleotides, and in one case (H2) a large deletion was found within the randomized region. The members of this H subset include:

xxxxxxxxxxxx
H5: --cgcucaaUAAGGAGGCCACGGACAACAUGGU ACAGCuucgaca-- (SEQ ID NO:34)
H10: --cgcucaaUAAGGAGGCCACAACAAAIGGAGA CAAAuucgaca-- (SEQ ID NO:40)
H4: --cgcucaaUAAGGAGGCCACACACAUAGGUAG ACAUGuucgaca-- (SEG ID NO:41)
H19: --cgcucaaUAAGGAGGCCACAUACAAAAGGAU GAGUAAAuucgaca-- (SEQ ID NO:42)
H20: --cgcucaaUAAGGAGGCCACAAAUGCUGGUCC ACCGAGAuucgaca-- (SEQ ID NO:43)
H38: --cgcucaaUAGGGAGGGCACGGGAAGGGUGAG UGGAUAuucgaca-- (SEQ ID NO:44)
H2: --cgcucaaUAAGGAGGCCACAAGuucgaca——(SEQ ID NO:45)

Two members of the U series share this primary sequence motif:
U9: ——cgcucaaUAAGGAGGGCCACAGAUGUAA UGGAAACuucgaca——
U13: ——cgcucaaUAAGGAGGCCACAUACAAAAG GAUGAGUAAAuucgaca——

The remaining sequences from the H and U series show no obvious common sequence; in addition, no sequences from the seventh round emerged as winning single sequences in either series, suggesting that more rounds of SELEX will be required to find the best ligand family for inhibiting HSV DNA polymerase.

It appears that the primary sequence (SEQ ID NO:46 and SEQ ID NO:47).

--cgcucaaUAAGGAGGCCAC . . . .

may be a candidate for an antagonist species, but those members of the series have yet to be tested as inhibitors of DNA synthesis. It appears that the fixed sequence just 5' to the UAAGGAGGCCAC must participate in the emergence of this subset, or the shared 12 nucleotides would have been positioned variably within the randomized region.

Example 12

Isolation of a nucleic acid ligand for E. coli Ribosomal Protein S1

The E. coli 30S ribosomal protein S1 is the largest of the 21 30S proteins. The protein has been purified based on its high affinity for polypyrimidines, and is thought to bind rather tightly to single stranded polynucleotides that are pyrimidine rich. It was questioned if the RNA identified as a ligand solution by SELEX was in any way more information rich than a simple single stranded RNA rich in pyrimidines.

The RNAs, DNAs, cDNA primer (PCR primer 1), and PCR primer 2 were identical to those used for HSV-1 DNA polymerase (see, Example 11). The binding buffer contained 100 mM ammonium chloride plus 10 mM magnesium chloride plus 2 mM dithiothreitol plus 10 mM Tris-chloride, pH 7.5. Binding was at room temperature, and complexes were once again separated by nitrocellulose filtration. The protein was purified according to I. Boni et al., European J. Biochem., 121, 371 (1982).

After 13 SELEX rounds, a set of 25 sequences was obtained. More than twenty of those sequences contained pseudoknots, and those pseudoknots contain elements in common.

The general structure of pseudoknots can be diagrammed as;

STEM 1a—LOOP 1—STEM 2a—STEM 1b—LOOP 2 STEM 2b (See FIG. 31)

Most of the S1 protein ligands contain:
STEM 1 of 4 to 5 base pairs, with a G just 5' to LOOP 1
LOOP 1 of about 3 nucleotides, often ACA
STEM 2 of 6 to 7 base pairs, stacked directly upon STEM 1
LOOP 2 of 5 to 7 nucleotides, often ending with GGAAC A reasonable interpretation of these data is that LOOP 2 is stretched across STEM 1 so as to hold that loop rigidly in a form that simplifies and enhances the binding of the single strand to the active site of protein S1. A picture of the consensus pseudoknot in two dimensions would look like this:

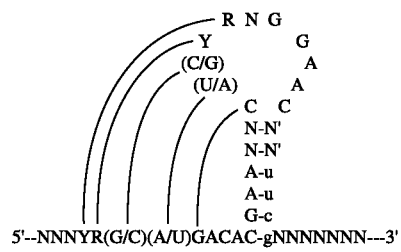

5'--NNNYR(G/C)(A/U)GACAC-gNNNNNNN---3'

In such figures the base pairs are shown as lines and dashes, the selections of bases from the randomized region are shown in upper case letters, Y is a pyrimidine, R is a purine, N- N' means any base pair, N means any nucleotide, and the lower case letters are from the fixed sequence used for PCR amplifications.

It appears that single stranded polynucleotide binding proteins and domains within proteins will often select, during SELEX, a pseudoknot which presents the extended, rigid single strand called LOOP 2 to the binding site of the protein in a manner that maximizes the interactions with that site. Thus, when the HIV-1 RT psueodoknot emerged, it is reasonable to think that the single stranded domain LOOP 2 is bound within the region of RT that holds the template strand during replication. That is, it appears reasonable that most replication enzymes (DNA polymerase, RNA polymerase, RNA replicases, reverse transcriptases) will have a domain for holding the template strand that might prefer a pseudoknot as the ligand of choice from SELEX.

Example 13

Isolation of a nucleic acid ligand to HIV-1 rev protein

The HIV-1 rev protein's RNA-recognition site appears to be complex, and its function is essential to the productive infection of an epidemic viral disease. See, Olsen et al., Science, vol. 247, pp. 845–848 (1990). The SELEX process on this protein was performed in order to learn more about the recognition element and to isolate a ligand to the target protein.

A candidate mixture was created with a 32 nucleotide long random region as described above in Example 2. It was found that the rev protein could saturably bind the starting candidate mixture with a half-maximal binding occuring at about $1 \times 10(-7)$ M as determined by nitocellulose assays. All RNA-protein binding reactions were performed in a binding buffer of 200 mM KOAc, 50 mM Tris-HCl pH 7.7, 10 mM dithiothreitol. RNA and protein dilutions were mixed and stored on ice for 30 minutes then transferred to 37 degrees for 5 minutes. (In binding assays the reaction volume is 60 ul of which 50 ul is assayed; in SELEX rounds the reaction volume is 100 ul.) Each reaction is suctioned through a prewet (with binding buffer) nitrocellulose filter and rinsed with 3 mls of binding buffer after which it is dried and counted for assays or subjected to elution as part of the SELEX protocol. Ten rounds of SELEX were performed, using a RNA concentration of about $3 \times 10(-5)$ M. The concentration of rev protein was $1 \times 10(-7)$ in the first round, and $2.5 \times 10(-8)$ in all subsequent rounds. The intial candidate mixture was run over a nitrocellulose filter to reduce the number of sequences that have a high affinity for nitrocellulose. This process was also repeated after rounds 3, 6, and 9. The cDNA product was purified after every third round of selection to avoid anomalously sized species which will typically arise with repeated rounds of SELEX. After 10 rounds the sequence in the variable region of the RNA population was nonrandom as determined by dideoxy-chain termination sequencing. 53 isolates were cloned and sequenced.

Each of the cloned sequences are listed in Table 10. All sequences were analysed by the Zucker RNA secondary structure prediction program. See, Zucker, Science, vol. 244, pp. 48–52 (1989); Jaeger et al., Proc. Natl. Acad. Sci. USA, vol. 86, pp. 7706–7710 (1989). On the basis of common secondary structure all sequences have been grouped into three common motifs as shown in Table 11. Motifs I and II are similiar in conformation including a bulged loop closed at each end by a helix. This generalized structure has been illustrated schematically in Table 12, and the domains labeled for easy discussion; that is from 5' to 3' Stem 1a (which base pairs to the 3' Stem 1b), Loop 1, Stem 2a, Loop 3, Stem 2b, Loop 2, and Stem 1b. The sequences which fit in the various domains are listed for individual sequences in Table 12. (Note that in sequence 3a, the homologous alignment is flipped 180 degrees so that it is Stem 1 which is closed with a loop.) The energies of folding of the RNA molecule (including the fixed flanking sequences) are shown in Table 13.

The wild-type rev responsive element (RRE) that has been determined to be at least minimally involved in binding of rev to HIV-1 transcripts was also folded by this program, and is included in Tables 12 and 13.

The sequences were also searched for related subsequences by a procedure based on that described in Hertz et al. Comput. Appl. Biosci., vol.6. pp.81–92 (1990). Two significant patterns were identified. Each isolate was scored to identify its best match to the patterns, the results of which can be seen in Table 13. The related subsequences motifs are presented by the common secondary structures in similiar conformations; that is, the first sequence UUGAGAUACA (SEQ ID NO:48) is commonly found as Loop 1 plus the 3' terminal CA, which pairs with the UG at the 5' end of the second information rich sequence UGGACUC (commonly Loop 3). There is also a strong prediction of base-pairing of the GAG of sequence I to the CUC of sequence II. Motif II is similiar to Motif I in that the subsequence GAUACAG predominates as a loop opposite CUGGACAC with a similiar pairing of CA to UG. Motif II differs in the size of the loops and some of the sequence particularly in the absence of predicted base-pairing across the loop one domain of the wild-type RRE closely resembles Motif II. Motif III is the least like all the other sequences, although it is characterized by two bulged U's adjacent to base-paired GA-UC as in Motif I. Unfortunately, further comparisons are complicated because the folding pattern of Motif III involves the 3' fixed sequence region in critical secondary structures; because these sequences are invariant there is no way to analyse the importance of any one of them. The folded sequences of representatives of each Motif is shown in FIG. 23 with the folded sequence of the wild-type RRE.

The sequences were further analyzed for their affinity to the rev protein. Templates were PCR'd from a number of clones from which labeled in vitro transcripts were prepared and individually assayed for their ability to bind rev protein. These binding curves are shown in FIGS. 24 to 28. Labeled transcripts from oligonucleotide templates were also synthesized which contain the wild-type RRE discussed above, and what is inferred to be the consensus motif in a highly stable conformation. To control for experimental variations, the best binding sequence, isolate 6a, was assayed as a standard in every binding experiment. The RNA-protein mixtures were treated as described above except that diluted RNA's were heated to 90 degrees for 1 minute and cooled on ice prior to mixing. The average Ka for isolate 6a was $8.5 \times 10(-8)$ M, and the results of this experiment are shown in Table 13.

The binding curves of FIG. 24 shows that the evolved population (P) improved approximately 30 fold for binding to rev protein relative to the starting candidate mixture. The binding of the wild-type RRE closely resembles that of the most abundant clone, 1c. This experiment also illustrates how sensitive the rev binding interaction is to secondary structure. Isolates 6a and 6b are identical in the regions of high information content, but are quite different at the level of secondary structure resulting in changes at three nucleotide positions. These changes, which predict the base-pairing of Stem 1, lower the affinity of 6b by 24fold. Sensitivity to secondary structure anomalies is further illustrated by the binding of isolate 17 as shown in FIG. 25. Isolate 17 has the maximum information score as shown in Table 12. However, there is an extra bulged U at the 5' end of Loop 1 as shown in Table 11. This extra U results in isolate 17's reduced affinity for rev as compared to other sequences of Motif I. In contrast, single nucleotide deletions of Loop 2 sequences, even those that diminish the prospect of cross-bulge base-pairing are well tolerated by the rev interaction.

Another compelling commonality is the conservation of the sequence ACA opposite UGG where the CA pairs with the UG to begin Stem 2. This sequence is shared by Motifs I and II as well as by the wild-type RRE. Sequences 11 and 12 exhibit a base-pair substitution at this position (see Table 12), and sequence 12 was tested and has reduced affinity compared to most of the other Motif I sequences.

The RNA sequences determined by SELEX to be rev ligands may be classified by primary and secondary structure. A consensus emerges of an asymmetric bulge flanked by two helices in which are configured specifically conserved single and double stranded nucleotides. Although base-pairing across the bulge is predicted for many of the sequences isolated (Motif I), it may not be essential or crucial to rev interaction. optimal sizes for Loop 1 appear to be 8 (Motif I) or 6 (Motif III) where there is an observed penalty for sizes of 9 or 3. Optimal sizes for Loop 3 are 5 and 4. In addition, the interaction of rev with the various domains of these ligands may be additive. Motif II resembles Moftif I primarily at the junction of Loops 1 and 3 at Stem 2. Motif III resembles Motif I at the junction of Loops 1 and 3 at Stem 1. Consensus diagrams of the Motif I and II nucleic acid solutions for HIV-rev are shown in FIGS. 29 and 30.

The abundance of sequences in the cloned population is not strictly correlated with affinity to rev protein. It is possible that the concentration of rev protein used throughout the SELEX process was sufficient to bind a signifigant percentage of all these isolates. As a consequence, there may have been selection for replicability of cDNA and DNA during PCR superimposed on a low stringency selection for binding to rev. The highly structured nature of these ligands and the possible differences in the efficiency of cDNA synthesis on these templates reinforces this potential replicative bias. Also, there is some mutation that occurs during the SELEX process. The sequence 6a so resembles 6b that they must have a common ancestor. This relatively late arrival during the rounds of SELEX may explain the paucity of this sequence irrespective of its higher affinity to the target. In the same manner, some of the ligands that have emerged may have mutated relatively recently during selection from ancestor sequences that exist in the intial candidate mixture but are not represented in the cloned population.

The invention disclosed herein is not limited in scope to the embodiments disclosed herein. As disclosed, the invention can be applied by those of ordinary skill in the art to a large number of nucleic acid ligands and targets. Appropriate modifications, adaptations and expedients for applying the teachings herein in individual cases can be employed and understood by those skilled in the art, within the scope of the invention as disclosed and claimed herein.

TABLE 1

1) 5'-TAATACGACTCACTATAGGGAGCCAACACCACAATTCCAATCAAG-3' (SEQ ID NO: 4)
2) 5'-GGGCTATAAACTAAGGAATATCTATGAAAG-3' (SEQ ID NO: 5)
3) 5'-GAATTGTGGTGTTGGCTCCCTATAGTGAGTCGTATTA-3' (SEQ ID NO: 6)
4) 5'-ATATTCCTTAGTTTATAGCCCNNNNNNNNAGGCTCTTGATTG-3' and (SEQ ID NO: 7)
5) 5'-GTTTCAATAGAGATATAAAATTCTTTCATAG-3' (SEQ ID NO: 8)

TABLE 2

1a) 5'-taatacgactcactatagggagccaacaccacaattccaatcaag-3' (SEQ ID NO: 49)
(bridging oligo for 5' construction and 5'PCR oligo)

1b) 5'-taatacgactcactatagggagcatcagactttaatctgacaatcaag-3' (SEQ ID NO: 50)
(bridging oligo for 5' construction and 5'PCR oligo)

2) 5'-atctatgaaagaattttatatctc-3' (SEQ ID NO: 51)
(bridging oligo for 3' ligation)

3a) 5'-gaattgtggtgttggctccctatagtgagtcgtatta-3' (SEQ ID NO: 52)
(template construction oligo)

3b) 5'-tcagattaaaagtctgatgctccctatagtgagtcgtatta-3' (SEQ ID NO: 53)
(template construction oligo)

4) 5'-tttcatagatnnnnnnnnnnnnnnnnnnnnnnnnnnnncttgattg-3' (SEQ ID NO: 54)
(template construction oligo)

5) 5'-ccggatccgtttcaatagagatataaaattc-3' (SEQ ID NO: 55)
(3' cloning oligo and template construction oligo)

6) 5'-gtttcaatagagatataaaattctttcatag-3' (SEQ ID NO: 56)
(3' primer for PCR)

7) 5'-ccgaagcttctaatacgactcactatagggag-3' (SEQ ID NO: 57)
(5' PCR primer for cloning and for inhibition assay)

8) 5'-agagatataaaattctttcatagnnnnttttcccgnnnnnnnnncggaannctt-gattgtcagattaaaagtc-3' (SEQ ID NO: 58)
(random template for SELEX experiment 3)

9) 5'-gacgttgtaaaacgacggcc-3' (SEQ ID NO: 59)
(3' PCR and RT extension primer for inhibition assay)

TABLE 3 starting RNA
 5'-gggagcaucagacuuuuaaucugacaaucaag-[-32 n's-]-
              -aucuaugaaagaauuuuauaucucuauugaaac-3'
              (SEQ ID NO: 60)

isolate

| | | | |
|---|---|---|---|
| 1.1 | ucaagAAUUCCGUUUUCAGUCGGGAAAAACUGAACAaucu | (13) | (SEQ ID NO: 61) |
| 1.2 | ucaagCGUAGGUUAUGAAUGGAGGAGGUAGGGUCGUAaucu | (5) | (SEQ ID NO: 62) |
| 1.3a | ucaagAAUAUCUUCCGAAGCCGAACGGGAAAACCGGCaucu | (1) | (SEQ ID NO: 63) |
| 1.3b | --------------------G--------------------A----- | (1) | (SEQ ID NO: 64) |
| 1.3c | ---------C---------G------------------------- | (1) | (SEQ ID NO: 65) |
| 1.3d | --------------------G-----------------------C-- | (1) | (SEQ ID NO: 66) |
| 1.3e | --------------------G-----------------------A-- | (1) | (SEQ ID NO: 67) |
| 1.4 | ucaagGGCAUCUGGGAGGGUAAGGGUAAGGUUGUCGGaucu | (4) | (SEQ ID NO: 68) |
| 1.5 | ucaagCCCACGGAUGUCGAAGGUGGAGGUUGGGCGGCaucu | (3) | (SEQ ID NO: 69) |
| 1.6 | ucaagAAGAAGAUUACCCAAGCGCAGGGGAGAAGCGCaucu | (2) | (SEQ ID NO: 70) |
| 1.7 | ucaagGAAUCGACCCAAGCCAAAGGGGAUAAUGCGGCaucu | (2) | (SEQ ID NO: 71) |
| 1.8 | ucaagGAUUAACCGACGCCAACGGGAGAAUGGCAGGGaucu | (2) | (SEQ ID NO: 72) |
| 1.9a | ucaagAGAGUAUCAUC GUGCCGGCGGGAUAUCGGCGaucu | (1) | (SEQ ID NO: 73) |
| 1.9b | ------------------C-------------------------- | (1) | (SEQ ID NO: 74) |
| 1.10a | ucaagUUUGAACAAGCGGAACAUGCACAGCUACACUCaucu | (1) | (SEQ ID NO: 75) |
| 1.10b | --------C--------------------------C---------- | (1) | (SEQ ID NO: 76) |
| 1.11 | ucaagCUCACGGAUGUCGAAGGUGGAGGUUGGGCGGCAuc | (1) | (SEQ ID NO: 77) |
| 1.12 | ucaagCAUAGACCGCGUAGGGGGAGGUAGGAGCGGCCaucu | (1) | (SEQ ID NO: 78) |
| 1.13 | ucaagCUCUUUCAUAGACCGCGGAGGAGGUUGGGAGaucu | (1) | (SEQ ID NO: 79) |
| 1.14 | ucaagUUCCUAGUAGACUGAGGGUGGGAGUGGUGGAUGucu | (1) | (SEQ ID NO: 80) |
| 1.15 | ucaagCCAAUUACUUAUUUCGCCGACUAACCCCAAGAaucu | (1) | (SEQ ID NO: 81) |
| 1.16 | ucaagGAGGCCAAUUCCAUGUAACAAGGUGCAACUAAUaucu | (1) | (SEQ ID NO: 82) |
| 1.17 | ucaagUGCGUAUGAAGAGUAUUUAGUGCAGGCCACGGaucu | (1) | (SEQ ID NO: 83) |
| 1.18 | ucaagUAAUGACCAGAGGCCCAACUGGUAAACGGGCGucu | (1) | (SEQ ID NO: 84) |
| 1.19 | ucaagAGACUCCACCUGACGUGUUCAACUAUCUGGCaucu | (1) | (SEQ ID NO: 85) |

Nucleotides of the fixed regions are shown as lower case letters

TABLE 4

Pseudoknot Motif

| | | | |
|---|---|---|---|
| 1.1 | ucaagAAUUCCGUUUUCAGUCGGGAAAAACUGAACAaucu | (13) | (SEQ ID NO:86) |
| 1.3a | ucaagAAUAUCUUCCGAAGCCGAACGGGAAAACCGGCaucu | (1) | (SEQ ID NO:87) |
| 2.9 | ucaagGUUUCCGAAAGAAAUCGGGAAAACUGucu | (1) | (SEQ ID NO:88) |
| 2.4a | ucaagUAGAUAUCCGAAGCUCAACGGGAUAAUGAGCaucu | (3) | (SEQ ID NO:89) |
| 2.7a | ucaagAUAUGAUCCGUAAGAGGACGGGAUAAACCUCAa-cu | (3) | (SEQ ID NO:90) |
| 1.7 | ucaagGAAUCGACCCAAGCCAAAGGGGAUAAUGCGGCaucu | (2) | (SEQ ID NO:91) |
| 2.11 | ucaagUCAUAUUACCGUUACUCCUCGGGAUAAAGGAGaucu | (1) | (SEQ ID NO:92) |
| 1.18 | ucaagUAAUGACCAGAGGCCCAACUGGUAAACGGGCGGucu | (1) | (SEQ ID NO:93) |
| 1.8 | ucaagGAUUAACCGACGCCAA-CGGGAGAAUGGCAGGGaucu | (2) | (SEQ ID NO:94) |
| 2.1b | ucaagAAUAUAUCCGAACUCGA-CGGGAUAACGAGAAGaGcu | (7) | (SEQ ID NO:95) |

TABLE 4-continued

| | | | |
|---|---|---|---|
| 1.6 | ucaagAAGAAGAUUACCCAAGCGCA-GGGGAGAAGCGCaucu | (2) | (SEQ ID NO:96) |
| 2.10 | ucaagUAAAUGAGUCCGUAGGAGG-CGGGAUAUCUCCAAcu | (1) | (SEQ ID NO:97) |
| 1.9b | ucaagAGAGUAUCAUCCGUGCCGG--CGGGAUAUCGGCGaucu | (1) | (SEQ ID NO:98) |
| 2.12 | ucaagAAUAAUCCGACUCG---CGGGAUAACGAGAAGAGcu | (1) | (SEQ ID NO:99) |
| 1.10b | ucaagUUCGAACAAG--CGGAACAUGCACAGCCACACUCaucu | (1) | (SEQ ID NO:100) |
| 2.3a | caagUUAAACAUAAUCCGUGAUCUUUCACACGGGAGaucuaugaaaga | (7) | (SEQ ID NO:101) |
| 2.2b | aaucaagUACCUAGG-UGAUAAAGGGAGAACACGUGUGa-cu | (1) | (SEQ ID NO:102) |
| 2.2b | aaucaagUACCUAGGUGAUAAA-AGGGAGAACACGUGUGa-cu | (1) | (SEQ ID NO:103) |
| 2.5a | ucaagAUAGUAUCCGUCUUGAUCAUCGGGACAAAUGaucu | (3) | (SEQ ID NO:104) |
| 2.6b | ucaagUGAAACUUAACCGUUAUCAUAGAUCGGGACAAaucuaugaa | (2) | (SEQ ID NO:105) |

Nitrocellulose retention motif

| | | | |
|---|---|---|---|
| 1.2 | ucaagCGUAGGUUAUGAAUGGAGGAGGUAGGGUCGUAaucuaug | (5) | (SEQ ID NO:106) |
| 1.4 | aucugacaaucaagGGCAUCUGGGAGGGUAAGGGUAAGGUUGUCGGaucu | (4) | (SEQ ID NO:107) |
| 1.5 | ucaagCCCACGGAUGUCGAAGGUGGAGGUUGGGCGGCaucu | (3) | (SEQ ID NO:108) |
| 1.11 | ucaagCUCACGGAUGUCGAAGGUGGAGGUUGGGCGGCAuc | (1) | (SEQ ID NO:109) |
| 1.12 | ucaagCAUAGACCGCGUAGGGGGAGGUAGGAGCGGCCaucuaug | (1) | (SEQ ID NO:110) |
| 1.13 | ucaagCUCUUUCAUAGACCGCGGAGGAGGUUGGGAGaucuaugaaaga | (1) | (SEQ ID NO:111) |
| 1.14 | ucaagUUCCCUAGUAGACUGAGGGUGGGAGUGGUGGAUGucuau | (1) | (SEQ ID NO:112) |

Secondary structures as predicted by the Zuker program are shown with overlined arrows which highlight the inverted repeats indicative of base-pairing.

TABLE 5

| Clone | Freq. | Stem 1(a) | Loop 1 | Stem 2(a) | Loop 2 | Stem 1(b) | Loop 3 | Stem 2(b) | Seq. No. |
|---|---|---|---|---|---|---|---|---|---|
| 2.3a | 9* | UCCGUG | A | UCUUUCA | — | CACGGG | AGaucua | ugaaaga | SEQ ID NO: 113 |
| 2.9 | 1 | UUCCGA | A | AGA | AA | UCGGGA | AAACUG | ucu | SEQ ID NO: 114 |
| 2.7a | 4* | UCCGU | UAA | GAGG | — | ACGGG | AUAAA | CCUC | SEQ ID NO: 115 |
| 1.1 | 13 | UUCCG | UU | UUCAGU | — | CGGGA | AAA | ACUGAA | SEQ ID NO: 116 |
| 1.3c | 5* | UUCCG | AG | GCCG | AA | CGGGA | AAAC | CGGC | SEQ ID NO: 117 |
| 1.18 | 1 | ACCAG | AG | GCCC | AA | CUGGU | AAAC | GGGC | SEQ ID NO: 118 |
| 2.4a | 7* | UCCG | AA | GCUCA | A | CGGG | AUAA | UGAGC | SEQ ID NO: 119 |
| 2.1b | 19* | UCCG | AA | CUCG | A | CGGG | AUAA | CGAG | SEQ ID NO: 120 |
| 2.10 | 1 | UCCG | UA | GGAGG | — | CGGG | AUA | UCUCC | SEQ ID NO: 121 |
| 1.9b | 2* | UCCG | — | UGCCGG | — | CGGG | AUA | UCGGCG | SEQ ID NO: 122 |
| 2.12 | 1 | UCCG | A | CUCG | — | CGGG | AUAA | CGAG | SEQ ID NO: 123 |
| 1.10b | 2* | UCCG | AA | CA | AG | CGGA | ACA | UG | SEQ ID NO: 124 |
| 2.5a | 6* | UCCG | UUCUU | GAUCAU | — | CGGG | ACAA | AUGauc | SEQ ID NO: 125 |
| 2.11 | 1 | CCG | UUA | CUCCU | — | CGG | GAUAA | AGGAG | SEQ ID NO: 126 |
| 1.8 | 2 | CCG | AC | GCCA | A | CGG | GAGAA | UGGC | SEQ ID NO: 127 |
| 2.6b | 5* | CCG | UUA | UCAUAGAU | — | CGG | GACAA | aucuauga | SEQ ID NO: 128 |

TABLE 5-continued

| Clone | Freq. | Stem 1(a) | Loop 1 | Stem 2(a) | Loop 2 | Stem 1(b) | Loop 3 | Stem 2(b) | Seq. No. |
|---|---|---|---|---|---|---|---|---|---|
| 1.7 | 2 | CCC | AA | GCC | AAA | GGG | GAUAAUGC | GGC | SEQ ID NO: 129 |
| 1.6 | 2 | CCC | AA | GCGC | A | GGG | GAGAA | GCGC | SEQ ID NO: 130 |
| 2.2b | 17* | CCU | AG | GUG | AUAAA | AGG | GAGAA | CAC | SEQ ID NO: 131 |

TABLE 6 starting RNA
5'-gggagccaacaccacaauuccaaucaag-[32 n's-]-
          aucuaugaaagaauuuuauaucucuauugaaac-3' (SEQ ID NO: 132)

isolate

| | | | |
|---|---|---|---|
| 2.1a | ucaag AAUAUA UCCGAACUCGACGGGAUAACGAGAA Gaucu | (3) | (SEQ ID NO: 133) |
| 2.1b | ----------------------------------------------G-- | (7) | (SEQ ID NO: 134) |
| 2.1c | -----CA----------------------------------------G-- | (1) | (SEQ ID NO: 135) |
| 2.1d | --------C--------------------------------------G-- | (1) | (SEQ ID NO: 136) |
| 2.1e | --------------------------G---------------------G-- | (1) | (SEQ ID NO: 137) |
| 2.1f | ----------------------------------------------G-- | (1) | (SEQ ID NO: 138) |
| 2.1g | ----------------------------------------------C-C-- | (1) | (SEQ ID NO: 139) |
| 2.1h | -------------A----------------------------------G-- | (1) | (SEQ ID NO: 140) |
| 2.1i | ------GU---------------------------------------G-- | (1) | (SEQ ID NO: 141) |
| 2.1j | ----------------------------------------------A--G-- | (1) | (SEQ ID NO: 142) |
| 2.1k | --------------C---------------------------------G-- | (1) | (SEQ ID NO: 143) |
| 2.2a | ucaagUACCUAGGUGAUAAAAGGGAGAACACGUGA acu | (1) | (SEQ ID NO: 144) |
| 2.2b | ------------------------------------------UG--- | (13) | (SEQ ID NO: 145) |
| 2.2c | -----------------------------------A---G--- | (2) | (SEQ ID NO: 146) |
| 2.2d | ------------------------------------------G--- | (1) | (SEQ ID NO: 147) |
| 2.3a | ucaagUUAAACAUAAUCCGUGAUCUUUCACACGGGAGaucu | (7) | (SEQ ID NO: 148) |
| 2.3b | -----------------------------------------------C-- | (1) | (SEQ ID NO: 149) |
| 2.3c | ------------------------------------------A---A-- | (1) | (SEQ ID NO: 150) |
| 2.4a | ucaagUA GAUAUCCGAAGCUCAACGGGAUAAUGAGCaucu | (3) | (SEQ ID NO: 151) |
| 2.4b | -----C-AAU--------------------------------------- | (1) | (SEQ ID NO: 152) |
| 2.4c | ---------------------------------------G--- | (1) | (SEQ ID NO: 153) |
| 2.4d | -----A------------------------------------------ | (1) | (SEQ ID NO: 154) |
| 2.4e | -----U--AU--------------U----------------------- | (1) | (SEQ ID NO: 155) |
| 2.5a | ucaagAUAGUAUCCGUUCUUGAUCAUCGGGACAAAUGaucu | (3) | (SEQ ID NO: 156) |
| 2.5b | ------C----------------------------------------- | (1) | (SEQ ID NO: 157) |
| 2.5c | -----U------------------------------------------ | (1) | (SEQ ID NO: 158) |
| 2.5d | ----------------A------------------------------- | (1) | (SEQ ID NO: 159) |
| 2.6a | ucaagUGAA CUUAACCGUUAUCAUAGAUCGGGACAAa cu | (1) | (SEQ ID NO: 160) |
| 2.6b | ----------A---------------------------------u-- | (2) | (SEQ ID NO: 161) |
| 2.6c | ---------------------------------------------u-- | (1) | (SEQ ID NO: 162) |
| 2.6d | ----------A-----------------U------u-- | (1) | (SEQ ID NO: 163) |
| 2.7a | ucaagAUAUG AUCCGUAAGAGGACGGGAUAAACCUCAacu | (3) | (SEQ ID NO: 164) |
| 2.7b | -----------U---------------------------G--- | (1) | (SEQ ID NO: 165) |
| 2.8 | ucaagGGGUAUUGAGAUAUUCCGAUGUCCUAUGCUGUaCcu | (2) | (SEQ ID NO: 166) |
| 2.9 | ucaagGUUUCCGAAAGAAAUCGGGAAAACUGucu | (1) | (SEQ ID NO: 167) |
| 2.10 | ucaagUAAAUGAGUCCGUAGGAGGCGGGAUAUCCCAAcu | (1) | (SEQ ID NO: 168) |
| 2.11 | ucaagUCAUAUUACCGUUACUCCCGGGAUAAAGGAGaucu | (1) | (SEQ ID NO: 169) |
| 2.12 | ucaagAAUAAUCCGACUCGCGGGAUAACGAGAAGcu | (1) | (SEQ ID NO: 170) |
| 2.13 | ucaagAGUAAGUGCAGGAAUAUCAAUGAGGCAUCCAAaCcu | (1) | (SEQ ID NO: 171) |
| 2.14 | ucaagAUGAGAUAAAGUACCAAUCGAACCUAUCUAAUACGAcu | (1) | (SEQ ID NO: 172) |
| 2.15 | ucaagACCCAUUUAUUGCUACAAUAAUCCUUGACCUCaucu | (1) | (SEQ ID NO: 173) |
| 2.16 | ucaagUAAUACGAUAUACUAAUGAAGCCUAAUCUCGaucu | (1) | (SEQ ID NO: 174) |
| 2.17 | ucaagAACGAUCAUCGAUAUCWCUUCCGAUCCGUUUGucu | (1) | (SEQ ID NO: 175) |
| 2.18 | ucaagACGAUAGAACAAUCAUCUCCUACGACGAUGCAcu | (1) | (SEQ ID NO: 176) |
| 2.19 | ucaagAUAAUCAUGCAGGAUCAUUGAUCUCUUGUGCUaucu | (1) | (SEQ ID NO: 177) |
| 2.20 | ucaagAGUGAAGAUGUAAGUGCUUAUCUCUUGGGACAaucu | (1) | (SEQ ID NO: 178) |
| 2.21 | ucaagCAACAUUCUAUCAAGUAAAGUCACAUGAUaucu | (1) | (SEQ ID NO: 179) |
| 2.22 | ucaagGAUGUAUUACGAUUACUCUAUACUGCCUGCaucu | (1) | (SEQ ID NO: 180) |
| 2.23 | ucaagGGAUGAAAAUAGUUCCUAGUCUCAUUACGACCAcu | (1) | (SEQ ID NO: 181) |
| 2.24 | ucaagUAGUGUGAUAAUGAAUGGGUUUAUCGUAUGUGGCcu | (1) | (SEQ ID NO: 182) |
| 1.1 | ucaagAAUUCCGUUUCAGUCGGGAAAAACUGAACAaucu | (17) | (SEQ ID NO: 183) |

TABLE 7 starting RNA

5'-gggagcaucagacuuuuaaucugacaaucaagNNttccgNNNNNNNNcgggaaaaNNNN-
cuaugaagaauuuuauaucucuauugaaac-3'
(SEQ ID NO:184)

isolate

| | | |
|---|---|---|
| 3-2 | tcaagTAttccgAAGCTCAAcgggaaaaTGAGcta | (SEQ ID NO:185) |
| 3-3 | tcaagTAttccgAAGCTTGAcgggaaaaTAAGcta | (SEQ ID NO:186) |
| 3-6 | tcaagGAttccgAAGTTCAAcgggaaaaTGAActa | (SEQ ID NO:187) |
| 3-7 | tcaagAGttccgAAGGTTAAcgggaaaaTGACcta | (SEQ ID NO:188) |
| 3-25 | tcaagGAttccgAAGTGTAAcgggaaaaTGCActa | (SEQ ID NO:189) |
| 3-50 | tcaagTAttccgAGGTGCCAcgggaaaaGGCActa | (SEQ ID NO:190) |
| 3-22 | tcaagTAttccgAAGGGTAAcgggaaaaTGCCcta | (SEQ ID NO:191) |
| 3-8 | tcaagTAttccgAAGTACAAcgggaaaaCGTActa | (SEQ ID NO:192) |
| 3-13 | tcaagGAttccgAAGTGTAAcgggaaaaCGCActa | (SEQ ID NO:193) |
| 3-23 | tcaagGAttccgAAGCATAAcgggaaaaCATGcta | (SEQ ID NO:194) |
| 3-43 | tcaagGAttccgAAGTGTAAcgggaaaaAGCActa | (SEQ ID NO:195) |
| 3-45 | tcaagTAttccgAGGTGTGAcgggaaaaGACActa | (SEQ ID NO:196) |
| 3-21 | tcaagTAttccgAAGGGTAAcgggaaaaTGACcta | (SEQ ID NO:197) |
| 3-9 | tcaagTGttccgAGAGGCAAcgggaaaaGAGCcta | (SEQ ID NO:198) |
| 3-37 | tcaagTAttccgAAGGTGAAcgggaaaaTACActa | (SEQ ID NO:199) |
| 3-56 | tcaagAGttccgAAAGTCGAcgggaaaaTAGActa | (SEQ ID NO:200) |
| 3-58 | tcaagATttccgAGAGACAAcgggaaaaGAGTcta | (SEQ ID NO:201) |
| 3-39 | tcaagATttccgATGTGCAAcgggaaaaTGCActa | (SEQ ID NO:202) |
| 3-33 | tcaagTAttccgACGTAACAcgggaaaaGTTActa | (SEQ ID NO:203) |
| 3-46 | tcaagATttccgACGCACAAcgggaaaaTGTGcta | (SEQ ID NO:204) |
| 3-52 | tcaagTAttccgATGTCTAAcgggaaaaTAGGcta | (SEQ ID NO:205) |
| 3-16 | tcaagGGttccgATGCCCAAcgggaaaaGGGGcta | (SEQ ID NO:206) |
| 3-34 | tcaagAAttccgACGACGAAcgggaaaaACGTcta | (SEQ ID NO:207) |
| 3-35 | tcaagTAttccgATGTACAAcgggaaaaAGTActa | (SEQ ID NO:208) |
| 3-60 | tccagCGttccgTAAGTGGAcgggaaaaACCActa | (SEQ ID NO:209) |
| 3-27 | tcaagAGttccgTAAGGCCAcgggaaaaAGGTcta | (SEQ ID NO:210) |
| 3-15 | tcaagGAttccgAAAGGTAAcgggaaaaATGCcta | (SEQ ID NO:211) |
| 3-18 | tcaagAAttccgCTAGCCCAcgggaaaaGGGCcta | (2) (SEQ ID NO:212) |
| 3-31 | tcaagAAtt-cgTTAGTGTAcgggaaaaAACActa | (SEQ ID NO:213) |
| 3-26 | tcaagCGttccgATGGCTAAcgggaaaaATAGcta | (SEQ ID NO:214) |
| 3-32 | tcaagGAttccgTTTGTGCAcgggaaaaGGCActa | (SEQ ID NO:215) |
| 3-54 | tcaagAA-tccgTTTGCACAcgggaaaaCGTGcta | (SEQ ID NO:216) |
| 3-41 | tcaggAA-tccgAGAAGCTAcgggaaaaAGCGActa | (SEQ ID NO:217) |
| 3-29 | tcaagATttccgAGGTCCGAcgggaaaaTGGTcta | (SEQ ID NO:218) |
| 3-20 | tcaagTAttccgAAGGAAAAcgggaaaaCCACcta | (SEQ ID NO:219) |
| 3-36 | tcaagTGttccgAAGGAAAAcgggaaaaCCACcta | (SEQ ID NO:220) |
| 3-28 | tcaagAATtccgTAAGGGGTcgggaaaaACCctau | (SEQ ID NO:221) |
| 3-48 | tcaagGAttccgTATGTCCTcgggaaaaAGGActa | (SEQ ID NO:222) |

TABLE 7-continued

| | | |
|---|---|---|
| 3-59 | tcaagAGttccgAAAGGTAAcgggaaaaTTACcta | (SEQ ID NO:223) |
| 3-12 | tcaagTAttccgATAGTCAAcgggaaaaGCGActa | (SEQ ID NO:224) |
| 3-30 | tcaagTAttccgAGGTGTTAcgggaaaaCACGcta | (SEQ ID NO:225) |
| 3-11 | tcaagAAttccgTATGTGATcgggaaaaACCActa | (SEQ ID NO:226) |
| 3-17 | tcaagGAttccgATGTACAAcgggaaaaCTGTcta | (SEQ ID NO:227) |
| 3-24 | tcaagATttccgAAGGATAAcgggaaaaACCActa | (SEQ ID NO:228) |
| 3-51 | tcaagAAttccgAAGCGTAAcgggaaaaCATActa | (SEQ ID NO:229) |

TABLE 8

Template Construction: (SEQ ID NO: 230)
GGG AGCCA ACACC ACAAU UCCAA UCAAG -[32N]-
AUCUA UGAAA GAAUU UUAUA UCUCU AUUGA AAC

| Clone | 32n Random Region | | | | | | | | | |
|---|---|---|---|---|---|---|---|---|---|---|
| | Clones with AUCA loops | | | | | | | | | |
| 1 | CAG | AGAUA | UCACU | UCUGU | UCACC | AUCA | GGGGA | | | |
| 2 | AU | AUAAG | UAAUG | GAUGC | GCACC | AUCA | GGGCG | U | | |
| 3 | GGAAU | AAGUG | CUUUC | GUCGA | UCACC | AUCA | GGG | | | |
| 4 | UGGAG | UAUAA | ACCUU | UAUGG | UCACC | AUCA | GGG | | | |
| 5 | UCA | GAGAU | AGCUC | AUAGG | ACACC | AUCA | GGG | | | |
| 6 | CUGA | GAUAU | AUGAC | AGAGU | CCACC | AUCA | GGG | | | |
| 7 | GGAUU | AAUAU | GUCUG | CAUGA | UCACC | AUCA | GGG | | | |
| 8 | G | GGAGA | UUCUU | AGUAC | UCACC | AUCA | GGGGG | CA | | |
| 9 | A | AAUUA | UCUUC | GGAAU | GCACC | AUCA | GGGCA | UGG | | |
| 10 | G | GGAGA | UUCUU | ACUAC | UCACC | AUCA | GGGGG | CA | | |
| 11 | GGA | AUACU | UUCUU | UCGAU | GCACC | AUCA | GGGCG | | | |
| 12 | UCCA | AUAGA | GUUAG | UAGUU | GCACC | AUCA | GGGC | | | |
| 13 | GUAU | AGAUA | GUUCU | ACUGA | UCACG | AUCA | CGGG | | | |
| 14 | GGAU | AUGAU | CUUAU | GGUAU | GCACG | AUCA | CGGC | | | |
| 15 | UUG | UCUUU | CAUGU | AGUAA | GCACG | AUCA | CGGCG | | | |
| 16 | AGAGC | UAGUU | CUUGU | UUAAG | ACACG | AUCA | CGG | | | |
| 17 | ACG | AGAUU | UAUUU | AGAUG | UCACG | AUCA | CGGGC | | | |
| 18 | | UAAU | UGAUA | CUUGC | AGAGG | AUCA | CCCUG | CUCG | | |
| 19 | | AG | AGGAC | UCAUU | AGAGG | AUCA | CCCUA | GUGCG | G | |
| 20 | GAGAU | AUCAU | AAUUC | AUUGU | UGAGC | AUCA | GCC | | | |
| 21 | | | UGUAU | AGAGC | AUCA | GCCUA | UACAU | UGCGU | GGC | |
| 22 | | GAGA | UCAAU | AGUAA | GGACC | AUCA | GGCCU | GG | | |
| 23 | UGAG | AUAUC | UCUAU | AGUGU | GGAGC | AUCA | GCCC | | | |
| 24 | A | UGAGA | UAGAU | CAUGC | UCAGG | AUCA | CCGGG | | | |
| 25 | AGAG | UAUUC | UACAU | GAUUU | GCAUC | AUCU | GGGCG | | | |
| 26 | GGAUU | AAUUC | GUCUU | UUGAG | UGACG | AUCA | CGC | | | |
| 27 | | A | UUGCG | UAAUG | UUACC | AUCA | GGAAC | ACCGC | GU | |
| 28 | | | GA | GUAAG | AUAGC | AUCA | GCAUC | UUGUU | CCCGC | C |
| | Clones with ANCA loops | | | | | | | | | |
| 29 | GCGUU | AAUUU | GGAUU | AUAGA | UCACC | AACA | GGG | | | |
| 30 | GAGA | UGUUU | AGUAC | UUCAG | CCACC | AACA | GGGG | | | |
| 31 | GUCA | UACUC | UCUUU | GUnnU | GCACC | AACA | GGGC | | | |
| 32 | | | AUAGU | AGAGG | AACA | CCCUA | CUAAG | UCCCC | GCC | |
| 33 | CAACA | GAGAU | GAUAU | CAGGA | UGAGG | ACCA | CCC | | | |
| 34 | AGAUA | UAAUU | CUCCU | CUUGA | UGAGC | ACCA | GCC | | | |
| 35 | UAG | AGAUA | UGAGA | UAGUU | GCACC | ACCA | GGGUG | | | |
| 36 | AUA | UAGGA | GAUAU | UGUAG | UCACG | AGCA | CGGG | | | |
| | Clones with no ANCA loop | | | | | | | | | |
| 37 | UGCGUCACUUAUUGGAACUCUGGGUGGC | | | | | | | | | |
| 38 | CUGGAGGAGAUUGUGUAAUCGCUUGAACUCC | | | | | | | | | |

| Clone | Downstream Constant Region | | Δ of kcal mol | |
|---|---|---|---|---|
| Clones with AUCA loops | | | | |
| 1 | | CUAUG | AAAGA | −13.0 (SEQ ID NO: 231) |
| 2 | AU | CUAUG | AAAGA | −19.0 (SEQ ID NO: 232) |
| 3 | AU | CUAUG | AAAGA | −17.5 (SEQ ID NO: 233) |
| 4 | AU | CUAUG | AAAGA | −13.3 (SEQ ID NO: 234) |

TABLE 8-continued

Template Construction: (SEQ ID NO: 230)
GGG AGCCA ACACC ACAAU UCCAA UCAAG -[32N]-
AUCUA UGAAA GAAUU UUAUA UCUCU AUUGA AAC

| | | | | | |
|---|---|---|---|---|---|
| 5 | U | CUAUG | AAAGA | −13.6 | (SEQ ID NO: 235) |
| 6 | AU | CUAUG | AAAGA | −10.0 | (SEQ ID NO: 236) |
| 7 | AU | CUAUG | AAAGA | −12.6 | (SEQ ID NO: 237) |
| 8 | | CUAUG | AAAGA | −12.6 | (SEQ ID NO: 238) |
| 9 | | CUAUG | AAAGA | −10.9 | (SEQ ID NO: 239) |
| 10 | | CUAUG | AAAGA | −10.3 | (SEQ ID NO: 240) |
| 11 | U | CUAUG | AAAGA | −17.6 | (SEQ ID NO: 241) |
| 12 | AU | CUAUG | AAAGA | −11.8 | (SEQ ID NO: 242) |
| 13 | U | CUAUG | AAAGA | −9.7 | (SEQ ID NO: 243) |
| 14 | AU | CUAUG | AAAGA | −17.5 | (SEQ ID NO: 244) |
| 15 | A | CUAUG | AAAAGA | −10.5 | (SEQ ID NO: 245) |
| 16 | U | CUAUG | AAAGA | −12.6 | (SEQ ID NO: 246) |
| 17 | AC | CUAUG | AAAGA | −7.8 | (SEQ ID NO: 247) |
| 18 | AU | CUAUG | AAAGA | −10.8 | (SEQ ID NO: 248) |
| 19 | U | CUAUG | AAAGA | −15.0 | (SEQ ID NO: 249) |
| 20 | AU | CUAUG | AAAGA | −12.6 | (SEQ ID NO: 250) |
| 21 | A | CUAUG | AAAGA | −12.9 | (SEQ ID NO: 251) |
| 22 | | CUAUG | AAAGA | −14.6 | (SEQ ID NO: 252) |
| 23 | AU | CUAUG | AAAGA | −15.3 | (SEQ ID NO: 253) |
| 24 | | CUAUG | AAAGA | −11.3 | (SEQ ID NO: 254) |
| 25 | | UAUG | AAAGA | −9.3 | (SEQ ID NO: 255) |
| 26 | A | CUAUG | AAAGA | −13.3 | (SEQ ID NO: 256) |
| 27 | AU | CUAUG | AAAGA | −11.4 | (SEQ ID NO: 257) |
| 28 | AU | CUAUG | AAAGA | −14.6 | (SEQ ID NO: 258) |
| Clones with ANCA loops | | | | | |
| 29 | AC | CUAUG | AAAGA | −7.9 | (SEQ ID NO: 259) |
| 30 | U | CUAUG | AAAGA | −14.2 | (SEQ ID NO: 260) |
| 31 | AU | CUAUG | AAAGA | −9.4 | (SEQ ID NO: 261) |
| 32 | A | CUAUG | AAAGA | −9.5 | (SEQ ID NO: 262) |
| 33 | AU | CUAUG | A GGA | −11.8 | (SEQ ID NO: 263) |
| 34 | AU | CUAUG | AAAGA | −18.5 | (SEQ ID NO: 264) |
| 35 | AU | CUAUG | AAAGA | −16.8 | (SEQ ID NO: 265) |
| 36 | | CUAUG | AAAGA | −12.5 | (SEQ ID NO: 266) |
| Clones with no ANCA loop | | | | | |
| 37 | A | CUAUG | AAAGA | −17.7 | (SEQ ID NO: 267) |
| 38 | A | CUAUG | AAAGA | −9.7 | (SEQ ID NO: 268) |

TABLE 9 input RNA: 10,726
background: 72

| PROTEIN | COUNTS | MOLARITY | % BOUND |
|---|---|---|---|
| Acetylcholinesterase | 66 | $7.3 \times 10^{-6}$ | 0 |
| | 88 | $3.7 \times 10^{-6}$ | 0 |
| | 94 | $3.7 \times 10^{-7}$ | 0 |
| N-acetyl-β-D-glucosaminidase | 86 | $9.0 \times 10^{-9}$ | 0 |
| | 84 | $4.5 \times 10^{-9}$ | 0 |
| | 66 | $4.5 \times 10^{-10}$ | 0 |
| Actin | 70 | $1.9 \times 10^{-5}$ | 0 |
| | 76 | $9.7 \times 10^{-6}$ | 0 |
| | 58 | $9.7 \times 10^{-7}$ | 0 |
| Alcohol Dehydrogenase | 1130 | $1.4 \times 10^{-5}$ | 10.5 |
| | 116 | $7.0 \times 10^{-6}$ | 1.2 |
| | 90 | $7.0 \times 10^{-7}$ | 0 |
| Aldehyde Dehydrogenase | 898 | $2.1 \times 10^{-5}$ | 8.4 |
| | 1078 | $1.4 \times 10^{-5}$ | 10.1 |
| | 846 | $1.4 \times 10^{-6}$ | 7.9 |
| Angiotensin I, human | 284 | $2.6 \times 10^{-3}$ | 2.6 |
| | 74 | $1.3 \times 10^{-3}$ | 0 |
| | 70 | $1.3 \times 10^{-4}$ | 0 |
| Ascorbate Oxidase | 2734 | $2.4 \times 10^{-5}$ | 25.5 |
| | 1308 | $1.2 \times 10^{-5}$ | 12.2 |
| | 360 | $1.2 \times 10^{-6}$ | 3.4 |
| Atrial Natriuretic Factor | 4758 | $1.1 \times 10^{-4}$ | 44.4 |
| | 4416 | $5.5 \times 10^{-5}$ | 41.2 |
| | 4176 | $5.5 \times 10^{-6}$ | 38.9 |
| Bombesin | 1578 | $2.1 \times 10^{-4}$ | 14.7 |
| | 650 | $1.0 \times 10^{-4}$ | 6.1 |
| | 116 | $1.0 \times 10^{-5}$ | 1.1 |

TABLE 10

| sequence number | | no. of isolates | |
|---|---|---|---|
| 1a | tcaag----ATGAAGATACAGCTCCAGATGCTGGACACatct | (1) | (SEQ ID NO: 269) |
| 1b | ------G-G----------------T-------------------- | (1) | (SEQ ID NO: 270) |
| 1c | ------GAG----------------T-------------------- | (9) | (SEQ ID NO: 271) |
| 1d | -----CGAG----------------T-------------------- | (1) | (SEQ ID NO: 272) |
| 1e | ------GAG----------------TG------------------- | (1) | (SEQ ID NO: 273) |
| 2 | tcaagCTTGAGATACAGATTTCTGATTCTGGCTCGCTatct | (5) | (SEQ ID NO: 274) |
| 3a | tcaagATGGACTCGGTATCAAACGACCTTGAGACACatct | (4) | (SEQ ID NO: 275) |
| 3b | --------------------------G------------------ | (1) | (SEQ ID NO: 276) |
| 4a | tcaagATGGCTGGAGATACA-AACTATTTGGCTCGCCatct | (3) | (SEQ ID NO: 277) |
| 4b | ----------------------A---------------------- | (1) | (SEQ ID NO: 278) |
| 4c | ----------------------------G----------------- | (1) | (SEQ ID NO: 279) |
| 5 | tcaagAAGCCTTGAGATACACTATATAGTGGACCGGCatct | (3) | (SEQ ID NO: 280) |
| 6a | tcaagGGTGCATTGAGAAACACGTTTGTGGACTCTGT-atct | (2) | (SEQ ID NO: 281) |
| 6b | -----A---------------------------G--G---- | (2) | (SEQ ID NO: 282) |
| 7a | tcaagAGCGAAGATACAGAAGACAATACTGGACACGC-atct | (2) | (SEQ ID NO: 283) |
| 7b | ----------------------------------------A-T---- | (1) | (SEQ ID NO: 284) |
| 8 | tcaagGGGACTCTTTTCAATGATCCTTTAACCAGTCGatct | (2) | (SEQ ID NO: 285) |
| 9a | tcaagAAGAGACATTCGAATGATCCCTTAACCGGTTGatct | (1) | (SEQ ID NO: 286) |
| 9b | --------------C------------------------------- | (1) | (SEQ ID NO: 287) |
| 10 | tcaagCACGCATGACACAGATAAACTGGACTACGTGCatct | (1) | (SEQ ID NO: 288) |
| 11 | tcaagACACCTTGAGGTACTCTTAACAGGCTCGGTGatct | (1) | (SEQ ID NO: 289) |
| 12 | tcaagTTGAGATACCTGAACTTGGGACTCCTTGGTTGatct | (1) | (SEQ ID NO: 290) |
| 13 | tcaagGGATCTTGAGATACACACGAATGAGTGGACTCGatct | (1) | (SEQ ID NO: 291) |
| 14 | tcaagATCGAATTGAGAAACACTAACTGGCCTCTTTGatct | (1) | (SEQ ID NO: 292) |
| 15 | tcaagGCACAGATACAGGATATACTGGACACTGCCGatct | (1) | (SEQ ID NO: 293) |
| 16 | tcaagGGATATAACGAGTGATCCAGGTAACTCTGTTGatct | (1) | (SEQ ID NO: 294) |
| 17 | tcaagGTGGATTTGAGATACACGGAAGTGGAcTCTCCatct | (1) | (SEQ ID NO: 295) |
| 18 | tcaagAGATAATACAATGATCCTGCTCACTACAGTTGatct | (1) | (SEQ ID NO: 296) |
| 19 | tcaagGGAGGTATACAGAATGATCCGGTTGCTCGTTGatct | (1) | (SEQ ID NO: 297) |
| 20 | tcaagAGAAGAATAGTTGAAACAGATCAAACCTGGACatct | (1) | (SEQ ID NO: 298) |

TABLE 11

MOTIF I

| | | |
|---|---|---|
| aagGGAUCUUGAGAUACACACGA---AUGAGUGGACUCGaucuaugaaa | 13 | (1) (SEQ. ID NO: 299) |
| agGUGGAUUUGAGAUACACGG-------AAGUGGACUCUCCaucuauga | 17 | (1) (SEQ. ID NO: 300) |
| agGGUGCAUUGAGAAACACGU-------UUGUGGACUCUGUaucuauga | 6a | (2) (SEQ. ID NO: 301) |
| -CGACCUUGAGACACaucu-3'   5'-agAUGGACUCGGUAUCAAA- | 3A | (4) (SEQ. ID NO: 302) |
| agAUCGAAUUGAGAAACACUA-------ACUGGCCUCUUUGaucuaug | 14 | (1) (SEQ. ID NO: 303) |
| caaucaagUUGAGAUACCUGAA-----CUUGGGACUCCUUGGUUGAUc | 12 | (1) (SEQ. ID NO: 304) |
| aagAUGGCUGGAGAUACAAAAC-----UAUUUGG-CUCGCCaucuauga | 4a | (3) (SEQ. ID NO: 305) |
| aagAAGCCUUGAGAUACACUAU----AUAGUGGAC-CGGCaucuauga | 5 | (3) (SEQ. ID NO: 306) |
| aaucaagCUUGAGAUACAGAUU-UCUGAUUCUGG-CUCGCUaucuauga | 2 | (5) (SEQ. ID NO: 307) |
| aagACACCUUGAGGUACUCUU-------AACAGG-CUCGGUGaucuaug | 11 | (1) (SEQ. ID NO: 308) |

TABLE 11-continued

MOTIF II ucaagGAGAUGAAGAUACAGCUCUA --- GAUGCUGGACACaucuauga  1C  (9)  (SEQ. ID NO: 309)

aaucaagAGCGAAGAUACAGAAGACAA --- UACUGGACACGcaucuau  7A  (2)  (SEQ. ID NO: 310)

aaucaagGCAGCAGAUACAGGAU ------ AUACUGGACACUGCCGAUc  15  (1)  (SEQ. ID NO: 311)

gAGAAGAAUAGUUGAAACAGAUC ----- AAACCUGGACaucuaugaaa  20  (1)  (SEQ. ID NO: 312)

aucaagCACGCAUGACACAGAUA ------ AACUGGACUACGUGCAUc  10  (1)  (SEQ. ID NO: 313)

MOTIF III caaucaagAGAUAAUACAAUGAUCCUGCUCACUACAGUUGaucuaugaaagaauuuuauaucucuau  18  (1)  (SEQ. ID NO: 314)

ucaagAAGAGACAUUCGAAUGAUCCCUU --- AACCGGUUGaucuaugaaagaauuuuauaucucuau  9a  (1)  (SEQ. ID NO: 315)

ucaagGGGACUCUUUUCAAUGAUCCUUU --- AACCAGUCGaucuauga a a ga au uuuauaucucuau  8  (2)  (SEQ. ID NO: 316)

ucaagGGAGGUAUACAGAAUGAUCCGGU --- UGCUCGUUGaucuaugaaagaauuuuauaucucuau  19  (1)  (SEQ. ID NO: 317)

aaucaagGGAUAUAACGAGUGAUCCAGGU-AACUCUGUUGaucuaugaaagaauuuuauaucucuau  16  (1)  (SEQ. ID NO: 318)

TABLE 12

| Clone | Freq. | Stem 1(a) | Loop 1 | Stem 2(a) | Loop 2 | Stem 2(b) | Loop 3 | Stem 1(b) | Seq. No. |
|---|---|---|---|---|---|---|---|---|---|
| 13 | 1 | GGAUC | UUGAGAUA | CAC | ACGAAUGA | GUG | GACUC | Gaucu | SEQ ID NO: 319 |
| 12 | 1 | caaucaag | UUGAGAUA | CC | UGAACUU | GG | GACUC | CUUGGUUG | SEQ ID NO: 320 |
| 6a | 2 | gGGUGCA | UUGAGAAA | CACG | UU | UGUG | GACUC | UGUaucu | SEQ ID NO: 321 |
| 3a | 4 | ACC | UUGAGACA | Caucu | -OPEN- | agAUG | GACUC | GGU | SEQ ID NO: 322 |
| 14 | 1 | agAUCGAA | UUGAGAUA | CA | CUAAC | UG | GCCUC | UUUGaucu | SEQ ID NO: 323 |
| 2 | 5 | agC | UUGAGAUA | CAGA | UUUCUGAU | UCUG | G-CUC | GCU | SEQ ID NO: 324 |
| 11 | 1 | CACC | UUGAGGUA | CU | CUUAAC | AG | G-CUC | GGUG | SEQ ID NO: 325 |
| 4a | 3 | agAUGGC | UGGAGAUA | CAAA | CUA | UUUG | G-CUC | GCCaucu | SEQ ID NO: 326 |
| 5 | 3 | agA-A-GCC | UUGAGAUA | CACUAU | | AUAGUG | GAC-C | GGC-a-ucu | SEQ ID NO: 327 |
| 17 | 1 | agGUGGA | UUUGAGAUA | CAC | GGAA | GUG | GACUC | UCCaucu | SEQ ID NO: 328 |
| 1c | 9 | AGAUG | AAGAUA | CAGC | UCUAGAU | GCUG | GACA | Caucu | SEQ ID NO: 329 |
| 7a | 2 | agAGCG | AAGAUA | CAG | AAGACAAUA | CUG | GACA | CGC-a-ucu | SEQ ID NO: 330 |
| 15 | 1 | gGCAG | CAGAUA | CAG | GAUAUA | CUG | GACA | CUGCC | SEQ ID NO: 331 |
| 20 | 1 | AUAG | UUGAAA | CAG | AUCAAAC | CUG | GACau | cuau | SEQ ID NO: 332 |
| 10 | 1 | gCACG | CAUGACA | CAG | AUAAA | CUG | GACUA | CGUGC | SEQ ID NO: 333 |
| WT | — | GACGCUG | ACGGUA | CA | -OPEN- | UG | GGCG | CAGCGUC | SEQ ID NO: 334 |
| CON | — | GGGACCC | UUGAGAUA | CACGGC | UUCGG | CCGUG | GACUC | GGGUCUC | SEQ ID NO: 335 |

TABLE 13

| Clone | Freq. | $\Delta G_f$ Consensus Structure | $\Delta G_f$ Competing Structure | Information Score Sequence I | Information Score Sequence II | Total Information Score | $K_a/K_a^{6a}$ |
|---|---|---|---|---|---|---|---|
| 13 | 1 | −9.9 | −9.7 | 18.25 | 12.74 | 30.99 | 0.576 |
| 12 | 1 | −8.9 | −10.2 | 15.79 | 10.74 | 26.53 | 0.298 |
| 6a | 2 | −11.6 | −9.9 | 16.38 | 12.74 | 29.12 | 1.000 |
| 6b | 2 | — | −11.5 | 16.38 | 12.74 | 29.12 | 0.042 |
| 3a | 4 | −9.5 | −8.8 | 14.79 | 12.74 | 27.53 | 0.405 |
| 14 | 1 | −10.1 | −10.2 | 16.38 | 10.16 | 26.54 | — |
| 2 | 5 | −8.5 | −9.1 | 18.25 | 3.87 | 22.12 | 0.114 |

TABLE 13-continued

| Clone | Freq. | $\Delta G_f$ Consensus Structure | $\Delta G_f$ Competing Structure | Information Score Sequence I | Information Score Sequence II | Total Information Score | $K_a/K_a^{6a}$ |
|---|---|---|---|---|---|---|---|
| 11 | 1 | −8.6 | −10.9 | 13.21 | 6.93 | 20.14 | — |
| 1a | 3 | −14.2 | −15.6 | 17.40 | 7.46 | 24.86 | 0.564 |
| 5 | 3 | −10.4 | −10.8 | 18.25 | 7.83 | 26.08 | 0.567 |
| 17 | 1 | −14.8 | −12.0 | 18.25 | 12.74 | 30.99 | 0.247 |
| 10 | 9 | −10.0 | −13.2 | 15.67 | 11.42 | 27.09 | 0.154 |
| 7a | 2 | −6.4 | −5.6 | 13.21 | 11.42 | 24.63 | — |
| 15 | 1 | −11.1 | −10.4 | 12.62 | 11.42 | 24.04 | 0.455 |
| 20 | 1 | −4.8 | −6.4 | 7.39 | 4.91 | 12.30 | 0.191 |
| 10 | 1 | −10.2 | −8.6 | 6.60 | 10.16 | 16.76 | — |
| 8 | — | — | — | — | — | — | 0.292 |
| 9a | — | — | — | — | — | — | 0.106 |
| 18 | — | — | — | — | — | — | 0.149 |
| WT | — | −27.0 | −26.3 | — | — | — | 0.180 |
| CON | — | 21.1 | −19.7 | — | — | — | 0.429 |
| 32n | — | — | — | — | — | — | 0.015 |
| Evol Pop. | — | — | — | — | — | — | 0.435 |

Sequence I = UUGAGAUACA (SEQ ID NO: 48)
Sequence II = UGGACUC (SEQ ID NO: 347)

We claim:

1. A method for detecting the presence or absence of a target molecule in a sample which may contain said target molecule comprising:
   a) exposing said sample which may contain said target molecule to a non-naturally occurring nucleic acid ligand of said target molecule, wherein said nucleic acid ligand is not a nucleic acid having the known physiological function of being bound by said target molecule, under conditions wherein a target molecule; nucleic acid ligand binding pair is formed if said target molecule is present, wherein said binding is not due to Watson/Crick base pairing; and
   b) determining whether said target molecule:nucleic acid ligand binding pair is formed, thereby detecting the presence or absence of the target molecule in the sample.

2. The method of claim 1 wherein said nucleic acid ligand is single-stranded.

3. The method of claim 2 wherein said single-stranded nucleic acid ligand is ribonucleic acid.

4. The method of claim 2 wherein said single-stranded nucleic acid ligand is deoxyribonucleic acid.

5. The method of claim 1 wherein said nucleic acid ligand is labeled.

6. The method of claim 5 wherein said label is a radiolabel.

7. The method of claim 1 wherein said target molecule is a protein.

8. The method of claim 7 wherein said protein is not known to bind nucleic acids as part of its biological function.

9. The method of claim 1 wherein said target molecule is a small molecule.

10. The method of claim 1 wherein said target molecule is a controlled substance.

11. The method of claim 1 wherein said target molecule is a metabolite.

12. The method of claim 1 wherein said sample is a biological substance.

13. The method of claim 1 wherein said detection is achieved by PCR amplification of said nucleic acid ligand.

14. A method for detecting the presence or absence of a target molecule in a sample which may contain said target molecule comprising:
   a) identifying a nucleic acid ligand from a candidate mixture of nucleic acids, said nucleic acid ligand being a ligand of said target molecule, by a method comprising:
      i) contacting the candidate mixture with said target molecule, wherein nucleic acids having an increased affinity to said target molecule relative to the candidate mixture may be partitioned from the remainder of the candidate mixture;
      ii) partitioning the increased affinity nucleic acids from the remainder of the candidate mixture; and
      iii) amplifying the increased affinity nucleic acids to yield a ligand-enriched mixture of nucleic acids, whereby an increased affinity nucleic acid ligand may be identified;
   b) exposing said sample which may contain said target molecule to said increased affinity nucleic acid ligand of said target molecule under conditions wherein a target molecule; nucleic acid ligand binding pair is formed if said target molecule is present; and
   c) determining whether said target molecule:nucleic acid ligand binding pair is formed, thereby detecting the presence or absence of the target molecule in the sample.

15. The method of claim 14 further comprising:
   iv) repeating steps i), ii) and iii).

16. The method of claim 14 wherein said nucleic acid ligand is single-stranded.

17. The method of claim 16 wherein said single-stranded nucleic acid ligand is ribonucleic acid.

18. The method of claim 16 wherein said single-stranded nucleic acid ligand is deoxyribonucleic acid.

19. The method of claim 14 wherein said target molecule is a protein.

20. The method of claim 19 wherein said protein is not known to bind nucleic acids as part of its biological function.

21. The method of claim 14 wherein said target molecule is a controlled substance.

22. The method of claim 14 wherein said target molecule is a metabolite.

23. The method of claim 14 wherein said target molecule is a small molecule.

24. The method of claim 14 wherein said sample is a biological substance.

25. The method of claim 14 wherein said detection is achieved by PCR amplification of said nucleic acid ligand.

26. The method of claim 14 wherein said candidate mixture is prepared by synthesis from a template comprising a region of conserved sequence and a region of randomized and/or biased sequence.

27. The method of claim 14 wherein said candidate mixture comprises nucleic acids each comprising a region of conserved sequence and a region of randomized sequence.

28. A method for measuring the amount of a target molecule in a sample which may contain said target molecule comprising:
   a) exposing said sample which may contain said target molecule to a nucleic acid ligand of said target molecule, wherein said nucleic acid ligand is not a nucleic acid having the known physiological function of being bound by the target molecule, under conditions wherein a target molecule; nucleic acid ligand binding pair is formed;
   b) determining whether said target molecule:nucleic acid ligand binding pair is formed wherein said binding is not due to Watson/Crick base pairing; and
   c) measuring the amount of the target molecule in the sample by quantitatively detecting the nucleic acid ligand.

29. The method of claim 28 wherein said nucleic acid ligand is single-stranded.

30. The method of claim 29 wherein said single-stranded nucleic acid ligand is ribonucleic acid.

31. The method of claim 29 wherein said single-stranded nucleic acid ligand is deoxyribonucleic acid.

32. The method of claim 28 wherein said nucleic acid ligand is labeled.

33. The method of claim 32 wherein said label is a radiolabel.

34. The method of claim 28 wherein said target molecule is a protein.

35. The method of claim 34 wherein said protein is not known to bind nucleic acids as part of its biological function.

36. The method of claim 28 wherein said target molecule is a small molecule.

37. The method of claim 28 wherein said target molecule is a controlled substance.

38. The method of claim 28 wherein said target molecule is a metabolite.

39. The method of claim 28 wherein said sample is a biological substance.

40. The method of claim 28 wherein said detection is achieved by PCR amplification of said nucleic acid ligand.

41. The method of claim 28 wherein said measurement is qualitative.

42. The method of claim 28 wherein said measurement is quantitative.

43. A method for measuring the amount of a target molecule in a sample which may contain said target molecule comprising:
   a) identifying a nucleic acid ligand from a candidate mixture of nucleic acids, said nucleic acid ligand being a ligand of said target molecule, by a method comprising:
      i) contacting the candidate mixture with said target molecule, wherein nucleic acids having an increased affinity to said target molecule relative to the candidate mixture may be partitioned from the remainder of the candidate mixture;
      ii) partitioning the increased affinity nucleic acids from the remainder of the candidate mixture; and
      iii) amplifying the increased affinity nucleic acids to yield a ligand-enriched mixture of nucleic acids, whereby an increased affinity nucleic acid ligand may be identified;
   b) exposing said sample which may contain said target molecule to said increased affinity nucleic acid ligand of said target molecule under conditions wherein a target molecule; nucleic acid ligand binding pair is formed;
   c) determining whether said target molecule:nucleic acid ligand binding pair is formed; and
   d measuring the amount of the target molecule in the sample, by quantitatively detecting the nucleic acid ligand.

44. The method of claim 43 further comprising:
   iv) repeating steps i), ii) and iii).

45. The method of claim 43 wherein said nucleic acid ligand is single-stranded.

46. The method of claim 45 wherein said single-stranded nucleic acid ligand is ribonucleic acid.

47. The method of claim 45 wherein said single-stranded nucleic acid ligand is deoxyribonucleic acid.

48. The method of claim 43 wherein said target molecule is a protein.

49. The method of claim 48 wherein said protein is not known to bind nucleic acids as part of its biological function.

50. The method of claim 43 wherein said target molecule is a controlled substance.

51. The method of claim 43 wherein said target molecule is a metabolite.

52. The method of claim 43 wherein said target molecule is a small molecule.

53. The method of claim 43 wherein said sample is a biological substance.

54. The method of claim 43 wherein said measurement is qualitative.

55. The method of claim 43 wherein said measurement is quantitative.

56. The method of claim 43 wherein said candidate mixture is prepared by synthesis from a template comprising a region of conserved sequence and a region of randomized and/or biased sequence.

57. The method of claim 43 wherein said candidate mixture comprises nucleic acids each comprising a region of conserved sequence and a region of randomized sequence.

* * * * *